US012575816B2

(12) United States Patent
Valdez et al.

(10) Patent No.: US 12,575,816 B2
(45) Date of Patent: Mar. 17, 2026

(54) TRANSCATHETER MEDICAL IMPLANT DELIVERY

(71) Applicant: Edwards Lifesciences Corporation, Irvine, CA (US)

(72) Inventors: Michael G. Valdez, Riverside, CA (US); Cristobal R. Hernandez, Santa Ana, CA (US); Eric Jason Noda, Rancho Santa Margarita, CA (US); Hien T Nguyen, Aliso Viejo, CA (US); Trizzie Trang Dang, Santa Ana, CA (US); Lillian Grace Myers, Prairie Village, KS (US); Linda Thai, Mission Viejo, CA (US); Daniel James Murray, Orange, CA (US); Don Huy Tran, Westminster, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 362 days.

(21) Appl. No.: 17/744,127

(22) Filed: May 13, 2022

(65) Prior Publication Data

US 2022/0273279 A1 Sep. 1, 2022

Related U.S. Application Data

(63) Continuation of application No. PCT/US2020/059304, filed on Nov. 6, 2020.
(Continued)

(51) Int. Cl.
| | |
|---|---|
| *A61B 17/00* | (2006.01) |
| *A61B 17/34* | (2006.01) |
| *A61M 27/00* | (2006.01) |

(52) U.S. Cl.
CPC .... *A61B 17/00234* (2013.01); *A61B 17/3468* (2013.01); *A61B 17/3478* (2013.01);
(Continued)

(58) Field of Classification Search
CPC .......... A61B 17/00234; A61B 17/3468; A61B 17/3478; A61B 2017/00247;
(Continued)

(56) References Cited

U.S. PATENT DOCUMENTS

| | | | |
|---|---|---|---|
| 3,538,917 | A | 11/1970 | Selker |
| 3,675,656 | A | 7/1972 | Hakim |

(Continued)

FOREIGN PATENT DOCUMENTS

| | | | |
|---|---|---|---|
| CN | 106725643 A | 5/2017 | |
| CN | 111317516 A | 6/2020 | |

(Continued)

OTHER PUBLICATIONS

Emil Mantini, MD, et al., Title: Congenital Anomalies Involving the Coronary Sinus, Circulation, Journal of the American Heart Association, vol. XXXIII, Feb. 1966, pp. 317-327.
(Continued)

*Primary Examiner* — Rebecca E Eisenberg
*Assistant Examiner* — Alessandro R Del Priore
(74) *Attorney, Agent, or Firm* — Chang and Hale LLP

(57) ABSTRACT

A medical implant delivery system can comprise a puncture needle, a medical implant delivery catheter and the puncture needle being configured to be slidably advanced through a puncture needle lumen of the medical implant delivery catheter, a medical implant device positioned on the medical implant delivery catheter, and an outer delivery catheter comprising a medical implant delivery lumen, the medical implant delivery catheter being configured to slidably extend through the medical implant delivery lumen. A medical implant delivery system can comprise a puncture needle, a medical implant delivery catheter and the puncture needle being configured to slidably extend through the puncture needle lumen of the medical implant delivery catheter, a
(Continued)

medical implant device positioned on the medical implant delivery catheter, an elongate housing adjacent to the medical implant delivery catheter, and an outer sheath around a portion of the medical implant delivery catheter and the elongate housing.

18 Claims, 26 Drawing Sheets

Related U.S. Application Data

(60) Provisional application No. 62/935,214, filed on Nov. 14, 2019.

(52) U.S. Cl.
    CPC . *A61M 27/002* (2013.01); *A61B 2017/00247* (2013.01); *A61B 2017/00292* (2013.01)

(58) Field of Classification Search
    CPC ........... A61B 2017/00292; A61B 2017/00252; A61B 2017/00296; A61B 2017/1107; A61B 2017/1139; A61B 2017/22069; A61B 17/11; A61B 2017/22052; A61M 27/002; A61M 2025/0087; A61M 2025/0004
    See application file for complete search history.

(56) References Cited

U.S. PATENT DOCUMENTS

| | | | |
|---|---|---|---|
| 3,730,186 A | 5/1973 | Edmunds, Jr. et al. | |
| 3,853,126 A | 12/1974 | Schulte | |
| 3,882,862 A | 5/1975 | Berend | |
| 3,882,882 A | 5/1975 | Preisig | |
| 3,903,894 A | 9/1975 | Rosen et al. | |
| 4,256,094 A | 3/1981 | Kapp et al. | |
| 4,428,365 A | 1/1984 | Hakky | |
| 4,556,050 A | 12/1985 | Hodgson et al. | |
| 4,578,061 A | 3/1986 | Lemelson | |
| 4,586,501 A | 5/1986 | Claracq | |
| 4,601,718 A | 7/1986 | Possis et al. | |
| 4,655,777 A | 4/1987 | Dunn et al. | |
| 4,708,140 A | 11/1987 | Baron | |
| 4,712,551 A | 12/1987 | Rayhanabad | |
| 4,739,762 A | 4/1988 | Palmaz | |
| 4,762,128 A | 8/1988 | Rosenbluth | |
| 4,774,949 A | 10/1988 | Fogarty | |
| 4,828,544 A | 5/1989 | Lane et al. | |
| 4,842,585 A * | 6/1989 | Witt .................. | A61B 17/3401 604/274 |
| 4,861,336 A | 8/1989 | Helzel | |
| 4,881,939 A | 11/1989 | Newman | |
| 4,946,457 A | 8/1990 | Elliott | |
| 4,950,227 A | 8/1990 | Savin et al. | |
| 4,961,729 A | 10/1990 | Vaillancourt | |
| 4,997,431 A | 3/1991 | Isner et al. | |
| 5,026,377 A | 6/1991 | Burton et al. | |
| 5,054,492 A | 10/1991 | Scribner et al. | |
| 5,108,420 A | 4/1992 | Marks | |
| 5,109,420 A | 4/1992 | Nonaka | |
| 5,114,408 A | 5/1992 | Fleischhaker et al. | |
| 5,167,239 A | 12/1992 | Cohen et al. | |
| 5,190,528 A | 3/1993 | Fonger et al. | |
| 5,193,546 A | 3/1993 | Shaknovich | |
| 5,201,757 A | 4/1993 | Heyn et al. | |
| 5,242,397 A | 9/1993 | Barath et al. | |
| 5,242,410 A | 9/1993 | Melker | |
| 5,258,042 A | 11/1993 | Mehta | |
| 5,267,940 A | 12/1993 | Moulder | |
| 5,287,861 A | 2/1994 | Wilk | |
| 5,320,613 A | 6/1994 | Houge et al. | |
| 5,330,496 A | 7/1994 | Alferness | |
| 5,334,217 A | 8/1994 | Das | |
| 5,345,940 A | 9/1994 | Seward et al. | |
| 5,354,279 A | 10/1994 | Hofling | |
| 5,366,490 A | 11/1994 | Edwards et al. | |
| 5,373,849 A | 12/1994 | Maroney et al. | |
| 5,419,777 A | 5/1995 | Hofling | |
| 5,423,878 A | 6/1995 | Franz | |
| 5,429,634 A | 7/1995 | Narciso, Jr. | |
| 5,431,700 A | 7/1995 | Sloan | |
| 5,443,497 A | 8/1995 | Venbrux | |
| 5,445,600 A | 8/1995 | Abdulla | |
| 5,445,646 A | 8/1995 | Euteneuer et al. | |
| 5,456,284 A | 10/1995 | Ryan et al. | |
| 5,456,712 A | 10/1995 | Maginot | |
| 5,462,523 A | 10/1995 | Samson et al. | |
| 5,464,395 A | 11/1995 | Faxon et al. | |
| 5,491,224 A | 2/1996 | Bittner et al. | |
| 5,492,304 A | 2/1996 | Smith et al. | |
| 5,496,311 A | 3/1996 | Abele et al. | |
| 5,499,630 A | 3/1996 | Hiki et al. | |
| 5,507,724 A | 4/1996 | Hofmann et al. | |
| 5,507,725 A | 4/1996 | Savage et al. | |
| 5,538,504 A | 7/1996 | Linden et al. | |
| 5,551,954 A | 9/1996 | Buscemi et al. | |
| 5,554,182 A | 9/1996 | Dinh et al. | |
| 5,570,693 A | 11/1996 | Jang et al. | |
| 5,571,086 A | 11/1996 | Kaplan et al. | |
| 5,571,151 A | 11/1996 | Gregory | |
| 5,588,960 A | 12/1996 | Edwards et al. | |
| 5,597,146 A | 1/1997 | Putman | |
| 5,597,378 A | 1/1997 | Jervis | |
| 5,599,300 A | 2/1997 | Weaver et al. | |
| 5,614,204 A | 3/1997 | Cochrum | |
| 5,628,784 A | 5/1997 | Strecker | |
| 5,661,133 A | 8/1997 | Leiden et al. | |
| 5,662,609 A | 9/1997 | Slepian | |
| 5,662,711 A | 9/1997 | Douglas | |
| 5,665,077 A | 9/1997 | Rosen et al. | |
| 5,669,880 A | 9/1997 | Solar | |
| 5,682,906 A | 11/1997 | Sterman et al. | |
| 5,690,670 A | 11/1997 | Davidson | |
| 5,693,029 A | 12/1997 | Leonhardt | |
| 5,704,361 A | 1/1998 | Seward et al. | |
| 5,704,926 A | 1/1998 | Sutton | |
| 5,713,363 A | 2/1998 | Seward et al. | |
| 5,713,853 A | 2/1998 | Clark et al. | |
| 5,718,725 A | 2/1998 | Sterman et al. | |
| 5,724,975 A | 3/1998 | Negus et al. | |
| 5,724,977 A | 3/1998 | Yock et al. | |
| 5,728,123 A | 3/1998 | Lemelson et al. | |
| 5,735,847 A | 4/1998 | Gough et al. | |
| 5,738,658 A | 4/1998 | Maus et al. | |
| 5,743,874 A | 4/1998 | Fischell et al. | |
| 5,755,682 A | 5/1998 | Knudson et al. | |
| 5,756,696 A | 5/1998 | Gray et al. | |
| 5,771,895 A | 6/1998 | Slager | |
| 5,772,629 A | 6/1998 | Kaplan | |
| 5,772,632 A | 6/1998 | Forman | |
| 5,807,258 A | 9/1998 | Cimochowski et al. | |
| 5,807,306 A | 9/1998 | Shapland et al. | |
| 5,810,780 A | 9/1998 | Brimhall et al. | |
| 5,814,005 A | 9/1998 | Barra et al. | |
| 5,827,216 A | 10/1998 | Igo et al. | |
| 5,830,222 A | 11/1998 | Makower | |
| 5,830,224 A | 11/1998 | Cohn et al. | |
| 5,836,913 A | 11/1998 | Orth et al. | |
| 5,843,090 A | 12/1998 | Schuetz | |
| 5,843,170 A | 12/1998 | Ahn | |
| 5,944,738 A | 8/1999 | Amplatz et al. | |
| 5,951,569 A | 9/1999 | Tuckey et al. | |
| 5,954,691 A | 9/1999 | Prosl | |
| 5,989,280 A | 11/1999 | Euteneuer et al. | |
| 6,019,788 A | 2/2000 | Butters et al. | |
| 6,042,589 A | 3/2000 | Marianne | |
| 6,053,891 A | 4/2000 | DeCampli | |
| 6,081,738 A | 6/2000 | Hinohara et al. | |
| 6,086,553 A | 7/2000 | Akbik | |
| 6,092,526 A | 7/2000 | LaFontaine et al. | |
| 6,095,878 A | 8/2000 | Van Balen | |
| 6,113,612 A | 9/2000 | Swanson et al. | |
| 6,120,494 A | 9/2000 | Jonkman | |

(56)                  References Cited

U.S. PATENT DOCUMENTS

| | | | |
|---|---|---|---|
| 6,120,522 | A | 9/2000 | Vrba et al. |
| 6,120,534 | A | 9/2000 | Ruiz |
| 6,152,937 | A | 11/2000 | Peterson et al. |
| 6,165,185 | A | 12/2000 | Shennib et al. |
| 6,168,620 | B1 | 1/2001 | Kerr |
| 6,168,820 | B1 | 1/2001 | Garwood et al. |
| 6,174,681 | B1 | 1/2001 | Halling et al. |
| 6,190,353 | B1 | 2/2001 | Makower et al. |
| 6,193,734 | B1 | 2/2001 | Bolduc et al. |
| 6,196,230 | B1 | 3/2001 | Hall et al. |
| 6,241,743 | B1 | 6/2001 | Levin et al. |
| 6,248,117 | B1 | 6/2001 | Blatter |
| 6,251,116 | B1 | 6/2001 | Shennib et al. |
| 6,254,631 | B1 | 7/2001 | Thompson |
| 6,280,412 | B1 | 8/2001 | Pederson, Jr. et al. |
| 6,283,951 | B1 | 9/2001 | Flaherty et al. |
| 6,287,280 | B1 | 9/2001 | Lampropoulos et al. |
| 6,287,332 | B1 | 9/2001 | Bolz et al. |
| 6,290,728 | B1 | 9/2001 | Phelps et al. |
| 6,302,875 | B1 | 10/2001 | Makower et al. |
| 6,302,892 | B1 | 10/2001 | Wilk |
| 6,302,905 | B1 | 10/2001 | Goldsteen et al. |
| 6,309,415 | B1 | 10/2001 | Pulnev et al. |
| 6,315,752 | B1 | 11/2001 | DiMatteo |
| 6,325,798 | B1 | 12/2001 | Edwards et al. |
| 6,361,545 | B1 | 3/2002 | Macoviak et al. |
| 6,375,615 | B1 | 4/2002 | Flaherty et al. |
| 6,387,116 | B1 | 5/2002 | Mckenzie et al. |
| 6,387,119 | B2 | 5/2002 | Wolf et al. |
| 6,391,036 | B1 | 5/2002 | Berg et al. |
| 6,402,767 | B1 | 6/2002 | Nash et al. |
| 6,443,158 | B1 | 9/2002 | LaFontaine et al. |
| 6,451,048 | B1 | 9/2002 | Berg et al. |
| 6,458,140 | B2 | 10/2002 | Akin et al. |
| 6,464,665 | B1 | 10/2002 | Heuser |
| 6,468,303 | B1 | 10/2002 | Amplatz et al. |
| 6,475,226 | B1 | 11/2002 | Belef et al. |
| 6,494,889 | B1 | 12/2002 | Fleischman et al. |
| 6,503,247 | B2 | 1/2003 | Swartz et al. |
| 6,506,201 | B2 | 1/2003 | Di Caprio et al. |
| 6,508,824 | B1 | 1/2003 | Flaherty et al. |
| 6,561,998 | B1 | 5/2003 | Roth et al. |
| 6,562,066 | B1 | 5/2003 | Martin |
| 6,565,542 | B2 | 5/2003 | Kumar et al. |
| 6,575,168 | B2 | 6/2003 | LaFontaine et al. |
| 6,579,311 | B1 | 6/2003 | Makower |
| 6,589,251 | B2 | 7/2003 | Yee et al. |
| 6,595,941 | B1 | 7/2003 | Blatter |
| 6,602,241 | B2 | 8/2003 | Makower et al. |
| 6,613,074 | B1 | 9/2003 | Mitelberg et al. |
| 6,616,624 | B1 | 9/2003 | Kieval |
| 6,616,675 | B1 | 9/2003 | Evard et al. |
| 6,620,202 | B2 | 9/2003 | Bottcher et al. |
| 6,623,494 | B1 | 9/2003 | Blatter |
| 6,626,920 | B2 | 9/2003 | Whayne |
| 6,638,293 | B1 | 10/2003 | Makower et al. |
| 6,692,482 | B2 | 2/2004 | Heller et al. |
| 6,695,878 | B2 | 2/2004 | McGuckin, Jr. et al. |
| 6,699,256 | B1 | 3/2004 | Logan et al. |
| 6,702,828 | B2 | 3/2004 | Whayne |
| 6,709,414 | B2 | 3/2004 | Weitzel et al. |
| 6,709,444 | B1 | 3/2004 | Makower |
| 6,712,836 | B1 | 3/2004 | Berg et al. |
| 6,719,804 | B2 | 4/2004 | St. Pierre |
| 6,726,659 | B1 | 4/2004 | Stocking et al. |
| 6,726,677 | B1 | 4/2004 | Flaherty et al. |
| 6,736,825 | B2 | 5/2004 | Blatter et al. |
| 6,740,426 | B2 | 5/2004 | Kawachi et al. |
| 6,743,244 | B2 | 6/2004 | Blatter et al. |
| 6,743,259 | B2 | 6/2004 | Ginn |
| 6,746,426 | B1 | 6/2004 | Flaherty et al. |
| 6,748,484 | B1 | 6/2004 | Henderson et al. |
| 6,758,854 | B1 | 7/2004 | Butler et al. |
| 6,776,785 | B1 | 8/2004 | Yencho et al. |
| 6,797,083 | B2 | 9/2004 | Peterson |
| 6,802,858 | B2 | 10/2004 | Gambale et al. |
| 6,805,706 | B2 | 10/2004 | Solovay et al. |
| 6,808,498 | B2 | 10/2004 | Laroya et al. |
| 6,827,698 | B1 | 12/2004 | Kleinekofort |
| 6,847,348 | B2 | 1/2005 | Rojewski |
| 6,854,172 | B2 | 2/2005 | Kaese et al. |
| 6,858,035 | B2 | 2/2005 | Whayne |
| 6,869,437 | B1 | 3/2005 | Hausen et al. |
| 6,893,413 | B2 | 5/2005 | Martin |
| 6,913,600 | B2 | 7/2005 | Valley et al. |
| 6,913,607 | B2 | 7/2005 | Ainsworth et al. |
| 6,915,154 | B1 | 7/2005 | Docherty et al. |
| 6,926,690 | B2 | 8/2005 | Renati |
| 6,972,023 | B2 | 12/2005 | Whayne et al. |
| 6,979,351 | B2 | 12/2005 | Forsell et al. |
| 6,985,774 | B2 | 1/2006 | Kieval et al. |
| 7,002,491 | B2 | 2/2006 | Robbins |
| 7,008,397 | B2 | 3/2006 | Tweden et al. |
| 7,011,094 | B2 | 3/2006 | Rapacki et al. |
| 7,011,678 | B2 | 3/2006 | Tenerz et al. |
| 7,025,741 | B2 | 4/2006 | Cull |
| 7,025,746 | B2 | 4/2006 | Tal |
| 7,037,329 | B2 | 5/2006 | Martin |
| 7,056,294 | B2 | 6/2006 | Khairkhahan et al. |
| 7,056,320 | B2 | 6/2006 | Utley et al. |
| 7,056,325 | B1 | 6/2006 | Makower et al. |
| 7,077,860 | B2 | 7/2006 | Yan et al. |
| 7,083,631 | B2 | 8/2006 | Houser et al. |
| 7,108,701 | B2 | 9/2006 | Evens et al. |
| 7,115,136 | B2 | 10/2006 | Park et al. |
| 7,118,546 | B2 | 10/2006 | Blatter |
| 7,128,750 | B1 | 10/2006 | Stergiopulos |
| 7,175,644 | B2 | 2/2007 | Cooper et al. |
| 7,182,771 | B1 | 2/2007 | Houser et al. |
| 7,235,095 | B2 | 6/2007 | Haverkost et al. |
| 7,294,115 | B1 | 11/2007 | Wilk |
| 7,316,706 | B2 | 1/2008 | Bloom et al. |
| 7,317,951 | B2 | 1/2008 | Schneider et al. |
| 7,318,804 | B2 | 1/2008 | Weitzel et al. |
| 7,326,221 | B2 | 2/2008 | Sakamoto et al. |
| 7,331,985 | B2 | 2/2008 | Thompson et al. |
| 7,335,220 | B2 | 2/2008 | Khosravi et al. |
| 7,351,247 | B2 | 4/2008 | Kupiecki et al. |
| 7,361,181 | B2 | 4/2008 | Hindrichs et al. |
| 7,374,567 | B2 | 5/2008 | Heuser |
| D581,054 | S | 11/2008 | Moore |
| 7,462,162 | B2 | 12/2008 | Phan et al. |
| 7,476,200 | B2 | 1/2009 | Tal |
| 7,530,963 | B2 | 5/2009 | Albright |
| 7,563,277 | B2 | 7/2009 | Case et al. |
| 7,623,926 | B2 | 11/2009 | Rossing et al. |
| 7,625,593 | B2 | 12/2009 | Mandrusov et al. |
| 7,628,768 | B2 | 12/2009 | Faul et al. |
| D612,499 | S | 3/2010 | Ondracek et al. |
| 7,691,110 | B2 | 4/2010 | Secrest et al. |
| 7,699,863 | B2 | 4/2010 | Marco et al. |
| 7,717,899 | B2 | 5/2010 | Bowe et al. |
| 7,722,549 | B2 | 5/2010 | Nakao |
| 7,722,665 | B2 | 5/2010 | Anwar et al. |
| 7,744,621 | B2 | 6/2010 | Paul et al. |
| 7,794,495 | B2 | 9/2010 | Gale et al. |
| 7,807,191 | B2 | 10/2010 | Iyer et al. |
| 7,815,590 | B2 | 10/2010 | Cooper |
| 7,815,656 | B2 | 10/2010 | Rust et al. |
| 7,815,852 | B2 | 10/2010 | Sternby |
| 7,828,814 | B2 | 11/2010 | Brenneman et al. |
| 7,846,179 | B2 | 12/2010 | Belef et al. |
| 7,846,194 | B2 | 12/2010 | Hartley et al. |
| 7,850,705 | B2 | 12/2010 | Bachinski et al. |
| 7,867,547 | B2 | 1/2011 | Tochterman et al. |
| 7,879,367 | B2 | 2/2011 | Heublein et al. |
| 7,892,246 | B2 | 2/2011 | Akin et al. |
| 7,892,247 | B2 | 2/2011 | Conston et al. |
| 7,923,022 | B2 | 4/2011 | Wang et al. |
| 7,951,194 | B2 | 5/2011 | Gueriguian et al. |
| 7,959,603 | B2 | 6/2011 | Wahr et al. |
| 7,964,210 | B2 | 6/2011 | Wang et al. |
| 7,967,769 | B2 | 6/2011 | Faul et al. |
| 7,972,346 | B2 | 7/2011 | Bachmann et al. |

(56)  References Cited

U.S. PATENT DOCUMENTS

| | | |
|---|---|---|
| 8,002,821 B2 | 8/2011 | Stinson |
| 8,016,782 B2 | 9/2011 | Brenneman et al. |
| 8,029,470 B2 | 10/2011 | Whiting et al. |
| 8,048,150 B2 | 11/2011 | Weber et al. |
| 8,052,751 B2 | 11/2011 | Aklog et al. |
| 8,057,534 B2 | 11/2011 | Boismier et al. |
| 8,070,708 B2 | 12/2011 | Rottenberg et al. |
| 8,088,171 B2 | 1/2012 | Brenneman |
| 8,089,029 B2 | 1/2012 | Flanagan |
| 8,091,556 B2 | 1/2012 | Keren et al. |
| 8,128,689 B2 | 3/2012 | Weber et al. |
| 8,152,773 B2 | 4/2012 | Albrecht et al. |
| 8,182,527 B2 | 5/2012 | Llanos et al. |
| 8,214,015 B2 | 7/2012 | Macaulay et al. |
| 8,221,495 B2 | 7/2012 | Shrivastava et al. |
| 8,226,592 B2 | 7/2012 | Brenneman et al. |
| D665,500 S | 8/2012 | Martin et al. |
| 8,282,591 B2 | 10/2012 | Khan et al. |
| 8,308,682 B2 | 11/2012 | Kramer et al. |
| 8,357,193 B2 | 1/2013 | Phan et al. |
| 8,376,979 B2 | 2/2013 | Kapadia |
| 8,382,697 B2 | 2/2013 | Brenneman et al. |
| D679,015 S | 3/2013 | Nakaji |
| 8,409,167 B2 | 4/2013 | Roschak |
| 8,500,697 B2 | 8/2013 | Kurth et al. |
| 8,506,984 B2 | 8/2013 | Cook et al. |
| 8,518,062 B2 | 8/2013 | Cole et al. |
| 8,518,662 B2 | 8/2013 | Ritzen et al. |
| 8,545,552 B2 | 10/2013 | Garrison et al. |
| 8,641,724 B2 | 2/2014 | Brenneman et al. |
| 8,657,790 B2 | 2/2014 | Tal et al. |
| 8,696,611 B2 | 4/2014 | Nitzan et al. |
| D705,427 S | 5/2014 | Jagger et al. |
| 8,768,487 B2 | 7/2014 | Farnan et al. |
| 8,784,860 B2 | 7/2014 | Falotico et al. |
| 8,882,830 B2 | 11/2014 | Cartledge et al. |
| 8,920,449 B2 | 12/2014 | Wilkinson |
| 8,926,545 B2 | 1/2015 | Brenneman et al. |
| 8,932,341 B2 | 1/2015 | Brenneman |
| D723,166 S | 2/2015 | Igaki et al. |
| 8,951,223 B2 | 2/2015 | McNamara et al. |
| 8,951,276 B2 | 2/2015 | Kellerman et al. |
| 9,005,155 B2 | 4/2015 | Sugimoto |
| 9,044,588 B2 | 6/2015 | Conn |
| 9,061,115 B2 | 6/2015 | Ward et al. |
| 9,067,050 B2 | 6/2015 | Gallagher et al. |
| 9,198,756 B2 | 12/2015 | Aklog et al. |
| 9,232,997 B2 | 1/2016 | Sugimoto et al. |
| 9,277,995 B2 | 3/2016 | Celermajer et al. |
| 9,345,485 B2 | 5/2016 | Dakin et al. |
| 9,345,858 B2 | 5/2016 | Flaherty et al. |
| 9,439,746 B2 | 9/2016 | Bell et al. |
| 9,456,812 B2 | 10/2016 | Finch et al. |
| 9,550,022 B2 | 1/2017 | Brenneman et al. |
| 9,649,480 B2 | 5/2017 | Sugimoto et al. |
| 9,681,948 B2 | 6/2017 | Levi et al. |
| 9,693,800 B2 | 7/2017 | Aman et al. |
| 9,775,636 B2 | 10/2017 | Fazio et al. |
| 9,789,294 B2 | 10/2017 | Taft et al. |
| 9,814,483 B2 | 11/2017 | Vardi |
| 9,827,404 B2 | 11/2017 | Nance et al. |
| 9,839,517 B2 | 12/2017 | Centola et al. |
| 9,872,981 B2 | 1/2018 | Sparks et al. |
| 9,980,815 B2 | 5/2018 | Nitzan et al. |
| 10,039,905 B1 | 8/2018 | Taft et al. |
| 10,076,403 B1 | 9/2018 | Eigler et al. |
| 10,092,215 B2 | 10/2018 | Salamini et al. |
| 10,130,371 B2 | 11/2018 | Dehdashtian et al. |
| 10,207,087 B2 | 2/2019 | Keren et al. |
| 10,272,230 B2 | 4/2019 | Malek et al. |
| 10,292,690 B2 | 5/2019 | Celermajer et al. |
| 10,327,746 B2 | 6/2019 | Glimsdale et al. |
| 10,413,284 B2 | 9/2019 | McNamara et al. |
| 10,426,482 B2 | 10/2019 | Rafiee et al. |
| 10,426,497 B2 | 10/2019 | Chou et al. |

| | | |
|---|---|---|
| 10,433,851 B2 | 10/2019 | Adams et al. |
| 10,456,259 B2 | 10/2019 | Subramanian et al. |
| 10,543,113 B2 | 1/2020 | Vong et al. |
| 10,561,423 B2 | 2/2020 | Sharma |
| 10,565,835 B2 | 2/2020 | Harrington et al. |
| 10,568,751 B2 | 2/2020 | McNamara |
| 10,595,999 B2 | 3/2020 | Vettukattil et al. |
| 10,709,451 B2 | 7/2020 | Gronberg et al. |
| 10,835,394 B2 | 11/2020 | Nae et al. |
| 10,898,698 B1 | 1/2021 | Eigler et al. |
| 10,912,585 B2 | 2/2021 | Kleyman |
| 10,925,731 B2 | 2/2021 | Bishop et al. |
| 10,925,756 B2 | 2/2021 | Perszyk |
| 10,940,296 B2 | 3/2021 | Keren |
| 11,135,054 B2 | 10/2021 | Nitzan et al. |
| 11,135,410 B2 | 10/2021 | Finch et al. |
| 11,234,702 B1 | 2/2022 | Eigler et al. |
| 11,291,807 B2 | 4/2022 | Eigler et al. |
| 11,298,117 B2 | 4/2022 | Hariton et al. |
| 11,304,698 B2 | 4/2022 | Sharma |
| 11,395,644 B2 | 7/2022 | Alanbaei |
| 11,420,034 B2 | 8/2022 | Solomon et al. |
| 2001/0000041 A1 | 3/2001 | Selmon et al. |
| 2001/0025643 A1 | 10/2001 | Foley |
| 2001/0035183 A1 | 11/2001 | Sexton et al. |
| 2001/0045698 A1 | 11/2001 | Lo |
| 2001/0047165 A1 | 11/2001 | Makower et al. |
| 2002/0013616 A1 | 1/2002 | Carter et al. |
| 2002/0029079 A1 | 3/2002 | Kim et al. |
| 2002/0062146 A1 | 5/2002 | Makower et al. |
| 2002/0128546 A1 | 9/2002 | Silver |
| 2002/0138009 A1 | 9/2002 | Brockway et al. |
| 2002/0169466 A1 | 11/2002 | Peterson et al. |
| 2002/0193751 A1 | 12/2002 | Theeuwes et al. |
| 2002/0198501 A1 | 12/2002 | Kumar et al. |
| 2003/0017150 A1 | 1/2003 | Torphy |
| 2003/0060876 A1 | 3/2003 | Loshakove et al. |
| 2003/0065345 A1 | 4/2003 | Weadock |
| 2003/0181928 A1 | 9/2003 | Vidlund et al. |
| 2003/0225425 A1 | 12/2003 | Kupiecki et al. |
| 2004/0064081 A1 | 4/2004 | Stanish |
| 2004/0082738 A1 | 4/2004 | Dolle et al. |
| 2004/0087997 A1 | 5/2004 | Brenneman |
| 2004/0092879 A1 | 5/2004 | Kraus et al. |
| 2004/0098105 A1 | 5/2004 | Stinson et al. |
| 2004/0158143 A1 | 8/2004 | Flaherty et al. |
| 2004/0215168 A1 | 10/2004 | Verrier et al. |
| 2004/0215220 A1 | 10/2004 | Dolan et al. |
| 2004/0215323 A1 | 10/2004 | Stiger |
| 2004/0230156 A1 | 11/2004 | Schreck et al. |
| 2004/0260318 A1 | 12/2004 | Hunter et al. |
| 2005/0021085 A1 | 1/2005 | Abrams et al. |
| 2005/0033239 A1 | 2/2005 | Argentine |
| 2005/0038501 A1 | 2/2005 | Moore et al. |
| 2005/0043708 A1 | 2/2005 | Gleeson et al. |
| 2005/0049675 A1 | 3/2005 | Wallace |
| 2005/0060041 A1 | 3/2005 | Phan et al. |
| 2005/0065469 A1 | 3/2005 | Tal |
| 2005/0075655 A1 | 4/2005 | Bumbalough et al. |
| 2005/0075656 A1 | 4/2005 | Beaupre |
| 2005/0082226 A1 | 4/2005 | Bene et al. |
| 2005/0107723 A1 | 5/2005 | Wehman et al. |
| 2005/0149096 A1 | 7/2005 | Hilal et al. |
| 2005/0165344 A1 | 7/2005 | Dobak |
| 2005/0228402 A1 | 10/2005 | Hofmann |
| 2005/0249770 A1 | 11/2005 | Hunter |
| 2005/0249776 A1 | 11/2005 | Chen et al. |
| 2005/0267490 A1 | 12/2005 | Secrest et al. |
| 2005/0272806 A1 | 12/2005 | Falotico et al. |
| 2005/0277965 A1 | 12/2005 | Brenneman et al. |
| 2006/0020324 A1 | 1/2006 | Schmid et al. |
| 2006/0024359 A1 | 2/2006 | Walker et al. |
| 2006/0034466 A1 | 2/2006 | Form et al. |
| 2006/0041270 A1 | 2/2006 | Lenker et al. |
| 2006/0074398 A1 | 4/2006 | Whiting et al. |
| 2006/0111704 A1 | 5/2006 | Brenneman et al. |
| 2006/0130591 A1 | 6/2006 | Perkins |
| 2006/0130767 A1 | 6/2006 | Herchen |
| 2006/0182536 A1 | 8/2006 | Rice et al. |

(56)　　　　References Cited

U.S. PATENT DOCUMENTS

| | | |
|---|---|---|
| 2006/0198869 A1 | 9/2006 | Furst et al. |
| 2006/0241342 A1 | 10/2006 | Macaulay et al. |
| 2006/0264801 A1 | 11/2006 | Bolling et al. |
| 2006/0265042 A1 | 11/2006 | Catanese et al. |
| 2006/0271196 A1 | 11/2006 | Saal et al. |
| 2006/0293701 A1 | 12/2006 | Ainsworth et al. |
| 2007/0010780 A1 | 1/2007 | Vijay |
| 2007/0021730 A1 | 1/2007 | Flaherty et al. |
| 2007/0083258 A1 | 4/2007 | Falotico et al. |
| 2007/0173787 A1 | 7/2007 | Huang et al. |
| 2007/0179426 A1 | 8/2007 | Selden |
| 2007/0213750 A1 | 9/2007 | Weadock |
| 2008/0021485 A1 | 1/2008 | Catanese et al. |
| 2008/0027532 A1 | 1/2008 | Boylan et al. |
| 2008/0051883 A1 | 2/2008 | Llanos et al. |
| 2008/0071178 A1 | 3/2008 | Greenland et al. |
| 2008/0091264 A1 | 4/2008 | Machold et al. |
| 2008/0109069 A1 | 5/2008 | Coleman et al. |
| 2008/0161904 A1 | 7/2008 | Heuser et al. |
| 2008/0167595 A1 | 7/2008 | Porter et al. |
| 2008/0234842 A1 | 9/2008 | Zhang |
| 2008/0306359 A1 | 12/2008 | Zdeblick et al. |
| 2009/0005656 A1 | 1/2009 | Najafi et al. |
| 2009/0105654 A1 | 4/2009 | Kurth et al. |
| 2009/0125097 A1 | 5/2009 | Bruszewski et al. |
| 2009/0143713 A1 | 6/2009 | Van Dam et al. |
| 2009/0149947 A1 | 6/2009 | Frohwitter |
| 2009/0187116 A1 | 7/2009 | Noishiki et al. |
| 2009/0234293 A1 | 9/2009 | Albrecht et al. |
| 2009/0281379 A1 | 11/2009 | Binmoeller et al. |
| 2010/0016797 A1 | 1/2010 | Rockrohr |
| 2010/0022940 A1 | 1/2010 | Thompson |
| 2010/0030321 A1 | 2/2010 | Mach |
| 2010/0106171 A1 | 4/2010 | Arepally et al. |
| 2010/0198041 A1 | 8/2010 | Christian et al. |
| 2010/0217382 A1 | 8/2010 | Chau et al. |
| 2010/0298930 A1 | 11/2010 | Orlov |
| 2011/0096036 A1 | 4/2011 | McIntosh et al. |
| 2011/0106118 A1 | 5/2011 | Son et al. |
| 2011/0251482 A1 | 10/2011 | Kellerman et al. |
| 2011/0306916 A1 | 12/2011 | Nitzan et al. |
| 2012/0029598 A1 | 2/2012 | Zhao |
| 2012/0041544 A1 | 2/2012 | Wolf |
| 2012/0053686 A1 | 3/2012 | McNamara et al. |
| 2012/0089116 A9 | 4/2012 | Roschak |
| 2012/0108986 A1 | 5/2012 | Beasley et al. |
| 2012/0143141 A1 | 6/2012 | Verkaik et al. |
| 2012/0265229 A1 | 10/2012 | Rottenberg et al. |
| 2012/0265296 A1 | 10/2012 | McNamara et al. |
| 2013/0022214 A1 | 1/2013 | Dickins et al. |
| 2013/0030521 A1 | 1/2013 | Nitzan et al. |
| 2013/0046152 A1 | 2/2013 | Najafi et al. |
| 2013/0178784 A1 | 7/2013 | McNamara et al. |
| 2013/0225997 A1 | 8/2013 | Dillard et al. |
| 2013/0253342 A1 | 9/2013 | Griswold et al. |
| 2013/0281988 A1 | 10/2013 | Magnin et al. |
| 2014/0094836 A1 | 4/2014 | Feng et al. |
| 2014/0180222 A1* | 6/2014 | Flaherty ............ A61M 25/0108 604/272 |
| 2014/0183828 A1 | 7/2014 | Xu et al. |
| 2014/0203939 A1 | 7/2014 | Harrington et al. |
| 2014/0222040 A1 | 8/2014 | Park et al. |
| 2014/0276395 A1 | 9/2014 | Wilson et al. |
| 2014/0277054 A1 | 9/2014 | McNamara et al. |
| 2014/0278442 A1 | 9/2014 | Hong et al. |
| 2014/0350523 A1 | 11/2014 | Dehdashtian et al. |
| 2015/0119796 A1 | 4/2015 | Finch |
| 2015/0148731 A1 | 5/2015 | McNamara et al. |
| 2015/0151101 A1 | 6/2015 | Bonnette et al. |
| 2015/0238729 A1 | 8/2015 | Jenson et al. |
| 2016/0015935 A1 | 1/2016 | Chan et al. |
| 2016/0022293 A1 | 1/2016 | Dubrul et al. |
| 2016/0022970 A1 | 1/2016 | Forcucci et al. |
| 2016/0045165 A1 | 2/2016 | Braido et al. |
| 2016/0058452 A1 | 3/2016 | Brenneman et al. |
| 2016/0120550 A1 | 5/2016 | McNamara et al. |
| 2016/0151615 A1 | 6/2016 | Overtoom |
| 2016/0220357 A1 | 8/2016 | Anand et al. |
| 2016/0270810 A1 | 9/2016 | Vardi et al. |
| 2016/0296317 A1 | 10/2016 | Timmermans et al. |
| 2016/0323977 A1 | 11/2016 | Sun et al. |
| 2016/0331468 A1 | 11/2016 | Lee et al. |
| 2016/0338823 A1 | 11/2016 | Akingba |
| 2017/0079671 A1* | 3/2017 | Morero ............ A61M 25/0082 |
| 2017/0090865 A1 | 3/2017 | Armstrong-Muntner et al. |
| 2017/0105839 A1 | 4/2017 | Subramanian et al. |
| 2017/0106176 A1 | 4/2017 | Taft et al. |
| 2017/0113026 A1 | 4/2017 | Finch |
| 2017/0128705 A1 | 5/2017 | Forcucci et al. |
| 2017/0196565 A1 | 7/2017 | Tuseth et al. |
| 2017/0258585 A1 | 9/2017 | Marquez et al. |
| 2017/0303959 A1 | 10/2017 | Feng et al. |
| 2017/0319823 A1 | 11/2017 | Yacoby et al. |
| 2017/0340460 A1 | 11/2017 | Rosen et al. |
| 2017/0367728 A1* | 12/2017 | Qu ..................... A61B 17/3417 |
| 2018/0035971 A1 | 2/2018 | Brenner et al. |
| 2018/0140444 A1 | 5/2018 | Neuss et al. |
| 2018/0177516 A1 | 6/2018 | Vardi et al. |
| 2018/0185153 A1 | 7/2018 | Bishop et al. |
| 2018/0207412 A1 | 7/2018 | Malek et al. |
| 2018/0214269 A1 | 8/2018 | Wilson et al. |
| 2018/0243071 A1 | 8/2018 | Eigler et al. |
| 2018/0256865 A1 | 9/2018 | Finch et al. |
| 2019/0008628 A1 | 1/2019 | Eigler et al. |
| 2019/0083228 A1 | 3/2019 | Dickinson et al. |
| 2019/0134350 A1 | 5/2019 | Crisco et al. |
| 2019/0269392 A1 | 9/2019 | Celermajer et al. |
| 2019/0298909 A1 | 10/2019 | Cully et al. |
| 2019/0336339 A1 | 11/2019 | Reo et al. |
| 2019/0351210 A1 | 11/2019 | Solomon et al. |
| 2020/0054867 A1 | 2/2020 | Schwartz et al. |
| 2020/0085600 A1 | 3/2020 | Schwartz et al. |
| 2020/0101270 A1 | 4/2020 | Sutherland |
| 2020/0170662 A1 | 6/2020 | Vardi et al. |
| 2020/0187945 A1 | 6/2020 | Rowe et al. |
| 2020/0230362 A1 | 7/2020 | Basude |
| 2020/0254228 A1 | 8/2020 | Taft et al. |
| 2020/0261704 A1 | 8/2020 | Wang et al. |
| 2020/0289196 A1 | 9/2020 | Arevalos et al. |
| 2020/0315599 A1 | 10/2020 | Nae et al. |
| 2020/0368505 A1 | 11/2020 | Nae et al. |
| 2020/0391016 A1 | 12/2020 | Passman et al. |
| 2021/0000581 A9 | 1/2021 | Eigler et al. |
| 2021/0007790 A1 | 1/2021 | Takahashi et al. |
| 2021/0007791 A1 | 1/2021 | Takahashi et al. |
| 2021/0007800 A1 | 1/2021 | Takahashi et al. |
| 2021/0022855 A1 | 1/2021 | Tegels et al. |
| 2021/0045691 A1 | 2/2021 | Zou et al. |
| 2021/0052877 A1 | 2/2021 | Muldoon et al. |
| 2021/0059650 A1 | 3/2021 | Eidenschink et al. |
| 2021/0077186 A1 | 3/2021 | Pate et al. |
| 2021/0085935 A1 | 3/2021 | Fahey et al. |
| 2021/0092522 A1 | 3/2021 | Draper et al. |
| 2021/0113824 A1 | 4/2021 | Chng et al. |
| 2021/0121179 A1 | 4/2021 | Ben-David et al. |
| 2021/0137635 A1 | 5/2021 | Gomez et al. |
| 2021/0153776 A1 | 5/2021 | Minar et al. |
| 2021/0161637 A1 | 6/2021 | Eigler et al. |
| 2021/0177508 A1 | 6/2021 | Kellerman |
| 2021/0213269 A1 | 7/2021 | Venskytis et al. |
| 2021/0236138 A1 | 8/2021 | Perszyk et al. |
| 2021/0259671 A1 | 8/2021 | DiCicco et al. |
| 2021/0290214 A1 | 9/2021 | Cole et al. |
| 2021/0338990 A1 | 11/2021 | Eigler et al. |
| 2021/0361238 A1 | 11/2021 | Bak-Boychuk et al. |
| 2021/0369321 A1 | 12/2021 | Yang et al. |
| 2021/0401494 A1 | 12/2021 | Passman et al. |
| 2022/0001154 A1 | 1/2022 | Rowe et al. |
| 2022/0008014 A1 | 1/2022 | Rowe et al. |
| 2022/0031327 A1 | 2/2022 | Manash et al. |
| 2022/0039667 A1 | 2/2022 | Schmitt et al. |
| 2022/0039671 A1 | 2/2022 | Fahey |
| 2022/0039833 A1 | 2/2022 | Thai et al. |
| 2022/0088355 A1 | 3/2022 | Rabito et al. |

(56) References Cited

U.S. PATENT DOCUMENTS

| | | |
|---|---|---|
| 2022/0096087 A1 | 3/2022 | Valdez |
| 2022/0110679 A1 | 4/2022 | Wang et al. |
| 2022/0142652 A1 | 5/2022 | Alexander et al. |
| 2022/0151784 A1 | 5/2022 | Eigler et al. |
| 2022/0168015 A1 | 6/2022 | Murray et al. |
| 2022/0177206 A1* | 6/2022 | Wendle .............. B65D 63/1027 |
| 2022/0184356 A1 | 6/2022 | Nae et al. |
| 2022/0202443 A1 | 6/2022 | Thai et al. |
| 2022/0203077 A1 | 6/2022 | Folan |
| 2022/0203078 A1 | 6/2022 | May |
| 2022/0211380 A1 | 7/2022 | Pate |
| 2022/0218352 A1 | 7/2022 | O'Halloran et al. |
| 2022/0218964 A1 | 7/2022 | Fahey et al. |
| 2022/0241564 A1 | 8/2022 | Shang et al. |
| 2022/0241565 A1 | 8/2022 | Nae et al. |
| 2022/0249285 A1 | 8/2022 | Chang et al. |
| 2022/0257904 A1 | 8/2022 | Passman et al. |
| 2022/0273279 A1 | 9/2022 | Valdez et al. |
| 2022/0280160 A1 | 9/2022 | Sharma |
| 2022/0280760 A1 | 9/2022 | Thai et al. |
| 2022/0296865 A1 | 9/2022 | Rafiee et al. |
| 2022/0313234 A1 | 10/2022 | McNamara et al. |
| 2022/0323012 A1 | 10/2022 | Pool et al. |
| 2022/0323196 A1 | 10/2022 | Rafiee et al. |
| 2022/0346936 A1 | 11/2022 | Scutti et al. |
| 2022/0347446 A1 | 11/2022 | Fahey et al. |
| 2022/0370120 A1 | 11/2022 | Yang et al. |
| 2022/0379100 A1 | 12/2022 | Gutierrez et al. |
| 2022/0387009 A1 | 12/2022 | Bukhdruker et al. |
| 2023/0099410 A1 | 3/2023 | Primeaux |
| 2023/0165672 A1 | 6/2023 | Fahey et al. |
| 2023/0181214 A1 | 6/2023 | Vardi et al. |
| 2023/0191093 A1 | 6/2023 | Nae et al. |
| 2023/0233255 A1 | 7/2023 | Takahashi |
| 2023/0263949 A1 | 8/2023 | Passman et al. |
| 2023/0285133 A1 | 9/2023 | Eigler et al. |
| 2023/0330398 A1 | 10/2023 | Nae et al. |
| 2023/0371902 A1 | 11/2023 | Valdez |
| 2023/0389811 A1 | 12/2023 | Valdez |
| 2023/0404659 A1 | 12/2023 | Akerele-Ale et al. |
| 2024/0000404 A1 | 1/2024 | Robertson et al. |

FOREIGN PATENT DOCUMENTS

| | | |
|---|---|---|
| CN | 113367839 A | 9/2021 |
| CN | 113397762 A | 9/2021 |
| JP | H11513577 A | 11/1999 |
| KR | 20200145957 A | 12/2020 |
| WO | WO-2000015147 A1 | 3/2000 |
| WO | 2005006963 A2 | 1/2005 |
| WO | 2014150106 A1 | 9/2014 |
| WO | 2015052235 A1 | 4/2015 |
| WO | 2019035993 A1 | 2/2019 |
| WO | 2020215090 A1 | 10/2020 |
| WO | 2020232384 A1 | 11/2020 |
| WO | 2021091566 A1 | 5/2021 |
| WO | 2022031317 A1 | 2/2022 |
| WO | 2022060630 A1 | 3/2022 |
| WO | 2022071179 A1 | 4/2022 |
| WO | 2022133070 A1 | 6/2022 |
| WO | 2022169865 A1 | 8/2022 |
| WO | 2022177737 A1 | 8/2022 |
| WO | 2022197454 A1 | 9/2022 |
| WO | 2022197455 A1 | 9/2022 |
| WO | 2022232133 A1 | 11/2022 |
| WO | 2022246158 A1 | 11/2022 |
| WO | 2022246166 A1 | 11/2022 |
| WO | 2022271473 A1 | 12/2022 |
| WO | 2023022883 A1 | 2/2023 |
| WO | 2023027926 A1 | 3/2023 |
| WO | 2023079498 A1 | 5/2023 |
| WO | 2023081127 A1 | 5/2023 |
| WO | 2023081129 A1 | 5/2023 |
| WO | 2023154235 A1 | 8/2023 |
| WO | 2023154308 A1 | 8/2023 |
| WO | 2023172435 A1 | 9/2023 |
| WO | 2023172436 A1 | 9/2023 |
| WO | 2023196243 A1 | 10/2023 |
| WO | 2023239784 A1 | 12/2023 |
| WO | 2023239785 A1 | 12/2023 |
| WO | 2023239788 A2 | 12/2023 |
| WO | 2024076579 A1 | 4/2024 |

OTHER PUBLICATIONS

Kong, et al.—Creation Of An Intra-atrial Communication With a New Amplatzer Shunt Prosthesis, Catheterization and Cardiovascular Interventions 56:267-271 (2002).

P.K. Kong, et al., Title: Unroofed Coronary Sinus and Persistent Left Superior Vena Cava, The European Society of Cardiology, 2006, pp. 398401.

Ruebben et al., "Arteriovenous fistulas induced by femoral arterial catheterization: percuntaneous treatment," Radiology, 209:729, 1998.

Vandhana Scheller, et al., Title: Coronary Sinus to Left Atrial Communication, Case Report in Medicine, Ohio Heart and Vascular Center, vol. 2009, Article ID 790715, pp. 13.

Yeh Chao-Chi et al: "Fabrication of a flexible wireless pressure sensor for intravascular blood pressure monitoring", Microelectronic Engineering, vol. 213, Apr. 11, 2019 (Apr. 11, 2019), pp. 55-61, XP085679189, ISSN: 0167-9317, DOI; 10.1016/J.MEE. 2019.04.009 p. 56 section 2. Working principle and device design Fig, I(a).

Bechtold C., et al., "Method for Fabricating Miniaturized NiTi Self-Expandable Thin Film Devices with Increased Radiopacity", Shape Memory and Superelasticity, 2016, vol. 2, pp. 391-398.

* cited by examiner

1600

ADVANCE MEDICAL IMPLANT DELIVERY CATHETER
ALONG GUIDE WIRE INTO VESSEL, MEDICAL IMPLANT
DELIVERY SYSTEM COMPRISING OUTER DELIVERY
CATHETER, MEDICAL IMPLANT DELIVERY CATHETER
EXTENDING THROUGH LUMEN OF OUTER DELIVERY
CATHETER, AND PUNCTURE NEEDLE EXTENDING
THROUGH LUMEN OF MEDICAL IMPLANT DELIVERY
CATHETER
1602

ADVANCE MEDICAL IMPLANT DELIVERY
CATHETER THROUGH SIDE OUTLET OPENING OF OUTER
DELIVERY CATHETER
1604

PIERCE TISSUE AT TARGET TISSUE SITE TO FORM
OPENING IN TISSUE USING PUNCTURE COMPONENT
EXTENDING THROUGH DISTAL OUTLET OPENING OF
MEDICAL IMPLANT DELIVERY CATHETER
1606

EXTEND DISTAL PORTION OF MEDICAL IMPLANT
DELIVERY CATHETER THROUGH OPENING FORMED IN
TISSUE
1608

DEPLOY MEDICAL IMPLANT DEVICE POSITIONED ON
MEDICAL IMPLANT DELIVERY CATHETER INTO OPENING
FORMED IN TISSUE
1610

ADVANCE MEDICAL IMPLANT DELIVERY SYSTEM ALONG GUIDE WIRE INTO VESSEL, MEDICAL IMPLANT DELIVERY SYSTEM COMPRISING ELONGATE HOUSING, MEDICAL IMPLANT DELIVERY CATHETER ALONGSIDE ELONGATE HOUSING, AND OUTER SHEATH AROUND ELONGATE HOUSING AND MEDICAL IMPLANT DELIVERY CATHETER      *2402*

TRANSLATE OUTER SHEATH PROXIMALLY TO RELEASE DISTAL PORTION OF MEDICAL IMPLANT DELIVERY CATHETER      *2404*

TRANSLATE MEDICAL IMPLANT DELIVERY CATHETER DISTALLY RELATIVE TO ELONGATE HOUSING      *2406*

PIERCE TISSUE AT TARGET TISSUE SITE TO FORM OPENING IN TISSUE USING PUNCTURE COMPONENT EXTENDING THROUGH DISTAL OUTLET OPENING OF MEDICAL IMPLANT DELIVERY CATHETER      *2408*

INSERT DISTAL PORTION OF MEDICAL IMPLANT DELIVERY CATHETER THROUGH OPENING FORMED IN TISSUE      *2410*

DEPLOY MEDICAL IMPLANT DEVICE POSITIONED ON MEDICAL IMPLANT DELIVERY CATHETER INTO OPENING FORMED IN TISSUE      *2412*

*FIG. 25*

TRANSCATHETER MEDICAL IMPLANT DELIVERY

CROSS REFERENCE TO RELATED APPLICATIONS

This application is a continuation of International Patent Application No. PCT/US2020/059304, filed Nov. 6, 2020, entitled "TRANSCATHETER MEDICAL IMPLANT DELIVERY", which claims the benefit of U.S. Provisional Patent Application No. 62/935,214, filed Nov. 14, 2019, entitled "TRANSCATHETER MEDICAL IMPLANT DELIVERY", the disclosures of each of which are hereby expressly incorporated by reference herein in its entirety for all purposes.

BACKGROUND

Field

The present disclosure generally relates to the field of transcatheter delivery of medical implant devices and/or therapies.

Description of Related Art

Transcatheter delivery of medical implant devices and/or therapies to a target vessel, channel, chamber and/or organ can be performed to treat various ailments. Delivery of medical implant devices and/or therapies to the heart can be performed to address various heart conditions, including elevated pressure in the left atrium.

SUMMARY

Described herein are systems and methods for providing minimally invasive transcatheter delivery of medical implant devices and/or therapies, including delivery of a medical implant device to the left atrial wall for alleviating elevated left atrial pressure.

In some implementations, a medical implant delivery system can comprise a puncture needle, a medical implant delivery catheter, a medical implant device, and an outer delivery catheter. The puncture needle can comprise an elongate portion and a puncture component associated with a distal end of the elongate portion, the puncture component being configured to pierce and form an opening in a target tissue wall. The medical implant delivery catheter can comprise a puncture needle lumen, the puncture needle being configured to be advanced through the puncture needle lumen, the puncture component being configured to be extended through a puncture needle outlet opening associated with a distal portion of the medical implant delivery catheter. The medical implant device can be positioned on the medical implant delivery catheter. The outer delivery catheter can comprise a medical implant delivery lumen, the medical implant delivery catheter being configured to be advanced through the medical implant delivery lumen, the distal portion of the medical implant delivery catheter being configured to be received within the medical implant delivery lumen and extended through a side outlet opening associated with a distal portion of the outer delivery catheter.

In some embodiments, the medical implant delivery system can comprise a puncture needle sheath configured to be passed through the puncture needle lumen, wherein the puncture needle is configured to be passed through a lumen of the puncture needle sheath. A radially expandable member can be associated with a distal portion of the puncture needle sheath, wherein the radially expandable member is configured to be positioned within the opening formed in the target tissue wall and to enlarge the opening when the radially expandable member is in an expanded configuration. In some embodiments, the medical implant delivery system can comprise a medical implant delivery guide wire, wherein the medical implant delivery guide wire is configured to be slidably advanced through the lumen of the puncture needle sheath and to be exchangeable with the puncture needle.

In some embodiments, a distal portion of the medical implant delivery catheter is configured to be inserted into the opening formed in the target tissue wall, the distal portion comprising a predetermined diameter configured to enlarge the opening.

In some embodiments, the medical implant delivery system can comprise an outer delivery catheter guide wire, and wherein the outer delivery catheter comprises a guide wire lumen configured to receive the outer delivery catheter guide wire. In some embodiments, the outer delivery catheter guide wire lumen extends along an off-center longitudinal axis of the outer delivery catheter.

In some embodiments, a distal portion of the medical implant delivery catheter comprises a lateral cross section having a shape configured to interlock with a shape of the side outlet opening on the distal portion of the outer delivery catheter to orient the medical implant delivery catheter as the medical implant delivery catheter extends through the side outlet opening, wherein the lateral cross section extends along a lateral dimension of the distal portion of the outer delivery catheter.

In some embodiments, the medical implant delivery catheter comprises a first tapered distal portion comprising a first pre-formed curvature and the outer delivery catheter comprises a second tapered distal portion comprising a second pre-formed curvature, wherein the first curvature and the second curvature comprise the same orientation. In some embodiments, the first pre-formed curvature comprises a radius of curvature smaller than that of the second pre-formed curvature. In some embodiments, the second pre-formed curvature comprises a shape configured to conform to at least a portion of a curvature along a length of a coronary sinus. In some embodiments, the side outlet opening is on an inner edge of the second pre-formed curvature of the outer delivery catheter.

In some embodiments, the puncture needle comprises a third pre-formed curvature on a distal portion of the puncture needle. In some embodiments, the third pre-formed curvature comprises a radius of curvature smaller than that of the first pre-formed curvature of the medical implant delivery catheter.

In some embodiments, the medical implant delivery system can comprise an expandable anchor, wherein the expandable anchor and the side outlet opening are on opposing portions of the outer delivery catheter, and wherein the expandable anchor is configured to assume an expanded configuration to position the outer delivery catheter against the target tissue wall. In some embodiments, the outer delivery catheter comprises a second tapered distal portion comprising a second pre-formed curvature and wherein the anchor is on an outer edge of the second pre-formed curvature.

In some implementations, a method for delivering a medical implant device can comprise advancing a guide wire into a vessel, and advancing a medical implant delivery system along the guide wire into the vessel. The medical implant delivery system can comprise an outer delivery catheter comprising a medical implant delivery lumen, a medical implant delivery catheter comprising a medical implant delivery device positioned thereon and a puncture needle lumen extending therethrough, the medical implant delivery catheter slidably extending through the medical implant delivery lumen, and a puncture needle slidably extending through the puncture needle lumen, and a puncture component of the puncture needle extending through a distal outlet opening on a distal end of the medical implant delivery catheter. The method can comprise advancing the medical implant delivery catheter through a side outlet opening on a distal portion of the outer delivery catheter and piercing tissue at a target tissue site using the puncturing component extending through the distal outlet opening to form an opening in the tissue. A distal portion of the medical implant delivery catheter can be extended through the opening formed in the tissue; and the medical implant device positioned on the distal portion of the medical implant delivery catheter can be deployed into the opening formed in the tissue.

In some embodiments, the method can comprise inserting a radially expandable member positioned on a distal portion of a puncture needle sheath in the opening formed in the tissue, and expanding the radially expandable member to enlarge the opening, wherein the puncture needle sheath slidably extends through the puncture needle lumen, and the puncture needle slidably extends through a lumen of the puncture needle sheath.

In some embodiments, the method can comprise exchanging the puncture needle for a medical implant delivery guide wire and inserting the medical implant delivery guide wire through the lumen of the puncture needle sheath.

In some embodiments, the method can comprise inserting a distal portion of the medical implant delivery catheter into the opening formed at the target tissue site to enlarge the opening.

In some embodiments, the method can comprise orienting a distal portion of the medical implant delivery catheter within the medical implant delivery lumen and extending the distal portion through the side outlet opening, wherein orienting comprises rotating the distal portion of the medical implant delivery catheter to match a shape of a lateral cross section of the distal portion with a shape of the side outlet opening, and wherein the lateral cross section extends along a lateral dimension of the distal portion of the outer delivery catheter.

In some embodiments, the method can comprise expanding an expandable anchor on the distal portion of the outer delivery catheter to contact the expandable anchor with a wall of the vessel.

In some embodiments, positioning the guide wire into a vessel comprises positioning the guide wire transfemorally into a coronary sinus through a right atrium via an ostium of the coronary sinus. In some embodiments, piercing tissue at the target tissue site comprises piercing tissue of a left atrial wall to form the opening in the left atrial wall, and wherein deploying the medical implant device comprises deploying the medical implant device into the opening formed in the left atrial wall.

In some embodiments, a medical implant delivery system can comprise a puncture needle, a medical implant delivery catheter, a medical implant device, an elongate housing, and an outer sheath. The puncture needle can comprise an elongate portion and a puncture component at a distal end of the elongate portion, the puncture component being configured to pierce tissue to form an opening in the tissue. The medical implant delivery catheter can comprise a puncture needle lumen and the puncture needle being configured to slidably extend through the puncture needle lumen, and the puncture component being configured to extend through a puncture needle outlet opening at a distal end of the medical implant delivery catheter. The medical implant device can be carried on the medical implant delivery catheter. The elongate housing can be adjacent to and be slidable relative to the medical implant delivery catheter, wherein a distal end of the elongate housing is distal of the distal end of the medical implant delivery catheter when the medical implant delivery catheter is in a retracted configuration. The outer sheath can be around a portion of the medical implant delivery catheter and the elongate housing to maintain the medical implant delivery catheter adjacent to the elongate housing, wherein the outer sheath is slidable relative to the medical implant delivery catheter and extends over the distal end of the medical implant delivery catheter when the medical implant delivery catheter is in the retracted configuration.

In some embodiments, the elongate housing comprises a recess along at least a portion of a length of the elongate housing, a portion of the medical implant delivery catheter being received in the recess. In some embodiments, the elongate housing comprises a guide wire lumen configured to receive an elongate housing guide wire, and the distal end of the elongate housing comprises a guide wire outlet opening configured to allow extension therethrough of the elongate housing guide wire.

In some embodiments, the medical implant delivery catheter comprises a first tapered distal portion comprising a first pre-formed curvature and the elongate housing comprises a second tapered distal portion comprising a second pre-formed curvature, wherein the first pre-formed curvature and the second pre-formed curvature comprise the same orientation. In some embodiments, the first pre-formed curvature comprises a radius of curvature smaller than that of the second pre-formed curvature. In some embodiments, the second pre-formed curvature comprises a shape configured to conform to a curvature along a length of a coronary sinus.

In some embodiments, the medical implant delivery system can comprise an expandable anchor on the distal portion of the elongate housing opposite a portion of the elongate housing adjacent to the medical implant delivery catheter, the expandable anchor being configured to assume an expanded configuration to position the medical implant delivery catheter against a target tissue site. In some embodiments, the elongate housing comprises a second tapered distal portion comprising a second pre-formed curvature and the expandable anchor is on an outer edge of the second pre-formed curvature.

In some embodiments, the medical implant delivery system can comprise a puncture needle sheath slidably extending through the puncture needle lumen, and the puncture needle sheath slidably extending through the puncture needle. A radially expandable member can be on a distal portion of the puncture needle sheath, the radially expandable member being configured to enlarge the opening formed in the tissue.

In some embodiments, the puncture needle is configured to be exchangeable for a medical implant delivery guide wire.

In some implementations, a method for delivering a medical implant device can comprise positioning a guide wire into a vessel, and advancing a medical implant delivery system along the guide wire into the vessel. The medical implant delivery system can comprise an elongate housing, a medical implant delivery catheter adjacent to the elongate housing, the medical implant delivery catheter carrying a medical implant device and comprising a puncture needle lumen, a puncture needle slidably extending through the puncture needle lumen, and a puncture component of the puncture needle extending through a distal outlet opening on a distal end of the medical implant delivery catheter, and an outer sheath around the elongate housing and the medical implant delivery catheter. The method can comprise proximally sliding the outer sheath to release a distal portion of the medical implant delivery catheter, distally sliding the medical implant delivery catheter relative to the elongate housing and piercing tissue at a target tissue site to form an opening in the tissue using the puncture component extending through the distal outlet opening of the medical implant delivery catheter, extending the distal portion of the medical implant delivery catheter through the opening in the tissue, and deploying the medical implant device carried on the medical implant delivery catheter into the opening.

In some embodiments, the method can comprise positioning a radially expandable member on a distal portion of a puncture needle sheath in the opening formed in the tissue, and expanding the radially expandable member to enlarge the opening, wherein the puncture needle sheath slidably extends through the puncture needle lumen, and the puncture needle slidably extends through a lumen of the puncture needle sheath. In some embodiments, the method can comprise exchanging the puncture needle for a medical implant delivery guide wire and inserting the medical implant delivery guide wire through the lumen of the puncture needle sheath.

In some embodiments, the method can comprise inserting the distal portion of the medical implant delivery catheter into the opening formed at the target tissue site to enlarge the opening.

In some embodiments, the method can comprise expanding an expandable anchor on a distal portion of the elongate housing to contact the expandable anchor with a wall of the vessel.

In some embodiments, positioning the guide wire into the vessel comprises positioning the guide wire transfemorally into a coronary sinus through a right atrium via an ostium of the coronary sinus. In some embodiments, piercing tissue at the target tissue site comprises piercing tissue of a left atrial wall, and wherein deploying the medical implant device comprises deploying the medical implant device into the opening formed in the left atrial wall.

For purposes of summarizing the disclosure, certain aspects, advantages and novel features have been described herein. It is to be understood that not necessarily all such advantages may be achieved in accordance with any particular embodiment. Thus, the disclosed embodiments may be carried out in a manner that achieves or optimizes one advantage or group of advantages as taught herein without necessarily achieving other advantages as may be taught or suggested herein.

BRIEF DESCRIPTION OF THE DRAWINGS

Various embodiments are depicted in the accompanying drawings for illustrative purposes and should in no way be interpreted as limiting the scope of the inventions. In addition, various features of different disclosed embodiments can be combined to form additional embodiments, which are part of this disclosure. Throughout the drawings, reference numbers may be reused to indicate correspondence between reference elements. However, it should be understood that the use of similar reference numbers in connection with multiple drawings does not necessarily imply similarity between respective embodiments associated therewith. Furthermore, it should be understood that the features of the respective drawings are not necessarily drawn to scale, and the illustrated sizes thereof are presented for the purpose of illustration of inventive aspects thereof. Generally, certain of the illustrated features may be relatively smaller than as illustrated in some embodiments or configurations.

FIG. 17 is a process flow diagram of an example of a process to deploy the medical implant delivery system of FIG. 3 to deliver a medical implant device, in accordance with one or more embodiments.

7

Figure 18:
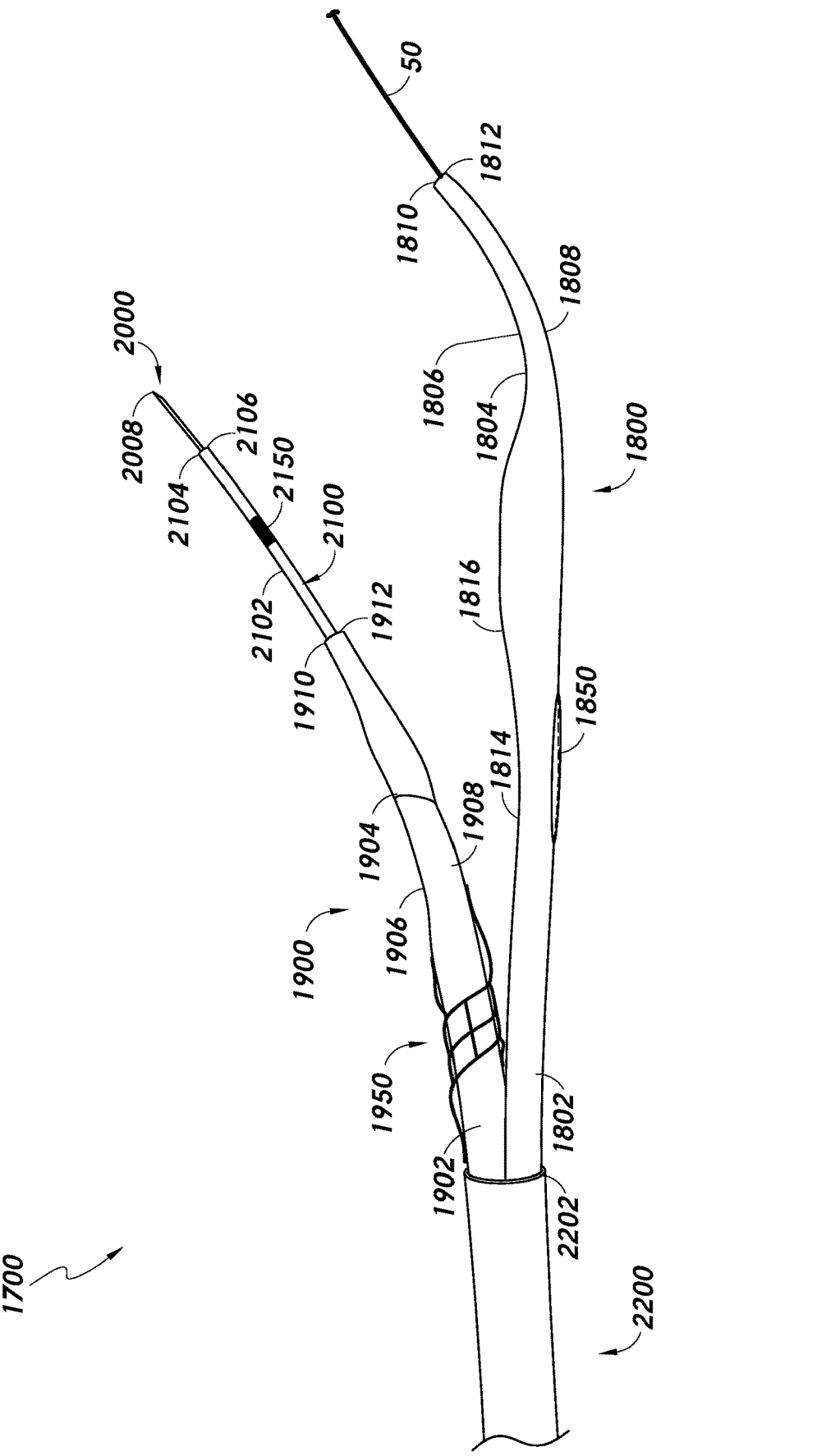
FIG. 18 is a side view of another example of a medical implant delivery system, in accordance with one or more embodiments.
Figure 19:

FIG. 19 is a side view of the medical implant delivery system of FIG. 18 comprising the puncture needle in an extended configuration, in accordance with one or more embodiments.

Figure 20:
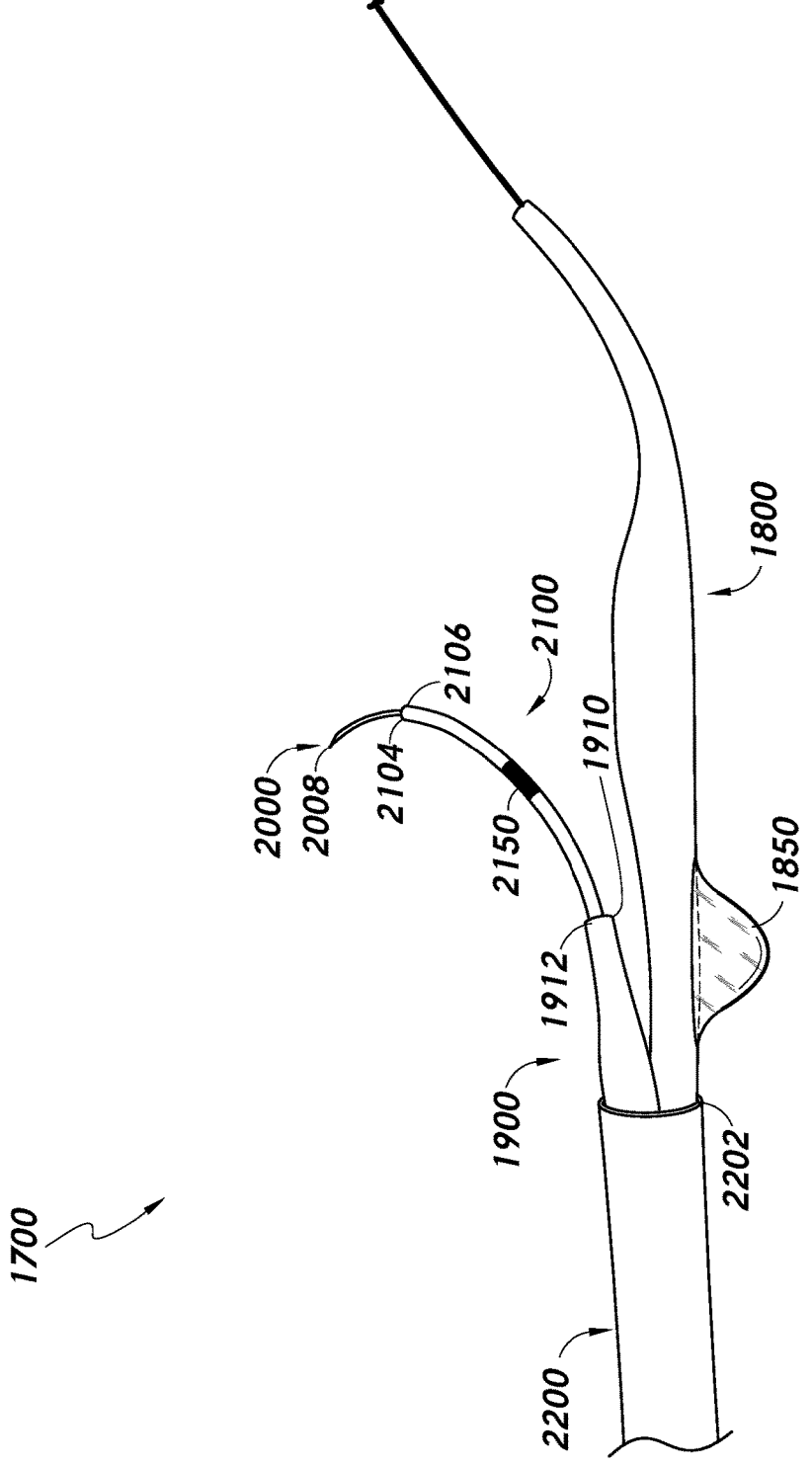

FIG. 20 is a side view of the medical implant delivery system of FIG. 18 with the outer sheath translated proximally, in accordance with one or more embodiments.

Figure 21:
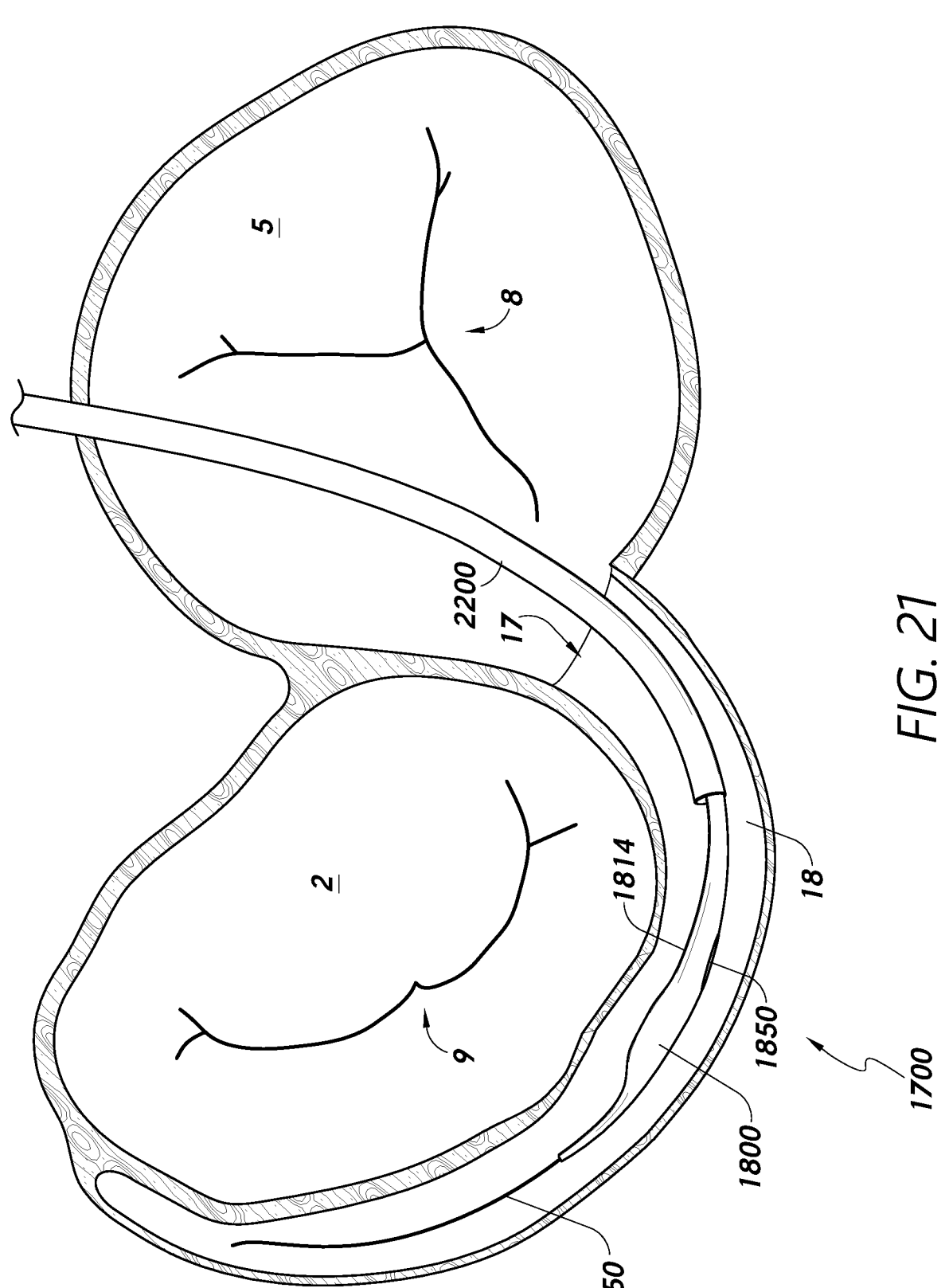

FIG. 21 shows advancement of the medical implant delivery system of FIG. 18 into the coronary sinus, in accordance with one or more embodiments.

Figure 22:
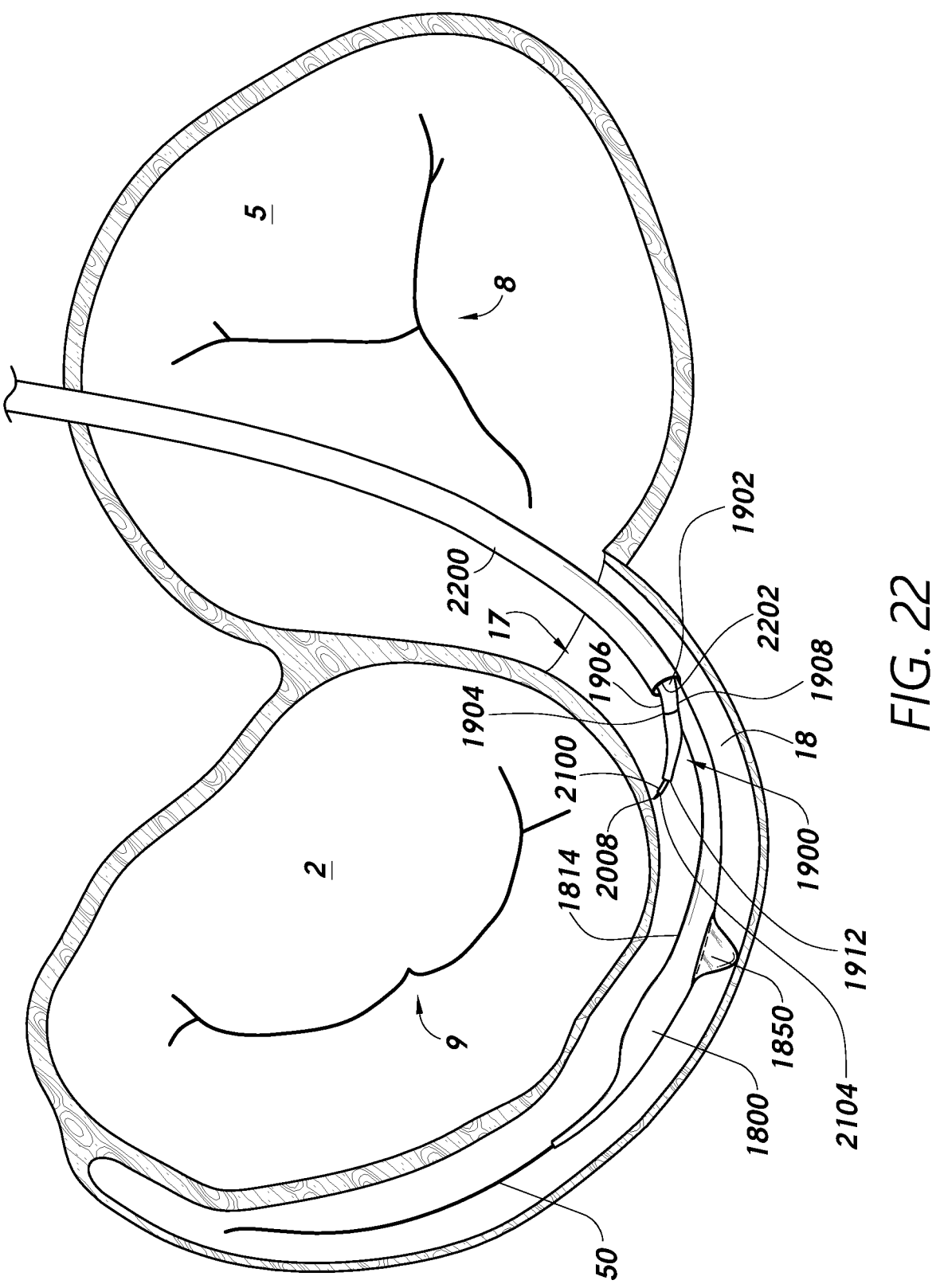

FIG. 22 shows proximal translation of the outer sheath and distal translation of the medical implant delivery catheter of the medical implant delivery system of FIG. 18, while the medical implant delivery system is positioned in the coronary sinus, in accordance with one or more embodiments.

Figure 23:
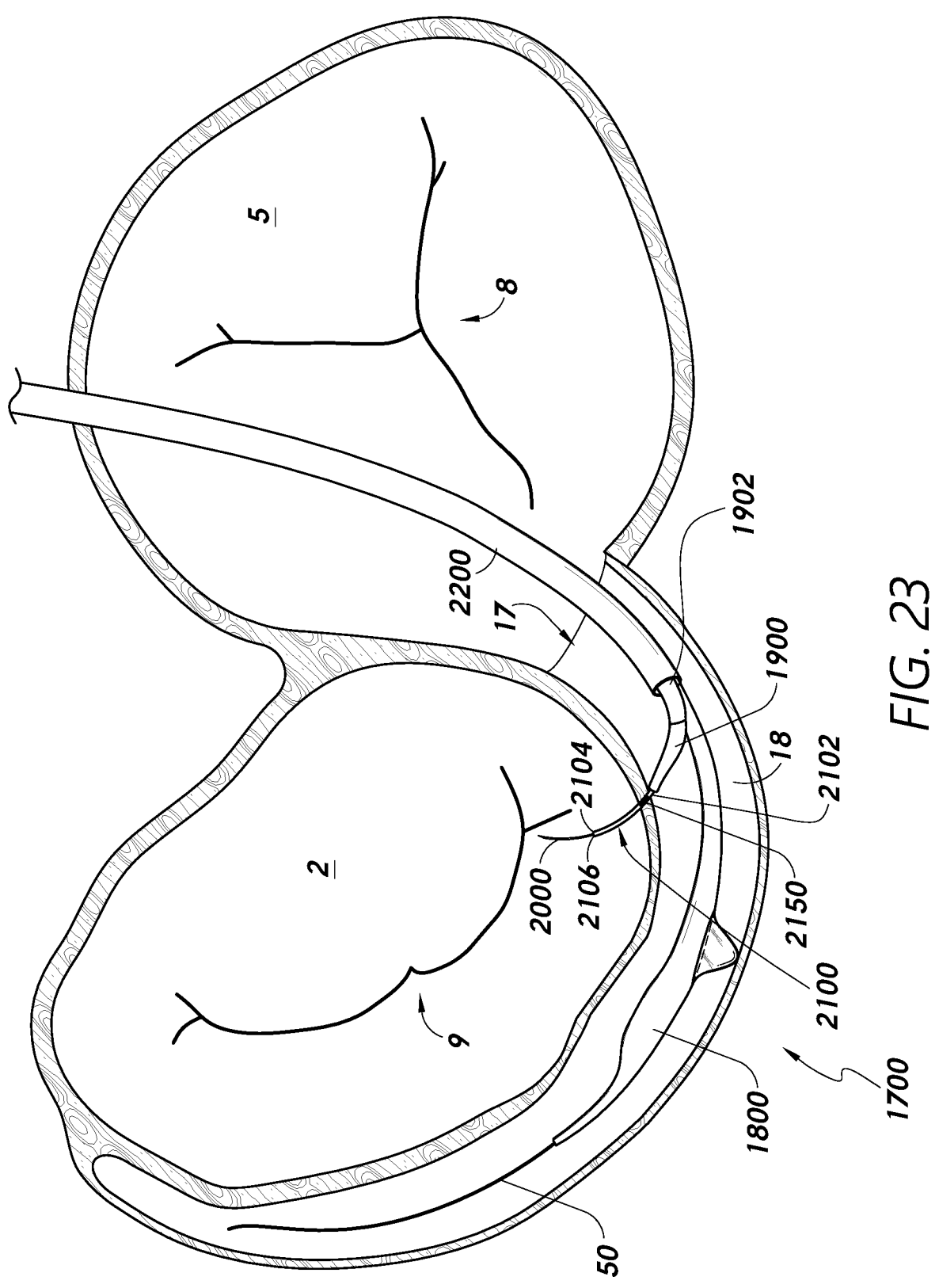

FIG. 23 shows the puncture needle of the medical implant delivery system of FIG. 18 inserted into the left atrium, in accordance with one or more embodiments.

Figure 24:
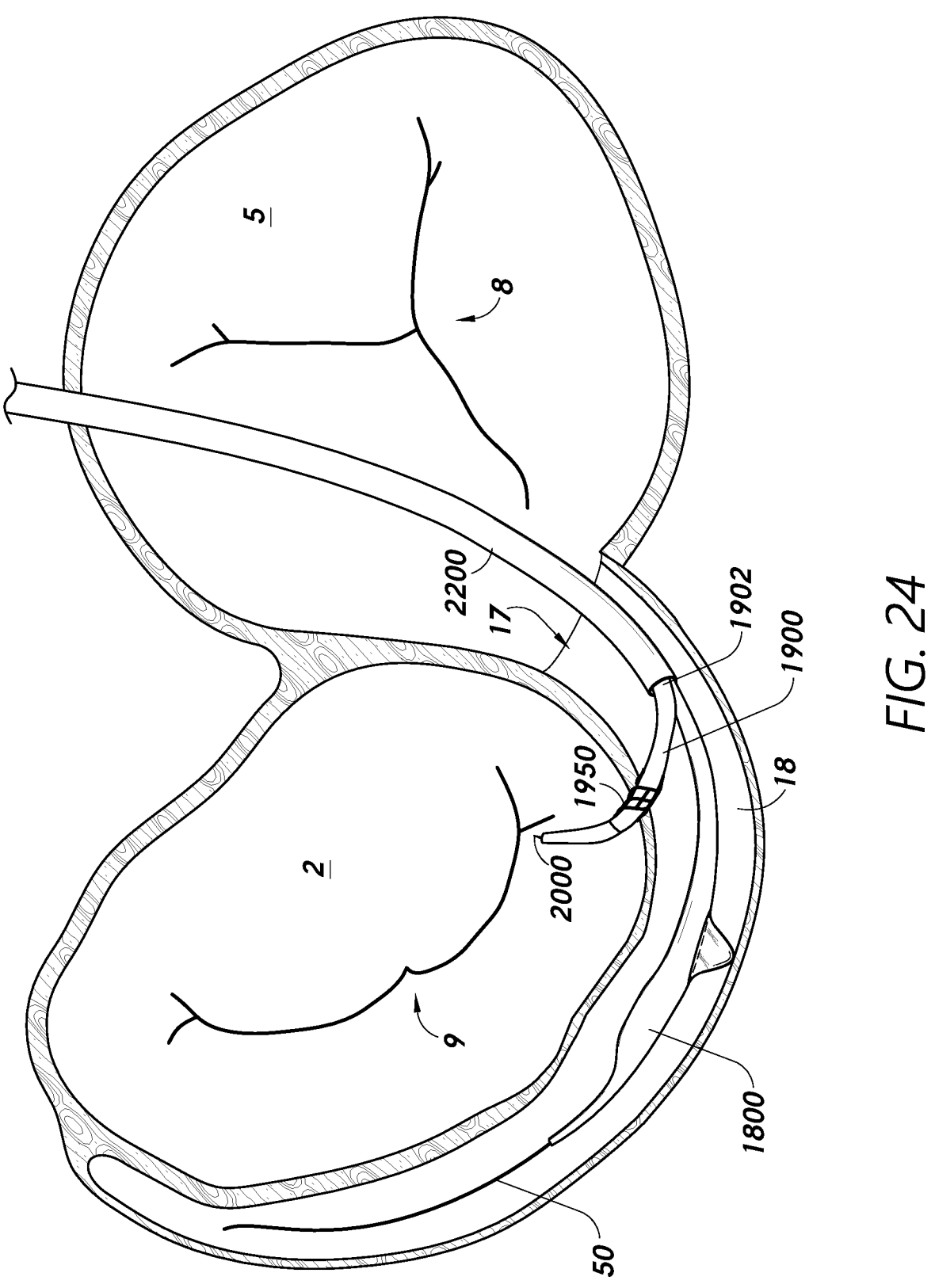

FIG. 24 shows deployment of a shunt device onto the left atrial wall using the medical implant delivery system of FIG. 18, in accordance with one or more embodiments.

FIG. 25 is a process flow diagram of an example of a process to deploy the medical implant delivery system of FIG. 18 to deliver a medical implant device, in accordance with one or more embodiments.

DETAILED DESCRIPTION

The headings provided herein are for convenience only and do not necessarily affect the scope or meaning of the claimed invention.

The present disclosure relates to systems and methods for providing minimally invasive transcatheter delivery of medical implant devices and/or therapies to a target tissue site on a vessel, channel, chamber and/or organ, including delivery of a shunt device to a target tissue wall, such as a left atrial wall.

Although certain preferred embodiments and examples are disclosed below, inventive subject matter extends beyond the specifically disclosed embodiments to other alternative embodiments and/or uses and to modifications and equivalents thereof. Thus, the scope of the claims that may arise herefrom is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Certain standard anatomical terms of location are used herein to refer to the anatomy of animals, and namely humans, with respect to the preferred embodiments. Although certain spatially relative terms, such as "outer," "inner," "upper," "lower," "below," "above," "vertical," "horizontal," "top," "bottom," and similar terms, are used herein to describe a spatial relationship of one device/element or anatomical structure to another device/element or anatomical structure, it is understood that these terms are used herein for ease of description to describe the positional relationship between element(s)/structures(s), as illustrated in the drawings. It should be understood that spatially relative terms are intended to encompass different orientations of the element(s)/structures(s), in use or operation, in addition to the orientations depicted in the drawings. For example, an element/structure described as "above" another element/structure may represent a position that is below or beside such other element/structure with respect to alternate orientations of the subject patient or element/structure, and vice-versa.

Figure 1:
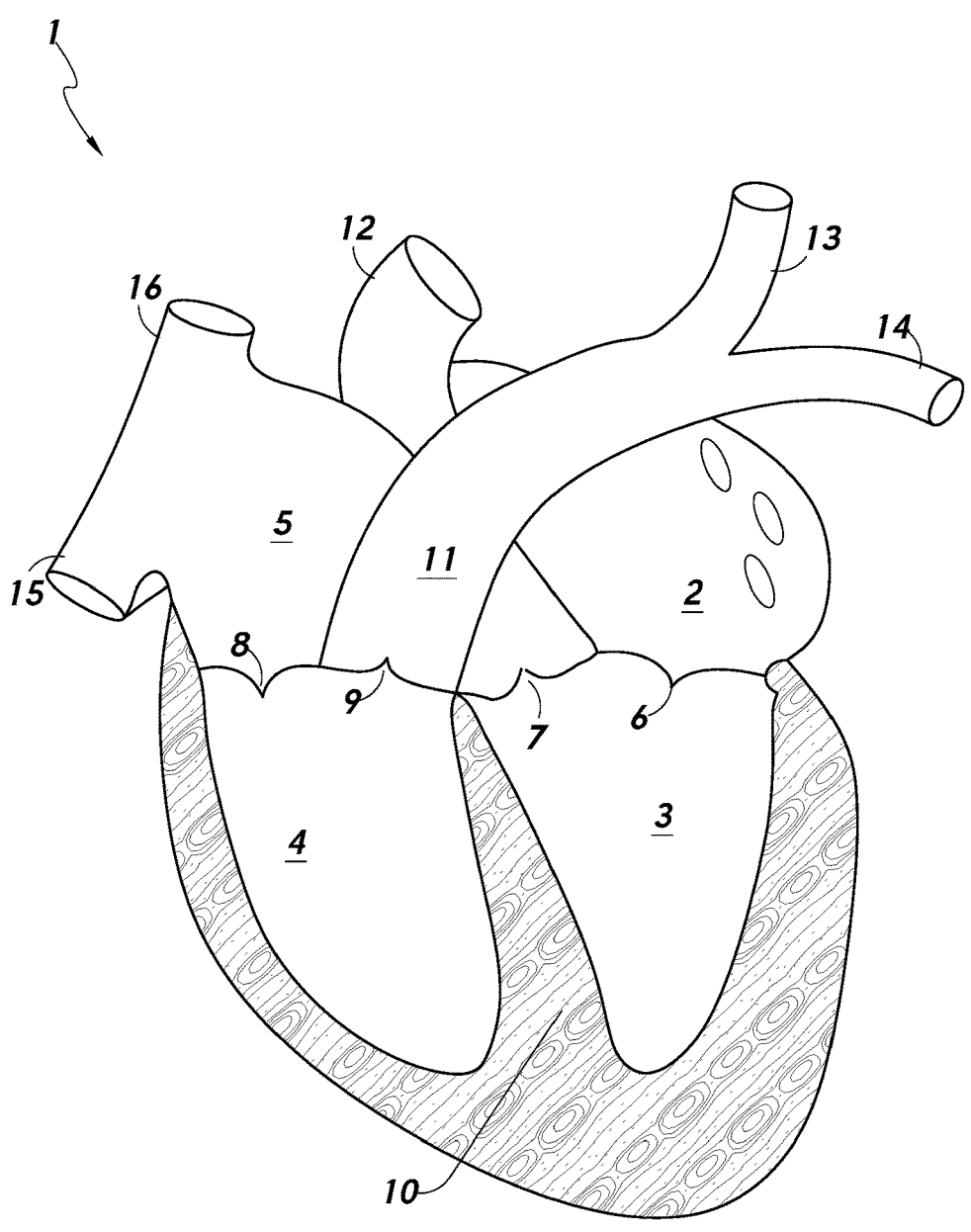
FIG. 1 is a cross-sectional view of a human heart.

Various features of a heart 1 are described with reference to FIG. 1 to assist in understanding the present disclosure. The heart 1 includes four chambers, namely the left atrium 2, the left ventricle 3, the right ventricle 4, and the right atrium 5. A wall of muscle, referred to as the septum 10, separates the left atrium 2 and right atrium 5, and the left ventricle 3 and right ventricle 4. Blood flow through the heart 1 is at least partially controlled by four valves, the mitral valve 6, aortic valve 7, tricuspid valve 8, and pulmonary valve 9. The mitral valve 6 separates the left atrium 2 and the left ventricle 3 and controls blood flow therebetween. The aortic valve 7 separates and controls blood flow between the left ventricle 3 and the aorta 12. The tricuspid valve 8 separates the right atrium 5 and the right ventricle 4 and controls blood flow therebetween. The pulmonary valve 9 separates the right ventricle 4 and the pulmonary artery 11, controlling blood flow therebetween.

In a healthy heart, the heart valves can properly open and close in response to a pressure gradient present during various stages of the cardiac cycle (e.g., relaxation and contraction) to at least partially control the flow of blood to a respective region of the heart and/or to blood vessels. Deoxygenated blood arriving from the rest of the body generally flows into the right side of the heart for transport to the lungs, and oxygenated blood from the lungs generally flows into the left side of the heart for transport to the rest of the body. During ventricular diastole, deoxygenated blood arrive in the right atrium 5 from the inferior vena cava 15 and superior vena cava 16 to flow into the right ventricle 4, and oxygenated blood arrive in the left atrium 2 from the pulmonary veins to flow into the left ventricle 3. During ventricular systole, deoxygenated blood from the right ventricle 4 can flow into the pulmonary artery 11 for transport to the lungs (e.g., via the left 14 and right 13 pulmonary arteries), and oxygenated blood can flow from the left ventricle 3 to the aorta 12 for transport to the rest of the body.

A number of conditions can contribute to a higher than normal pressure in the left atrium. Dysfunction of the mitral valve can contribute to elevated left atrial pressure. Conditions such as mitral valve regurgitation and/or stenosis may result in difficulty in pumping blood from the left atrium to the left ventricle, contributing to elevated pressure in the left atrium. Valve stenosis can cause a valve to become narrowed or obstructed. Mitral valve stenosis can restrict blood flow from the left atrium to the left ventricle. Valve regurgitation occurs when a valve does not close properly. For example, regurgitation can occur due to improper coaptation of the valve leaflets. Mitral valve regurgitation can result in blood flow leakage back into the left atrium 2 from the left ventricle 3 when the left ventricle 3 contracts. Restricted flow of blood from the left atrium 2 into the left ventricle 3, and blood flow leakage from the left ventricle 3 back into the left atrium 2 can both contribute to elevated atrial pressure. Dysfunction in the left ventricle 3 can also contribute to elevated left atrial pressure. Elevated left atrial pressure may lead to left atrial enlargement, producing symptoms such as shortness of breath during exertion, fatigue, chest pain, fainting, abnormal heartbeat, and swelling of the legs and feet.

Figure 2:
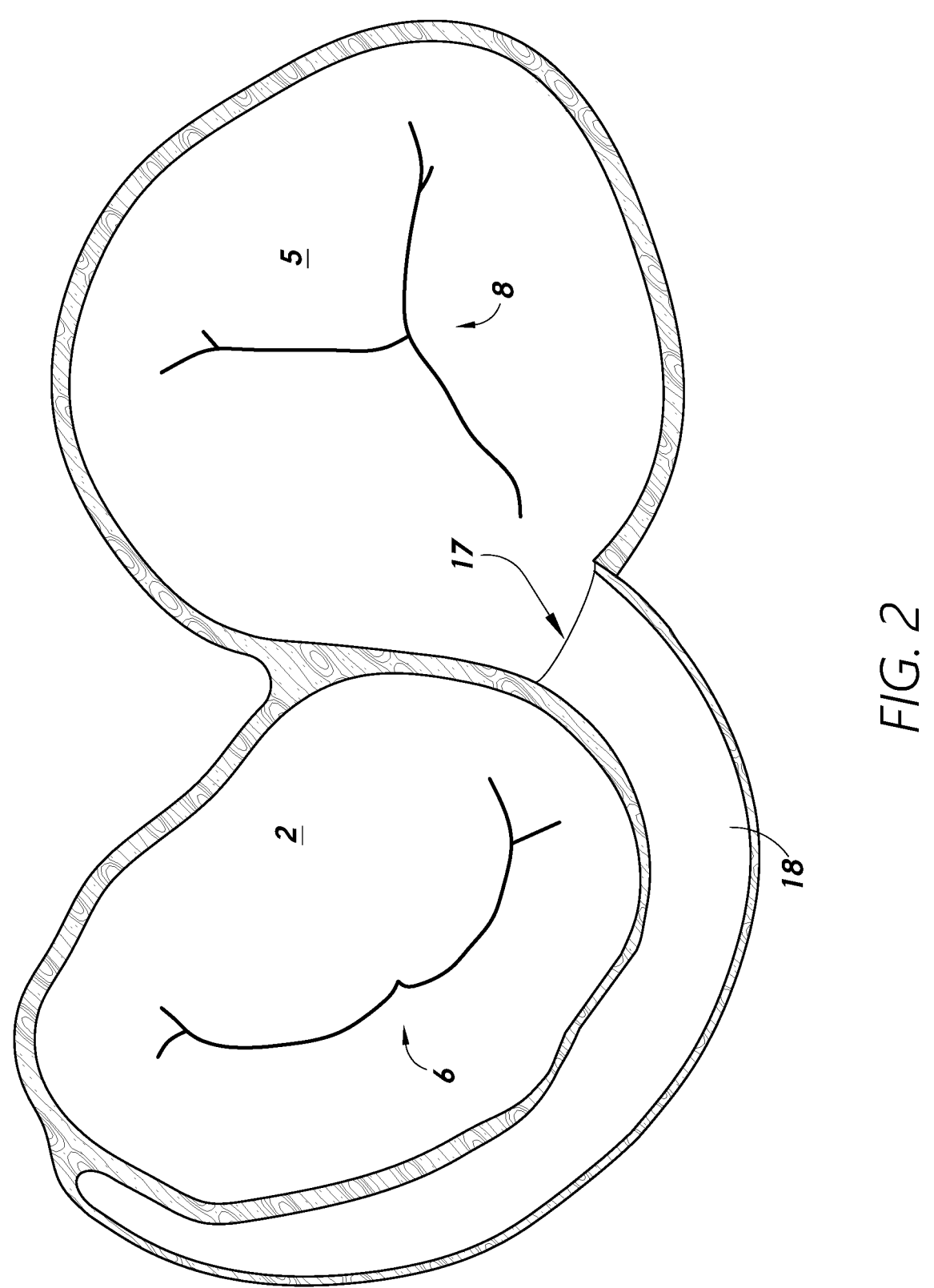
FIG. 2 is another cross-sectional view of the human heart.

FIG. 2 is another view of the heart 1 and shows the coronary sinus 18 around the left atrium 2. To alleviate elevated left atrial pressure, a conduit can be provided to allow blood flow from the left atrium 2 into a portion of the heart with lower pressure, such as the coronary sinus 18. A conduit can be formed on the wall of the left atrium 2 adjacent to the coronary sinus 18 to allow blood flow from the left atrium 2 into the coronary sinus 18. The coronary sinus 18 receives blood from coronary veins and empties into the right atrium 5. Blood diverted into the coronary sinus 18 from the left atrium 2 can then be delivered into the right atrium 5. A shunt device, including an expandable shunt device, can be positioned at a location on the left atrial wall, such as a location which is accessible from the coronary sinus 18, to form a blood flow pathway from the left atrium 2 into the coronary sinus 18. Access into the coronary sinus 18 can comprise navigating into the right atrium 5 and entering through the coronary sinus ostium 17.

Traditional minimally invasive transcatheter deployment of a medical implant device and/or therapy to a target tissue site, including transcatheter delivery of a shunt device to the left atrial wall, can include separately advancing a puncture needle delivery catheter and a medical implant delivery catheter. After an opening is formed at the target tissue site using the puncture needle, the puncture needle delivery catheter can be exchanged for the medical implant delivery catheter to deliver the medical implant device and/or therapy. The medical implant device and/or therapy can be delivered to a target tissue site in the heart for altering blood flow in the heart to treat various abnormal heart conditions. For example, a shunt device can be delivered to the left atrial wall to provide a blood flow pathway between the left atrium and the coronary sinus for relieving elevated left atrial pressure. Delivery of the shunt device to the left atrial wall can require formation of an opening in the left atrial wall. Typically, a puncture needle delivery catheter and a shunt device delivery catheter are separately introduced for forming the opening at the target tissue site and for positioning the shunt device into the opening, respectively. The puncture needle delivery catheter can be retracted and exchanged for the shunt device delivery catheter. Requiring exchange of the shunt device delivery catheter with the puncture needle delivery catheter can result in undesired trauma to patients, increased procedural complexity and/or increased procedural time.

The present disclosure provides systems and methods relating to minimally invasive transcatheter delivery of medical implant devices and/or therapies to a target tissue site. In some embodiments, described herein are medical implant delivery systems configured to enable simultaneously positioning to or proximate to a target tissue site both a puncture needle for piercing the tissue at the target tissue site and a medical implant device and/or therapy for deployment to the target tissue site. The puncture needle and the medical implant device and/or therapy can be delivered together to or proximate to the target tissue site without having to exchange a puncture needle delivery catheter for a delivery catheter to deliver the medical implant device and/or therapy. Delivering the puncture needle and medical implant device and/or therapy together to the target tissue site, without having to separately advance a puncture needle delivery catheter and a delivery catheter for the medical implant device and/or therapy, can facilitate reduced trauma to the patient, provide a simplified procedure, and/or improved procedure time. In some embodiments, use of one or more systems described herein can facilitate up to 50% reduction in procedure time.

In some embodiments, provided herein are medical implant delivery systems for delivering a puncture needle and a shunt device, such as an expandable shunt device, to a target tissue wall, including the left atrial wall. In some embodiments, the medical implant delivery systems can be configured to be positioned into the coronary sinus to access a portion of the left atrial wall from within the coronary sinus. For example, a medical implant delivery system can be advanced into the coronary sinus from the right atrium via the coronary sinus ostium. The right atrium can be accessed via the superior vena cava (SVC) or via the inferior vena cava (IVC). A transjugular or trans-subclavian approach can be used to access the right atrium via the superior vena cava. Alternatively, a transfemoral approach can be used to position the medical implant delivery system into the inferior vena cava, and from the inferior vena cava into the right atrium.

In some embodiments, a medical implant delivery system as described herein can comprise an outer delivery catheter and a medical implant delivery catheter slidably extending through a medical implant delivery lumen of the outer delivery catheter. The medical implant delivery catheter can comprise a puncture needle lumen configured to slidably receive a puncture needle. The puncture needle can extend through an opening on a distal end of the medical implant delivery catheter. A medical implant device can be positioned on the medical implant delivery catheter, such as on a distal portion of the medical implant delivery catheter. For example, a shunt device, such as an expandable shunt device, can be circumferentially positioned around the distal portion of the medical implant delivery catheter.

The outer delivery catheter can be advanced along a guide wire into the coronary sinus. The distal end of the medical implant delivery catheter can be positioned at or proximate to an outlet opening of the outer delivery catheter. In some embodiments, the medical implant delivery catheter can be pre-loaded into the outer delivery catheter. In some embodiments, the medical implant delivery catheter may not be pre-loaded and instead can be advanced from a proximal portion of the outer delivery catheter to the outlet opening after the outer delivery catheter is positioned at a desired location within the coronary sinus. A distal portion of the medical implant delivery catheter can be extended through the outlet opening to enable contact between the puncture needle and the target tissue site so as to form an opening at the target tissue site. After the puncture needle pierces the tissue, the medical implant delivery catheter can be further extended such that the distal portion of the medical implant delivery catheter extends through the opening formed at the target tissue site so as to deploy the shunt device into the opening, thereby enabling deployment of the shunt device without exchanging a delivery catheter for deploying the shunt device with a delivery catheter for delivering the puncture needle.

In some embodiments, a medical implant delivery system described herein can comprise an elongate housing, a medical implant delivery catheter extending alongside the elongate housing, and an outer sheath around the elongate housing and the medical implant delivery catheter. A medical implant device, including a shunt device, such as an expandable shunt device, can be positioned on the medical implant delivery catheter. For example, the shunt device can be circumferentially around a distal portion of the medical implant delivery catheter. The medical implant delivery catheter can comprise a puncture needle lumen and a puncture needle can be slidably extended through the puncture needle lumen. The puncture needle can be configured to extend through an opening on a distal end of the medical implant delivery catheter.

The elongate housing and the medical implant delivery catheter can be advanced along a guide wire into the coronary sinus. While being advanced to a desired location within the coronary sinus, the outer sheath can be positioned over the distal end of the medical implant delivery catheter to maintain the medical implant delivery catheter alongside the elongate housing. The outer sheath can be subsequently translated proximally relative to the medical implant delivery catheter to release the medical implant delivery catheter. The medical implant delivery catheter can be extended distally to enable contact between the puncture needle and the target tissue site so as to form an opening at the target tissue site. After the puncture needle pierces the tissue, the medical implant delivery catheter can be further extended such that the distal portion of the medical implant delivery catheter extends through the opening formed at the target tissue site so as to deploy the shunt device into the opening, thereby enabling deployment of the shunt device without having to exchange a delivery catheter for deploying the shunt device with a delivery catheter for delivering the puncture needle.

The term "associated with" is used herein according to its broad and ordinary meaning. For example, where a first feature, element, component, device, or member is described as being "associated with" a second feature, element, component, device, or member, such description should be understood as indicating that the first feature, element, component, device, or member is physically coupled, attached, or connected to, integrated with, embedded at least partially within, or otherwise physically related to the second feature, element, component, device, or member, whether directly or indirectly.

Reference herein to "catheters" and/or "delivery catheters" can refer or apply generally to any type of elongate tubular delivery device comprising an inner lumen configured to slidably receive instrumentation, such as for positioning within an atrium or coronary sinus, including for example delivery sheaths and/or cannulas.

Figure 3:
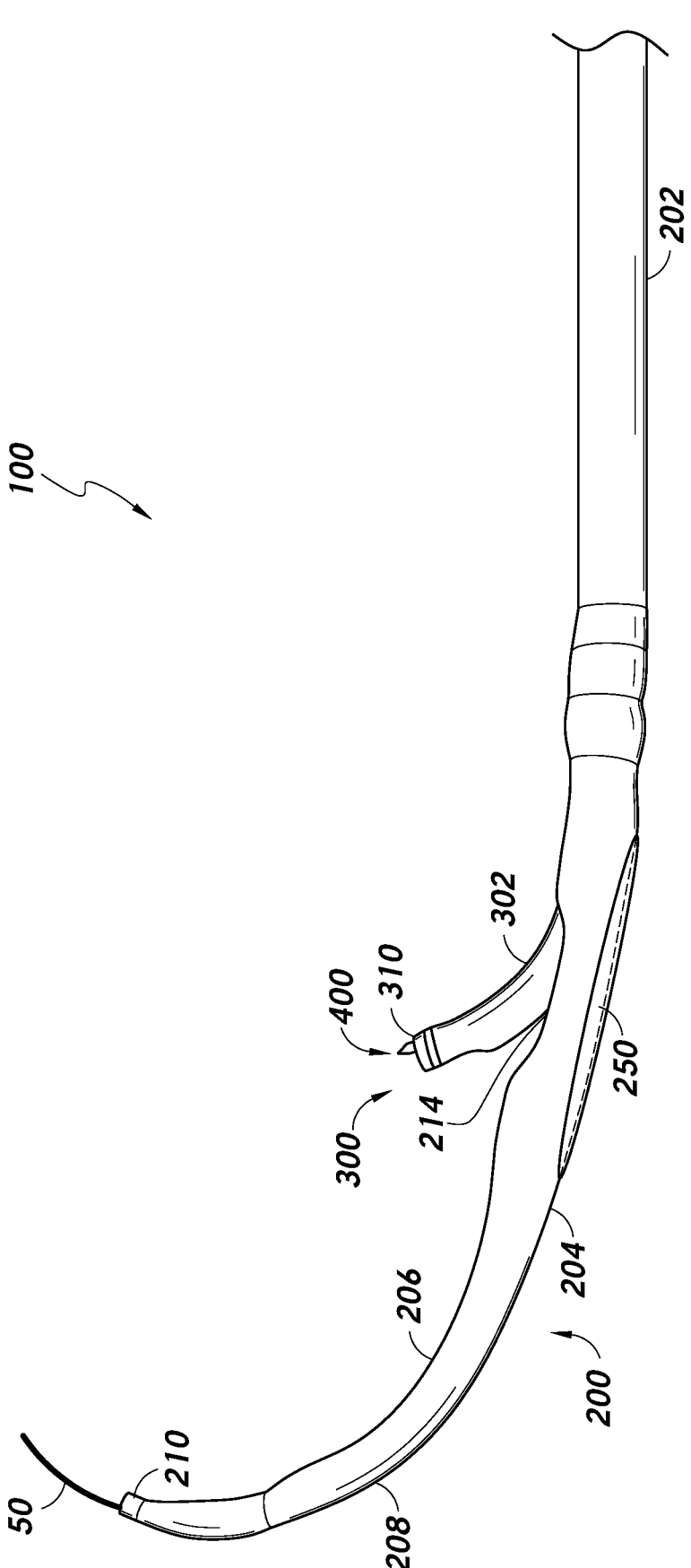
FIG. 3 is a side view of an example of a medical implant delivery system in accordance with one or more embodiments.

FIG. 3 is a side view of an example of a medical implant delivery system 100 comprising an outer delivery catheter 200 and a medical implant delivery catheter 300 slidably extending through a medical implant delivery lumen of the outer delivery catheter 200. The medical implant delivery catheter 300 can comprise a puncture needle lumen configured to slidably receive a puncture needle 400. In some embodiments, the medical implant delivery system 100 can comprise a puncture needle sheath (not shown) extending through the puncture needle lumen and the puncture needle 400 can extend through the puncture needle sheath. The puncture needle 400 can be delivered to a target tissue site so as to form an opening on the tissue. A medical implant device 350 (not shown) can be positioned on the medical implant delivery catheter 300 for deployment to the target tissue site. The medical implant device 350 can be positioned on the medical implant delivery catheter 300 such that a delivery catheter for delivering the puncture needle 400 does not need to be exchanged for a delivery catheter for delivering the medical implant device 350.

In FIG. 3, a distal portion 302 of the medical implant delivery catheter 300 is shown as extending through a side outlet opening 214 on a distal portion 202 of the outer delivery catheter 200, and the puncture needle 400 is shown as having a portion extending beyond a distal end 310 of the medical implant delivery catheter 300. The distal portion 202 of the outer delivery catheter 200 is shown in FIG. 3. As shown in the figure, the distal portion 202 can comprise a pre-formed curvature 204. The pre-formed curvature 204 can be configured to facilitate positioning of the outer delivery catheter 200 into a vessel, channel, chamber and/or organ so as to access the target tissue site. The target tissue site may be a part of the same vessel, channel, chamber and/or organ, or a different vessel, channel, chamber and/or organ. The target tissue site may be on a wall of a vessel, channel, chamber and/or organ. For example, the outer delivery catheter 200 can be positioned into a coronary sinus to access a portion of a left atrial wall accessible from within the coronary sinus. The side outlet opening 214 can be on an inner edge 206 of the pre-formed curvature 204. In some embodiments, the distal portion 202 can comprise one or more radiopaque markers thereon to facilitate visualization of the outer delivery catheter 200 for positioning the outer delivery catheter 200 at the desired location within the vessel, channel, chamber and/or organ.

A guide wire 50 can be slidably extended through a guide wire lumen of the outer delivery catheter 200. The guide wire 50 is shown in FIG. 3 as extending beyond a distal end 210 of the outer delivery catheter 200. The guide wire 50 can be positioned into the vessel, channel, chamber and/or organ such that the outer delivery catheter 200 can be subsequently advanced along the guide wire 50 into the vessel, channel, chamber and/or organ.

In some embodiments, the outer delivery catheter 200 can comprise an expandable anchor 250. In some embodiments, the expandable anchor 250 can comprise an expandable balloon anchor. The expandable anchor 250 can comprise any number of configurations which enables controlled triggering and/or activation such that the expandable anchor 250 can assume an expanded state from a collapsed state, and vice versa. The expandable anchor 250 is shown in FIG. 3 in a collapsed state. The expandable anchor 250 can be on an outer edge 208 of the pre-formed curvature 204. For example, the expandable anchor 250 can be on a portion of the outer delivery catheter 200 opposite that of the side outlet opening 214. In some embodiments, the expandable anchor 250 can be inserted to or proximate to the target tissue site in a collapsed configuration. The expandable anchor 250 can be subsequently triggered and/or actuated to assume an expanded configuration so as to contact tissue near the target tissue site to facilitate stable positioning of the outer delivery catheter 200. Reliable positioning of the outer delivery catheter 200 relative to the target tissue site can facilitate puncture of the tissue at the target tissue site. In some embodiments, the expandable anchor 250 can press against tissue near the target tissue site, including tissue at an opposing location relative to the target tissue site. Expansion of the expandable anchor 250 can push the delivery catheter 200 toward tissue adjacent to the target tissue, for example pressing the delivery catheter 200 against tissue adjacent to the target tissue. The inner edge 206 portion comprising the side outlet opening 214 of the outer delivery catheter 200 can be positioned against tissue adjacent to the target tissue site such that the puncture needle 400 can be reliably positioned at the target tissue site as the puncture needle 400 is advanced through the side outlet opening 214. In some embodiments, the expandable anchor 250 can be expanded such that the inner edge 206 of the delivery catheter 200 can be pressed against a portion of the left atrial wall adjacent to the target tissue site. The side outlet opening 214 can thereby be reliably positioned at and/or around the target tissue site on the left atrial wall. The expandable anchor 250 can resume a collapsed state for retraction from the target tissue site.

In some embodiments, an outer delivery catheter may not have an expandable anchor. In some embodiments, an outer delivery catheter comprising an expandable anchor can be selected for a patient with a vessel, channel, chamber and/or organ having a wider diameter at or proximate to the target tissue site.

Figure 4:
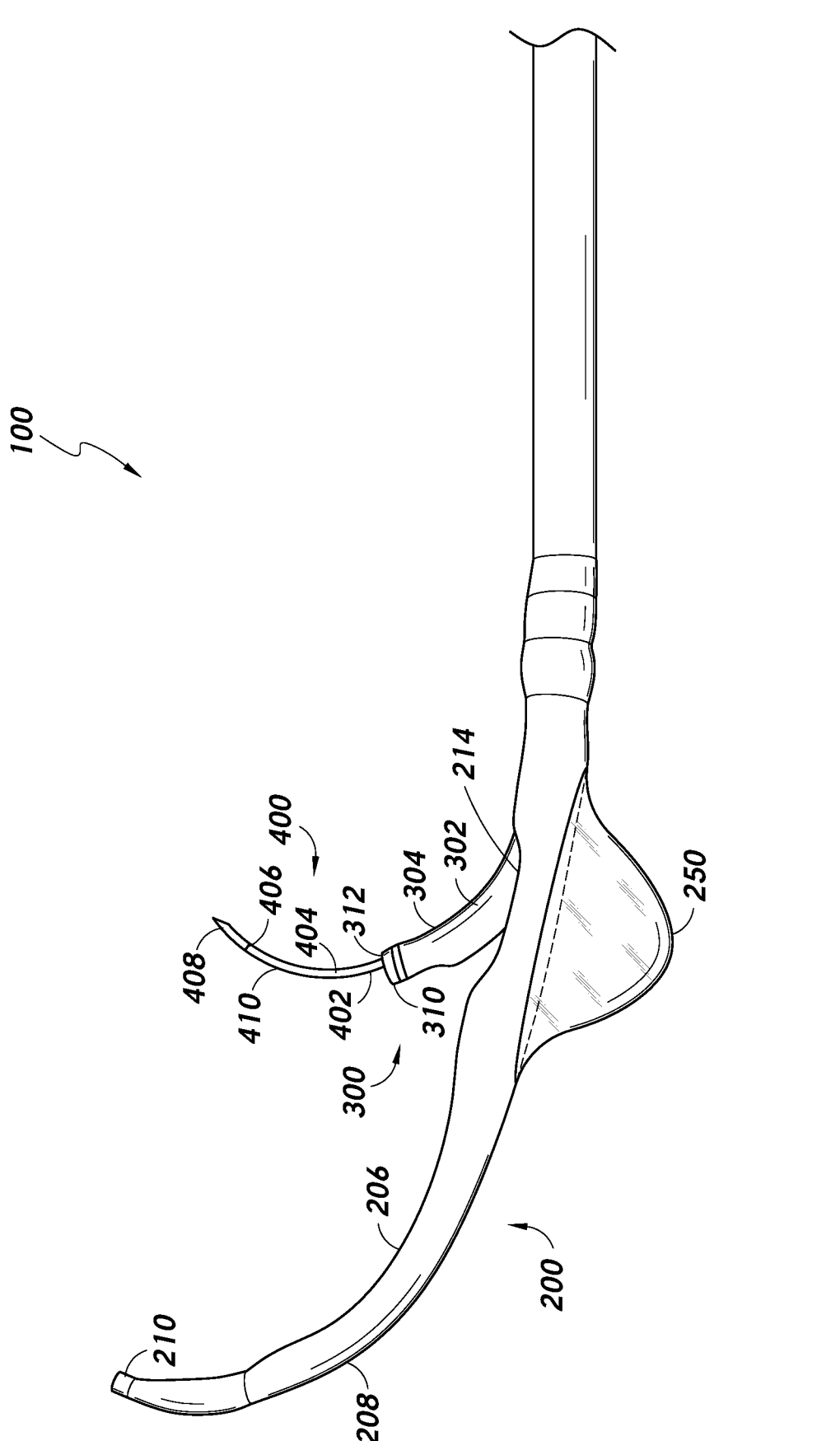
FIG. 4 is another side view of the medical implant delivery system of FIG. 3, in accordance with one or more embodiments.

FIG. 4 is another side view of the medical implant delivery system 100. The distal portion 302 of the medical implant delivery catheter 300 is shown extending beyond the side outlet opening 214. The expandable anchor 250 is shown in FIG. 4 in an expanded state. As described in further detail herein, the medical implant delivery catheter 300 can comprise a pre-formed curvature 304 configured to facilitate delivery of the puncture needle 400 to the target tissue site and/or deployment of the medical implant device 350 positioned on the medical implant delivery catheter 300.

A puncture needle outlet opening 312 can be associated with the distal portion 302, including the distal end 310, of the medical implant delivery catheter 300. The puncture needle 400 can comprise an elongate portion 402. A distal portion 404 of the elongate portion 402 is shown extending through the puncture needle outlet opening 312. A puncture component 408 associated with a distal end 406 of the elongate portion 402 can be used to pierce the tissue at the target tissue site to form the opening in the tissue. In some embodiments, the distal portion 404 of the puncture needle 400 can comprise a pre-formed curvature 410. In some embodiments, the pre-formed curvature 410 of the puncture needle 400 can facilitate piercing of tissue at the target tissue site. A target tissue site can be to a side of the outer delivery catheter 200 (e.g., at or proximate to the side outlet opening 214). As described herein, the medical implant delivery catheter 300 can be advanced through the side outlet opening 214 to access the target tissue site. The puncture needle 400 can be advanced through the puncture needle outlet opening 312 of the medical implant delivery catheter 300 to puncture the tissue. The curvature in the pre-formed curvature 410 can facilitate access of the target tissue site to the side of the outer delivery catheter 200 as the puncture needle 400 is advanced through the puncture needle outlet opening 312. Improved access of the puncture needle 400 to the target tissue site to a side of the outer delivery catheter 200 can provide effective puncturing of the tissue.

In some embodiments, the pre-formed curvature 410 can have the same or similar orientation as the pre-formed curvature 204 of the outer delivery catheter 200. In some embodiments, the pre-formed curvature 410 can have the same or similar orientation as the pre-formed curvature 304 of the medical implant delivery catheter 300. In some embodiments, the pre-formed curvature 410 can comprise a radius of curvature smaller than that of the pre-formed curvature 304.

In some embodiments, the medical implant delivery catheter 300 can be pre-loaded into the medical implant delivery lumen of the outer delivery catheter 200. The pre-loaded medical implant delivery catheter 300 can remain within the outer delivery catheter 200 until the outer delivery catheter 200 is positioned at or proximate to the target tissue site. For example, the distal end 310 of the medical implant delivery catheter 300 can remain within the medical implant delivery lumen and may not extend beyond the side outlet opening 214 until the outer delivery catheter 200 is positioned within the desired vessel, channel, chamber and/or organ. The distal end 310 of the medical implant delivery catheter 300 may not extend beyond the side outlet opening 214 while the medical implant delivery catheter 300 is in a retracted configuration. In the retracted state, the distal end 310 may be positioned proximal of, at, or distal of the side outlet opening 214. As described herein, the distal end 310 of the medical implant delivery catheter 300 can be pre-loaded and positioned adjacent to and proximal of the side outlet opening 214. In some embodiments, the distal end 310 of the medical implant delivery catheter 300 can be pre-loaded and positioned adjacent to and distal of the side outlet opening 214. In some embodiments, the medical implant delivery catheter 300 may not be pre-loaded and can be advanced from a proximal portion of the outer delivery catheter 200 to the side outlet opening 214 after the outer delivery catheter 200 has been positioned in the desired vessel, channel, chamber and/or organ.

In some embodiments, the puncture needle 400 can be pre-loaded into the puncture needle lumen of the medical implant delivery catheter 300. In some embodiments, the puncture needle 400 can remain within the medical implant delivery catheter 300 until the outer delivery catheter 200 is positioned at or proximate to the target tissue site. For example, the puncture component 408 may not extend beyond the puncture needle outlet opening 312 until the outer delivery catheter 200 is positioned within the vessel, channel, chamber and/or organ. The puncture component 408 can remain within the medical implant delivery catheter 300 while the puncture needle is in a retracted configuration. In some embodiments, a portion of the puncture needle 400 can be extended through the puncture needle outlet opening 312 while the puncture needle 400 is in the retracted configuration, but that portion of the puncture needle 400 can remain within the outer delivery catheter 200. For example, the puncture component 408 can extend through the puncture needle outlet opening 312 while the puncture needle 400 is in the retracted configuration. The puncture component 408 extending beyond the puncture needle outlet opening 312 can reside within the medical implant delivery lumen of the outer delivery catheter 200 until the outer delivery catheter 200 is positioned into the desired vessel, channel, chamber and/or organ, including after the side outlet opening 214 is positioned at a desired position within the vessel, channel, chamber and/or organ. In some embodiments, the puncture needle 400 may not be pre-loaded and can be advanced from a proximal portion of the medical implant delivery catheter 300 to the puncture needle outlet opening 312 after the outer delivery catheter 200 has been positioned in the desired vessel, channel, chamber and/or organ.

In some embodiments, the distal portion 404 of the puncture needle 400 can comprise a shape memory material. As described herein, the distal portion 404 can remain within the medical implant delivery catheter 300 until the outer delivery catheter 200 is positioned at or proximate to the target tissue site, such as the side outlet opening 214 of the outer delivery catheter 200. The distal portion 404 can assume a configuration having a reduced curvature while received within the medical implant delivery catheter. In some embodiments, the distal portion 404 can assume a linear or substantially linear configuration while received within the medical implant delivery catheter. After extension of the distal portion 404 through the puncture needle outlet opening 312, the pre-formed curvature 410 on the distal portion 404 can assume the curved configuration. The distal portion 404 can again assume the reduced curvature configuration, including the linear or substantially linear configuration, after retraction back into the medical implant delivery catheter 300.

In some embodiments, the medical implant delivery system 100 can comprise a radially expandable member (not shown) configured to be inserted into and dilate the opening formed in the tissue by the puncture needle 400. Enlargement of the opening can facilitate positioning of the medical implant device 350 (not shown) into the opening. The radially expandable member can be associated with a distal portion of a puncture needle sheath (not shown). For example, the puncture needle sheath can extend through the puncture needle lumen of the medical implant delivery catheter 300 and the puncture needle 400 can extend through the puncture needle sheath. For example, at least a portion of the puncture needle 400 can extend within the puncture needle sheath and at least a portion of the puncture needle sheath can extend within the medical implant delivery catheter 300. In some embodiments, the distal portion 302 of the medical implant delivery catheter 300 can be configured to provide desired dilation of the opening. For example, the distal portion 302 can be inserted into the opening to enlarge the opening. The distal portion 302 can comprise a size and/or shape to facilitate dilation of the opening, for example, having a predetermined diameter configured to provide the desired enlargement. In some embodiments, both the radially expandable member and the distal portion 302 can be used to dilate the opening. For example, the radially expandable member can be used to provide an initial dilation of the opening to facilitate insertion of the distal portion 302 into the opening to provide any desired remaining enlargement of the opening.

In some embodiments, the puncture needle 400 can be exchanged for a medical implant guide wire configured to be inserted through the opening formed at the target tissue site to guide deployment of the medical implant device 350. For example, the puncture needle 400 can be retracted, and the medical implant guide wire can be advanced through the puncture needle lumen or a puncture needle sheath extending through the puncture needle lumen. The medical implant delivery catheter 300 can be advanced along the medical implant guide wire such that the distal portion 302 of the medical implant delivery catheter 300 can be inserted through the opening and the medical implant device 350 can be positioned into the opening. In some embodiments, the puncture needle 400 can be further advanced into the opening after formation of the opening to guide subsequent advancement of the medical implant delivery catheter 300, rather than guide wire. The medical implant delivery catheter 300 can be advanced along the puncture needle 400 such that the medical implant device 350 can be positioned into the opening.

Figure 5:
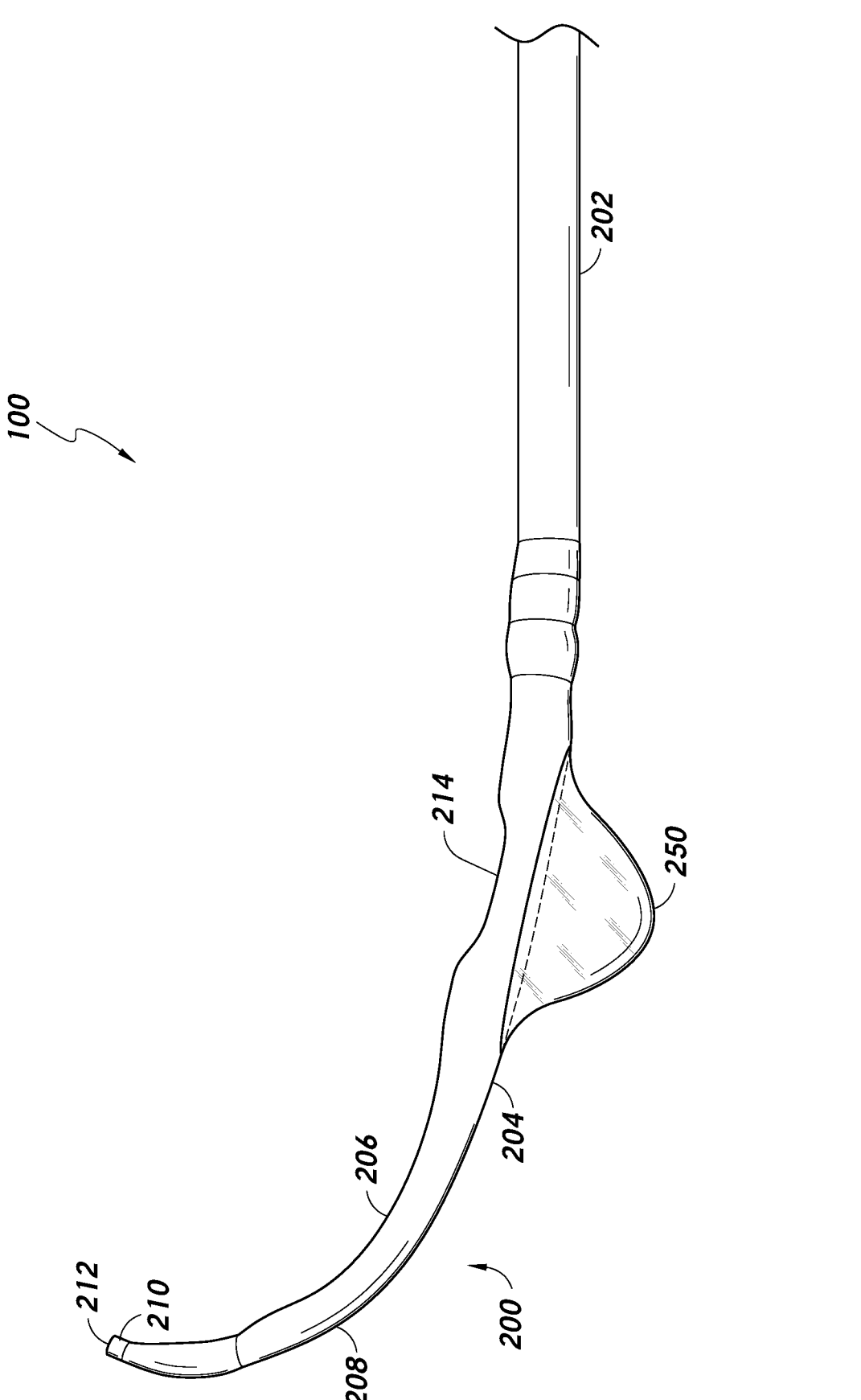
FIG. 5 is a side view of an outer delivery catheter of the medical implant delivery system of FIG. 3, in accordance with one or more embodiments.

FIG. 5 is a side view of the distal portion 202 of the outer delivery catheter 200. A guide wire outlet opening 212 can be associated with the distal end 210 of the outer delivery catheter 200. For example, the guide wire outlet opening 212 can be at the distal end 210. As described herein, the guide wire 50 can extend through the guide wire lumen of the outer delivery catheter 200. The guide wire lumen can extend along a length of the outer delivery catheter 200 such that the outer delivery catheter 200 can be passed along the guide wire 50 to advance the outer delivery catheter 200 to a desired location within the vessel, channel, chamber and/or organ. In some embodiments, the guide wire lumen can extend along an entire or substantially an entire length of the outer delivery catheter 200. For example, the guide wire 50 can extend through an entire or substantially an entire length of the outer delivery catheter 200 and exit through the guide wire outlet opening 212 at the distal end 210.

The side outlet opening 214 can be on the distal portion 202 of the outer delivery catheter 200. As described herein, the distal portion 202 of the outer delivery catheter 200 can comprise a pre-formed curvature 204. The side outlet opening 214 can be on the pre-formed curvature 204, for example on an inner edge 206 of the pre-formed curvature 204. For example, after the outer delivery catheter 200 is advanced to a desired location within the desired vessel, channel, chamber and/or organ, the inner edge 206 can be oriented towards the target tissue site, orienting the side outlet opening 214 towards the target tissue, such that the medical implant delivery catheter 300 can be extended through the side outlet opening 214 towards the target tissue site. The puncture needle 400 can then be deployed to contact tissue at the target tissue site. The outer edge 208 of the pre-formed curvature 204 can be oriented away from the target tissue site, such as oriented toward an opposing location relative to the target tissue site.

In some embodiments, the distal portion 202 can comprise a taper. A size of the distal portion 202 can taper toward the distal end 210. For example, a diameter of the outer delivery catheter 200 can narrow toward the distal end 210. The taper in the distal portion 202 and/or the pre-formed curvature 204 can be configured to facilitate positioning of the outer delivery catheter 200 into a desired vessel, channel, chamber and/or organ. In some embodiments, a radius of curvature and/or a length of the pre-formed curvature 204 can be selected based at least in part on a shape and/or dimension of the desired vessel, channel, chamber and/or organ. In some embodiments, the medical implant delivery system 100 can be configured to be positioned within the coronary sinus. As described in further detail herein, the medical implant delivery system 100 can be positioned into the coronary sinus via the coronary sinus ostium. The outer delivery catheter 200 can be positioned within the coronary sinus to access a site on the left atrial wall accessible from within the coronary sinus. The tapering in the distal portion 202 can facilitate insertion into narrower portions of the coronary sinus. The length of the pre-formed curvature 204 can be selected based at least in part on a distance of the target tissue site from the coronary sinus ostium. The radius of curvature of the pre-formed curvature 204 can be selected based at least in part on a shape of the coronary sinus, including a degree of curvature of the coronary sinus, in which the outer delivery catheter 200 is positioned. The radius of curvature of the pre-formed curvature 204 can be selected such that the pre-formed curvature 204 can conform or substantially conform to the curvature of a curve of the coronary sinus adjacent into which the outer delivery catheter 200 is positioned. The pre-formed curvature 204 can be positioned such that the inner edge 206 of the pre-formed curvature 204 is oriented towards a portion of the left atrial wall and the outer edge 208 of the curvature is oriented towards a portion of the wall of the coronary sinus, such as an opposing portion of the wall of the coronary sinus. For example, the pre-formed curvature 204 can follow or substantially follow the curve. In some embodiments, the distal portion 202 of the outer delivery catheter 200 can comprise a shape memory material. For example, the pre-formed curvature 204 can assume the curved configuration after the outer delivery catheter 200 is advanced into the coronary sinus.

Figure 6:
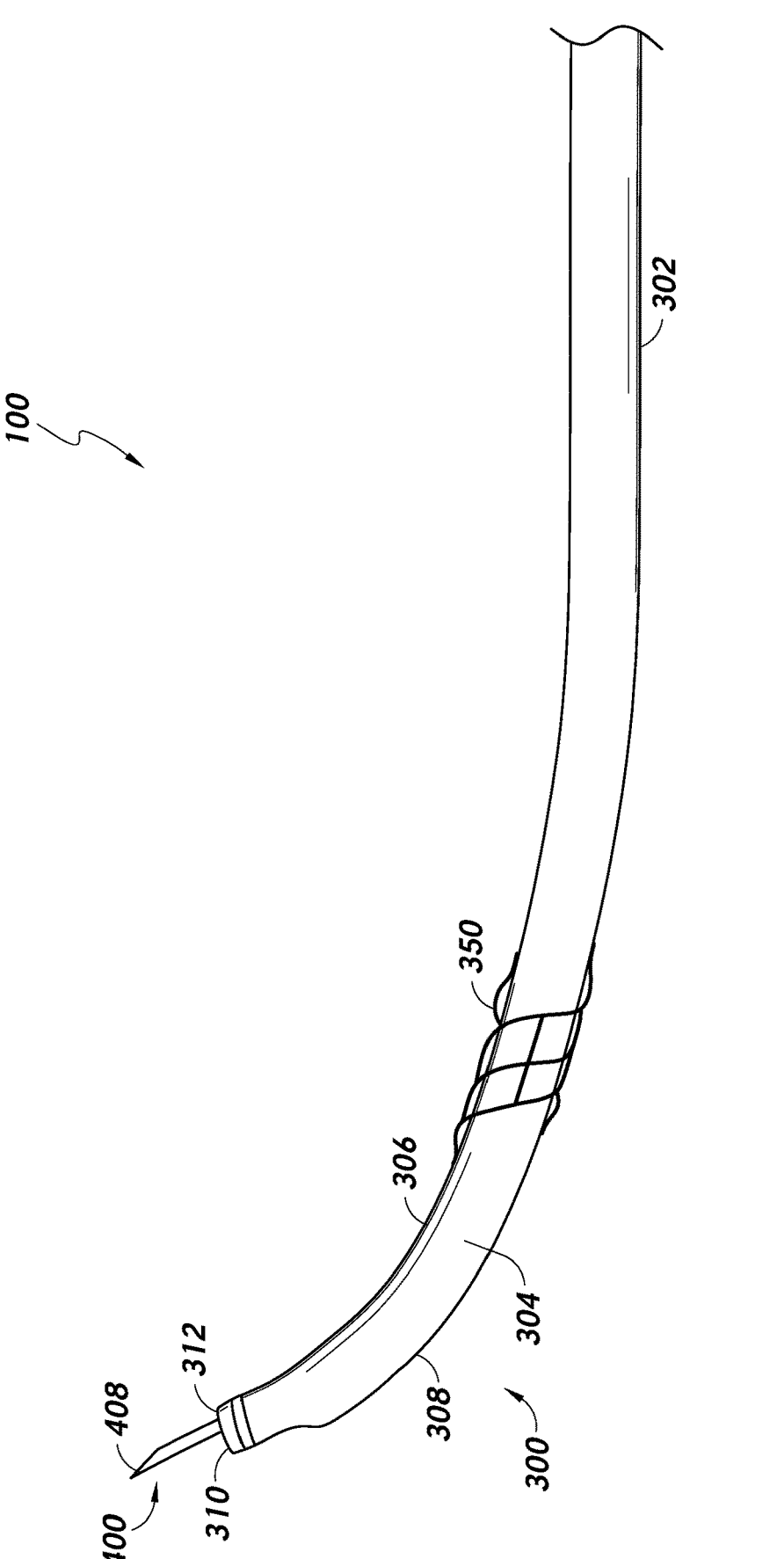
FIG. 6 is a side view of a medical implant delivery catheter of the medical implant delivery system of FIG. 3, in accordance with one or more embodiments.

FIG. 6 is a side view of the distal portion 302 of the medical implant delivery catheter 300 and the puncture needle 400 extending through the puncture needle outlet opening 312 associated with the distal end 310 of the medical implant delivery catheter 300. The medical implant delivery catheter 300 can comprise the pre-formed curvature 304 on the distal portion 302. The pre-formed curvature 304 can have a same or similar orientation as the pre-formed curvature 204 of the outer delivery catheter 200. For example, when the medical implant delivery catheter 300 is positioned in the coronary sinus, an inner edge 306 of the pre-formed curvature 304 can be oriented towards the left atrial wall and an outer edge 308 of the pre-formed curvature 304 can be oriented towards an opposing portion of a wall of the coronary sinus. In some embodiments, the pre-formed curvature 304 can have a smaller radius of curvature than the pre-formed curvature 204.

The medical implant device 350 can be carried by the medical implant delivery catheter 300. Referring to FIG. 6, in some embodiments, the medical implant device 350 can be positioned on the pre-formed curvature 304. The medical implant device 350 can be circumferentially positioned around the distal portion 302, including on the pre-formed curvature 304 of the pre-formed curvature. In some embodiments, the medical implant device 350 can comprise a shunt device, including an expandable shunt device. For example, the expandable shunt device can be configured for delivery to the left atrial wall for addressing elevated left atrial pressure. The expandable shunt device can be positioned around a portion of the distal portion 302, such as around a portion of the pre-formed curvature 304 of the distal portion 302.

The expandable shunt device can have a number of configurations. In some embodiments, the expandable shunt device can comprise an expandable tubular shunt device. Examples of suitable expandable shunt devices for the medical implant delivery system 100 are provided in U.S. patent application Ser. No. 15/335,891, entitled "Systems for Deploying an Expandable Cardiac Shunt," which is incorporated herein in its entirety.

The pre-formed curvature 304 can facilitate accessing the target tissue site while the medical implant delivery system 100 is positioned in the vessel, channel, chamber and/or organ. For example, the pre-formed curvature 304 can facilitate proper positioning of the puncture needle 400 at the target tissue site as the medical implant delivery catheter 300 is extended through the side outlet opening 214 of the outer delivery catheter 200. As described herein, a target tissue site can be to a side of the outer delivery catheter 200 (e.g., at or proximate to the side outlet opening 214). The curvature in the distal portion 302 of the implant delivery catheter 300 can facilitate access of the target tissue site to the side of the delivery catheter 200 as the distal portion 302 is advanced through the side outlet opening 214, thereby facilitating proper positioning of the puncture needle 400. Proper positioning of the puncture needle 400 can enable effective puncturing of the target tissue site.

In some embodiments, the distal portion 302 can comprise a taper. A size of the distal portion 302 can taper toward the distal end 310. For example, a diameter of the medical implant delivery catheter 300 can narrow toward the distal end 310. In some embodiments, the taper of the distal portion 302 and/or the pre-formed curvature 304 can facilitate desired deployment of the medical implant device 350 to the target tissue site. As described in further detail herein, the distal portion 302 can be further extended through the opening formed at the target tissue site, such that the medical implant device 350 can be positioned within the opening and deployed. The taper in the distal portion 302 can ease insertion of the distal portion 302 through the opening formed in the tissue. The pre-formed curvature 304 can enable the distal portion 302 to follow a pre-determined trajectory as the distal portion 302 is extended through the side outlet opening 214 of the outer delivery catheter 200 to access the target site to a side of the outer delivery catheter 200 and such that the distal portion 302 can be inserted into the opening.

In some embodiments, the distal portion 302 of the medical implant delivery catheter 300 can comprise a shape memory material. As described herein, the distal portion 302 can remain within the outer delivery catheter 200 until the outer delivery catheter 200 is positioned at or proximate to the target tissue site. While in a retracted state within the outer delivery catheter, the pre-formed curvature 304 of the distal portion 302 can comprise a configuration having a reduced curvature relative to its relaxed state, such as when the pre-formed curvature 304 is deployed through the side outlet opening 214. In some embodiments, the distal portion 302 can assume a linear or substantially linear configuration, while received within the outer delivery catheter 200. After extension of the distal portion 302 through the side outlet opening 214, the pre-formed curvature 304 on the distal portion 302 can assume the curved configuration. The pre-formed curvature 304 can again assume the reduced curvature configuration, including the linear or substantially linear configuration, after retraction back into the outer delivery catheter 200. In some embodiments, the outer delivery catheter 200, medical implant delivery catheter 300, and/or puncture needle 400 can be flexible such that the outer delivery catheter 200, medical implant delivery catheter 300, and/or puncture needle 400 can conform to the shape of anatomical pathways as the medical implant delivery system 100 is advanced through tortuous pathways.

Figure 7:
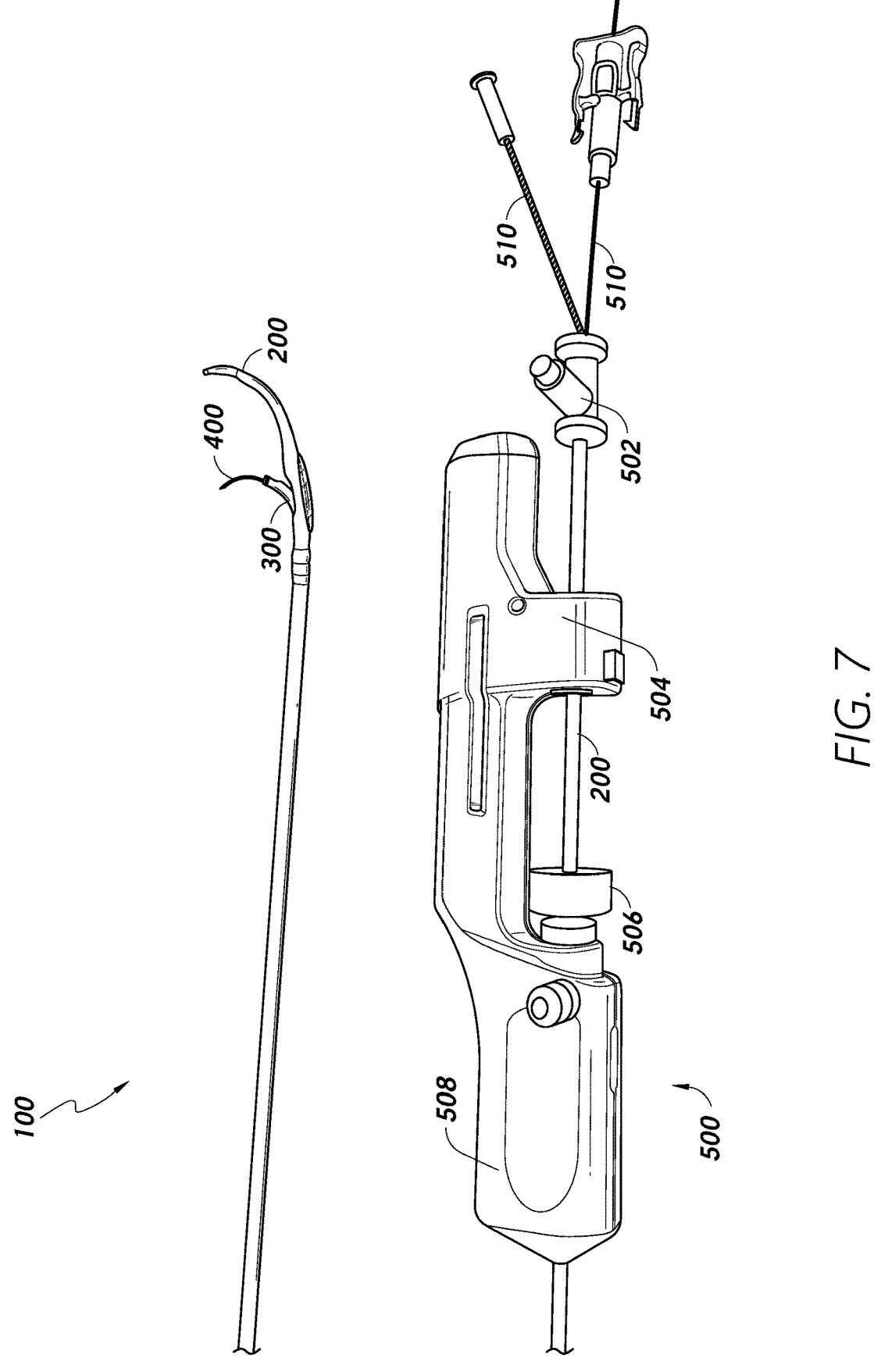
FIG. 7 shows a proximal handle of the medical implant delivery system of FIG. 3, in accordance with one or more embodiments.

FIG. 7 is a perspective view of an example of a proximal handle 500 of the medical implant delivery system 100. The proximal handle 500 can be configured to provide control for the deployment of the medical implant delivery system 100. The proximal handle 500 can comprise control mechanisms for both puncturing tissue at the target tissue site using the puncture needle 400 and deploying the medical implant device 350 positioned on the medical implant delivery catheter 300. Use of one proximal handle for both tissue puncture and medical implant device deployment can simplify the process for the operator, thereby facilitating a shortened procedure.

An advancer 502 on the proximal handle 500 can be configured to translate proximally and/or distally through a rear bracket 504. Advancement and/or retraction of the medical implant delivery catheter 300 and outer delivery catheter 200 can be controlled by the advancer 502. For example, the advancer 502 can be translated distally to advance the medical implant delivery catheter 300 and the outer delivery catheter 200. The medical implant delivery catheter 300 and outer delivery catheter 200 can extend through the locking nut 506. The locking nut 506 can be fixed relative to a forward bracket 508 such that the advancer 502, the medical implant delivery catheter 300 and outer delivery catheter 200 can be fixed relative to the proximal handle 500. The proximal handle 500 can comprise a pair of flexible arms 510 configured to allow controlled deployment of the medical implant device 350. For example, the pair of flexible arms 510 can be used to trigger and/or actuate controlled release of the medical implant device 350 from the medical implant delivery catheter 300 into the opening formed at the target tissue site.

Figure 8A:
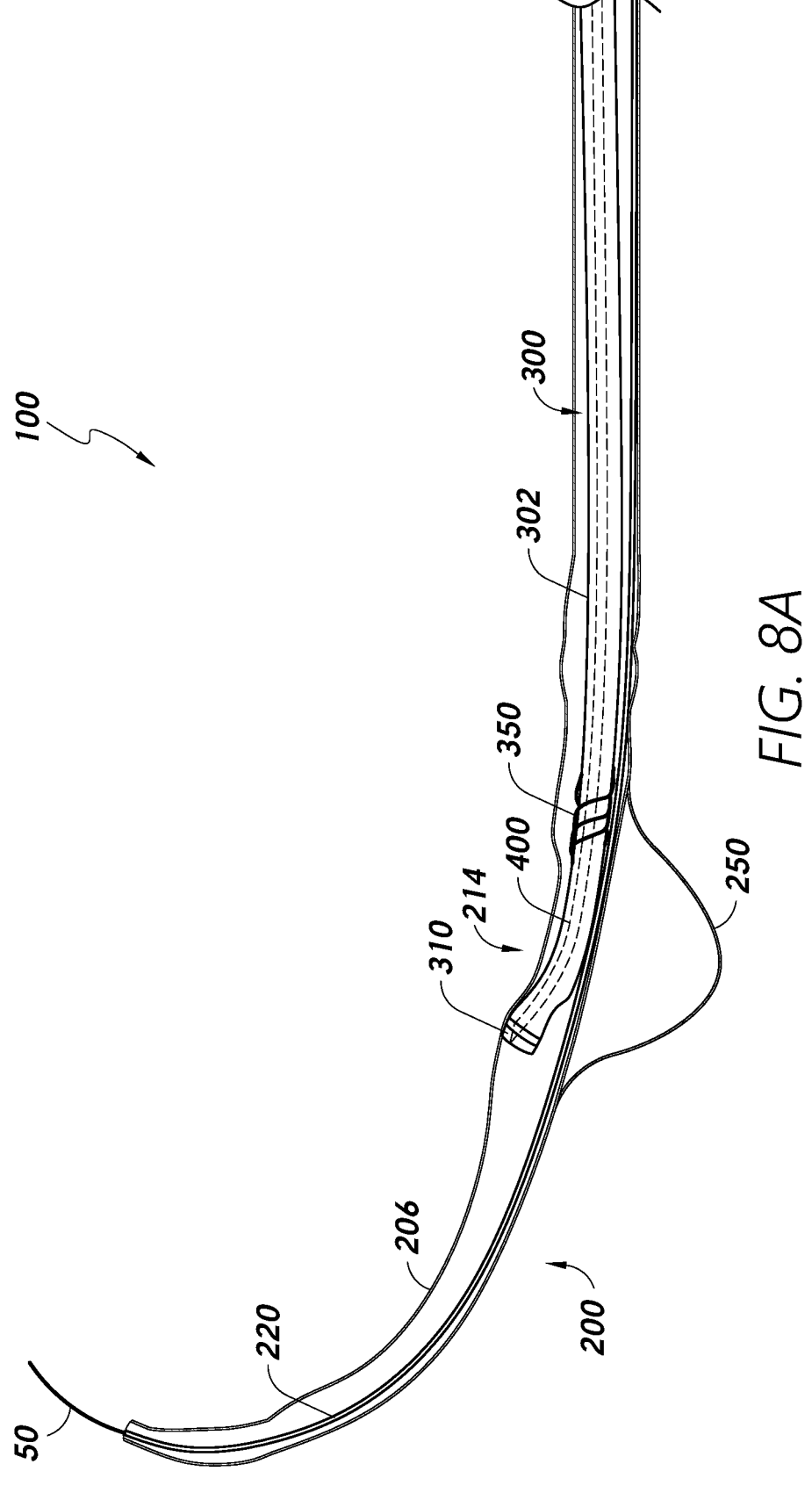
FIGS. 8A and 8B are longitudinal cross-sectional views of the medical implant delivery system of FIG. 3 in a first configuration and a second configuration, respectively, in accordance with one or more embodiments.
Figures 8B, 9:
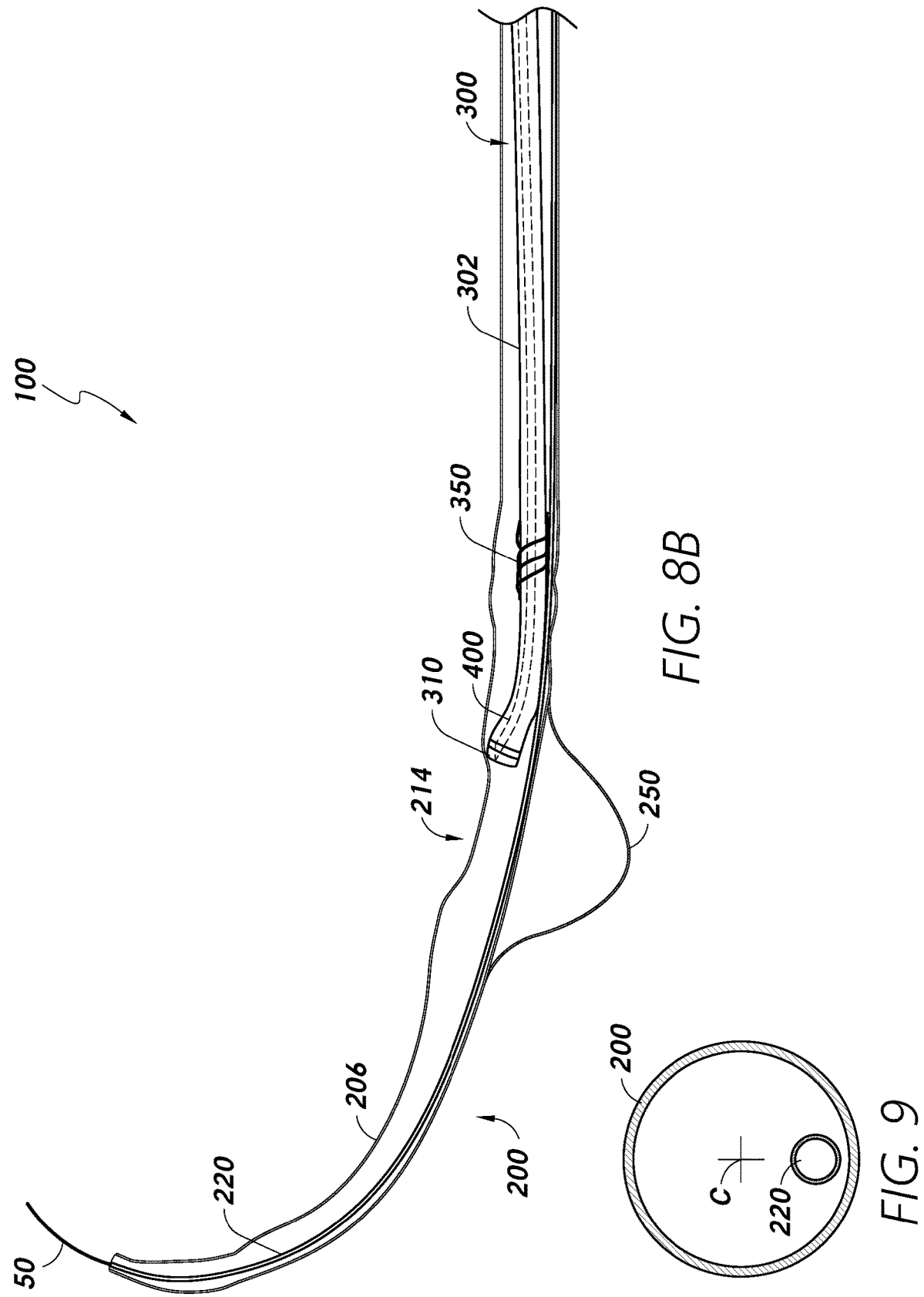
FIG. 9 shows a lateral cross-sectional view of the outer delivery catheter of FIG. 5, in accordance with one or more embodiments.

FIGS. 8A and 8B show longitudinal cross-sectional views of the medical implant delivery system 100 in a first configuration and a second configuration, respectively. The longitudinal cross-sectional view can comprise a cross-sectional view of the outer delivery catheter 200 along a longitudinal axis of the outer delivery catheter 200. The distal portion 302 of the medical implant delivery catheter 300 is shown as being received within the medical implant delivery lumen of the outer delivery catheter 200. The guide wire 50 can extend through the guide wire lumen 220 of the outer delivery catheter 200. The medical implant device 350 can be positioned on the distal portion 302 of the medical implant delivery catheter 300. The expandable anchor 250 is shown in FIGS. 8A and 8B in an expanded state. As described herein, the medical implant delivery catheter 300 can be pre-loaded into the outer delivery catheter 200 such that medical implant delivery catheter 300 can be advanced together with the outer delivery catheter 200 into the desired vessel, channel, chamber and/or organ. FIG. 8A shows the medical implant delivery catheter 300 pre-loaded in a first retracted configuration, and FIG. 8B shows the medical implant delivery catheter 300 pre-loaded in a second retracted configuration. As shown in FIG. 8A, in the first retracted configuration, the distal end 310 of the medical implant delivery catheter 300 is distal of the side outlet opening 214. For example, prior to deploying the medical implant delivery catheter 300, such as while advancing the outer delivery catheter 200 along the guide wire 50 to the desired location, the distal end 310 can be distal of the side outlet opening 214. In some embodiments, the distal end 310 can be distal of and adjacent to (e.g., adjacent to and in contact with) the side outlet opening 214. The medical implant delivery catheter 300 can be translated proximally relative to the outer delivery catheter 200 to extend the distal end 310 through the side outlet opening 214 for deployment of the medical implant delivery catheter 300. Referring to FIG. 8B, the distal end 310 of the medical implant delivery catheter 300 can be positioned proximal of the side outlet opening 214. In some embodiments, the distal end 310 can be proximal of and adjacent to (e.g., adjacent to and in contact with) the side outlet opening 214. To deploy the medical implant delivery catheter 300, the medical implant delivery catheter 300 can be translated distally relative to the outer delivery catheter 200. The distal end 310 can be adjacent to the side outlet opening 214 to reduce or minimize the distance needed to advance or retract the medical implant delivery catheter 300 for deployment.

In some embodiments, the guide wire lumen of the outer delivery catheter 200 can extend along an off-center longitudinal axis. Referring to FIG. 9, a lateral cross-sectional view is shown of the outer delivery catheter 200. The lateral cross section can be taken along a plane which is perpendicular or substantially perpendicular to a longitudinal axis of the outer delivery catheter 200. The lateral cross section can include a width of the outer delivery catheter 200. As shown, the guide wire lumen 220 can extend off-set from the central longitudinal axis (C) of the outer delivery catheter 200. The medical implant delivery catheter 300 (not shown) can thereby be advanced through the outer delivery catheter 200 off-set from the central longitudinal axis (C). For example, the medical implant delivery lumen can be offset from the central longitudinal axis (C). The off-center guide wire lumen 220 can reduce or prevent axial rotation of the medical implant delivery catheter 300 while the medical implant delivery catheter 300 is positioned within the lumen 220. For example, advancing the medical implant delivery catheter 300 along a path off-set from the central longitudinal axis (C) can facilitate maintaining axial rotation orientation of the medical implant delivery catheter 300 while the medical implant delivery catheter 300 is extended through tortuous anatomical pathways. Maintaining a desired rotational orientation of the medical implant delivery catheter 300 can facilitate a desired exit trajectory of the medical implant delivery catheter 300 as the medical implant delivery catheter 300 is extended through the side outlet opening 214 (not shown). Maintaining a desired exit trajectory of the medical implant delivery catheter 300 can facilitate effective puncturing of the tissue at the target tissue site using the puncture needle 400 (not shown).

Figures 10A, 10B:
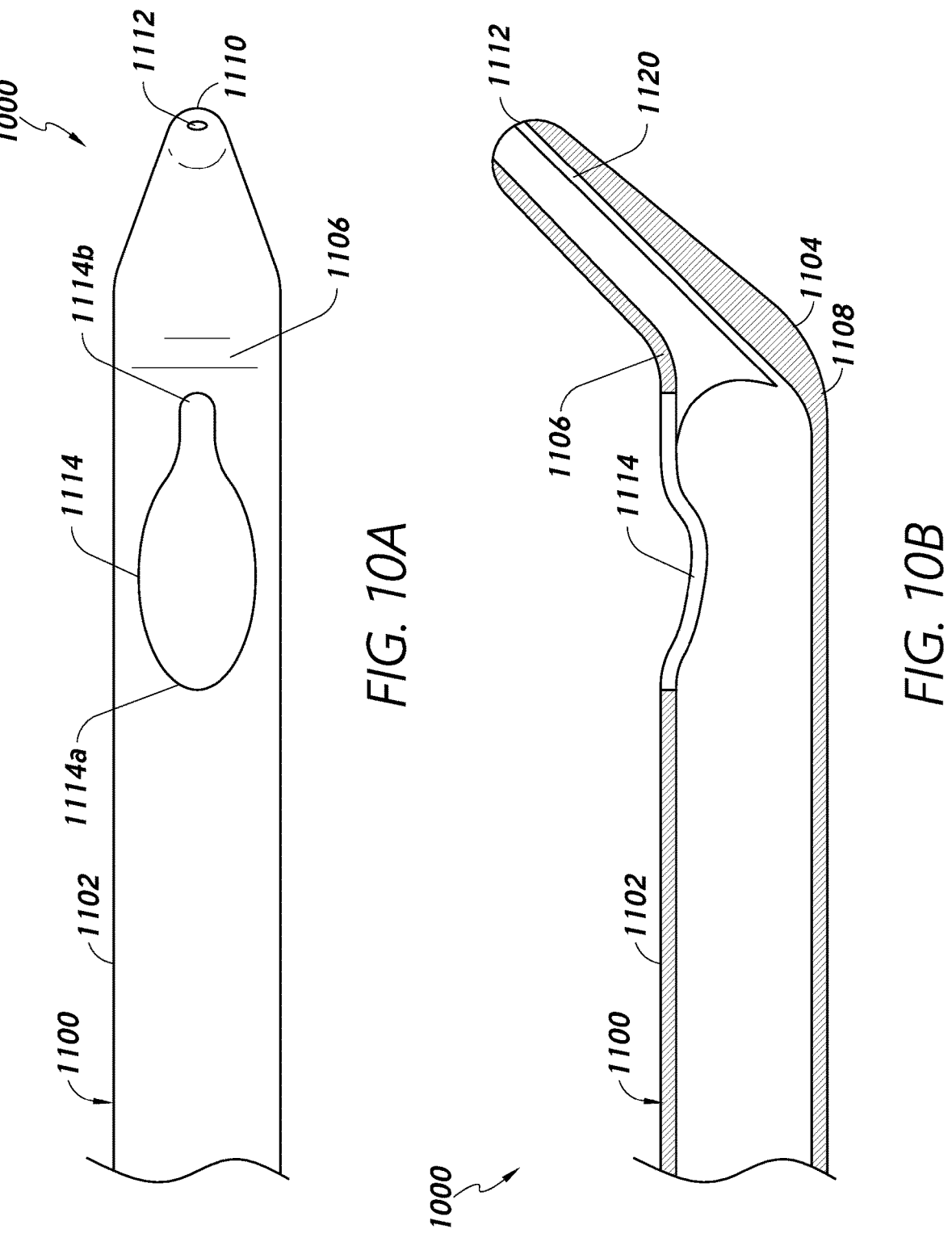
FIG. 10A is a top-down view.
FIG. 10B is a longitudinal cross-sectional view, of an outer delivery catheter of an example of a medical implant delivery system in accordance with one or more embodiments.
Figures 10C, 10D:
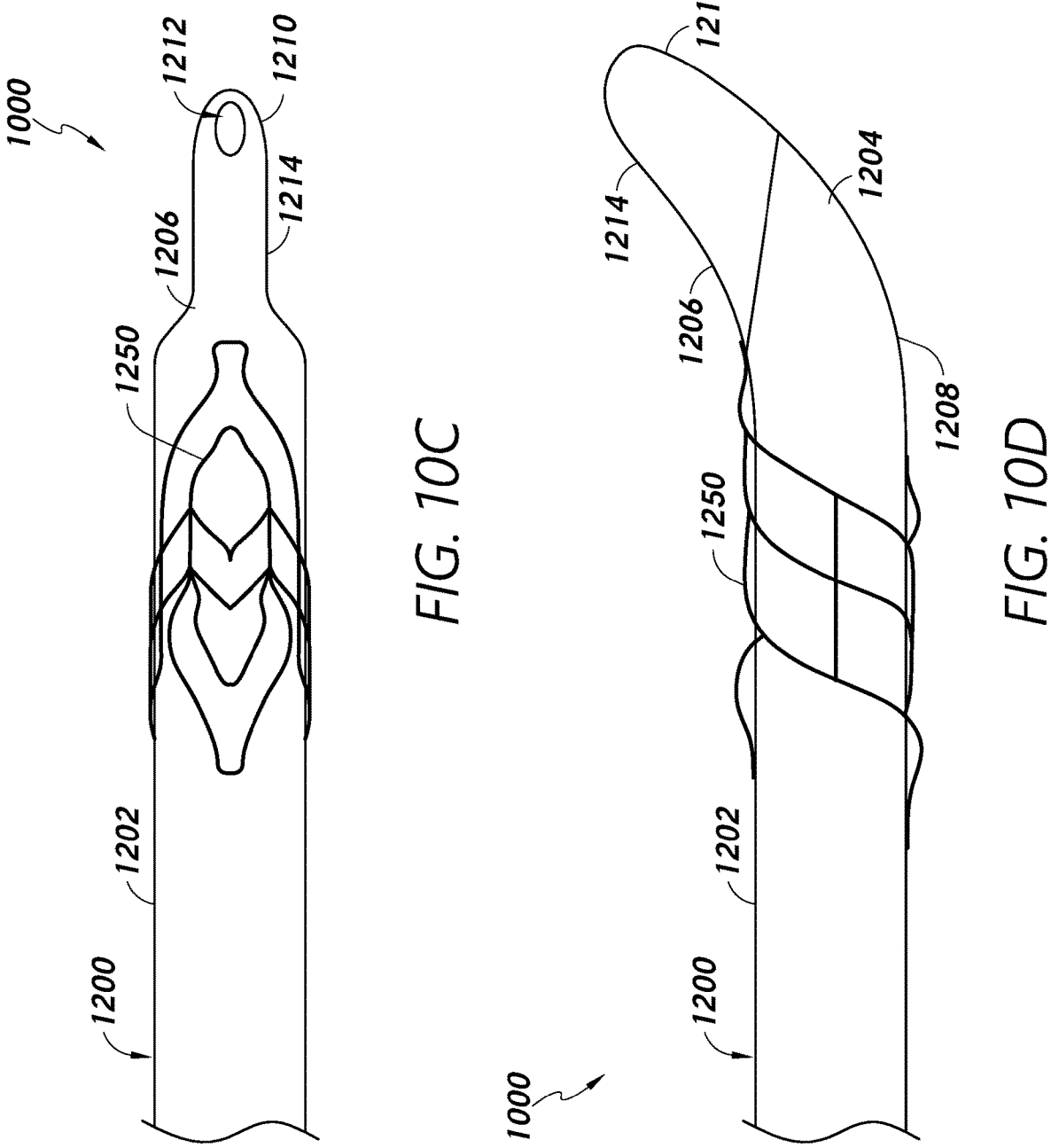
FIGS. 10C and 10D provide top-down and side views, respectively, of a medical implant delivery catheter of the medical implant delivery system of FIGS. 10A and 10B, in accordance with one or more embodiments.

FIGS. 10A through 10D show another example of a medical implant delivery system 1000. The medical implant delivery system 1000 can comprise an outer delivery catheter 1100 and a medical implant delivery catheter 1200. At least a portion of the medical implant delivery catheter 1200 can be slidably received within the outer delivery catheter 1100. In some embodiments, at least a portion of the medical implant delivery catheter 1200 can be passed through at least a portion of the outer delivery catheter 1100. FIG. 10A is a top-down view of the outer delivery catheter 1100, and FIG. 10B is a side cross-sectional view of the outer delivery catheter 1100. FIG. 10C is a top-down view of the medical implant delivery catheter 1200 and FIG. 10D is a side view of the medical implant delivery catheter 1200. A puncture needle (not shown) can be slidably received within the medical implant delivery catheter 1200. The puncture needle can be configured to be extended through a puncture needle outlet opening 1212 associated with a distal portion 1202, including a distal end 1210, of the medical implant delivery catheter 1200. In some embodiments, at least a portion of the puncture needle can be passed through at least a portion of the medical implant delivery catheter 1200 and extended through the puncture needle outlet opening 1212.

In some embodiments, the medical implant delivery catheter 1200 can be pre-loaded within the outer delivery catheter 1100. In some embodiments, the puncture needle can be pre-loaded within the medical implant delivery catheter 1200. The medical implant delivery system 1000 may or may not be used in combination with a puncture needle sheath. For example, the puncture needle sheath may extend slidably within the puncture needle lumen of the medical implant delivery catheter 1200 and the puncture needle may extend slidably within a lumen of the puncture needle sheath. The puncture needle may be pre-loaded within the puncture needle sheath and the puncture needle sheath may be pre-loaded within the medical implant delivery catheter 1200. Alternatively, the medical implant delivery catheter 1200, puncture needle and/or puncture needle sheath may not be pre-loaded.

A distal portion 1102 of the outer delivery catheter 1100 can comprise a side outlet opening 1114. Deployment of the medical implant delivery catheter 1200 can include extending the medical implant delivery catheter 1200 through the side outlet opening 1114. The distal portion 1102 can comprise a pre-formed curvature 1104. The pre-formed curvature 1104 can be configured to facilitate positioning of the outer delivery catheter 1100 into a vessel, channel, chamber and/or organ so as to access the target tissue site. The side outlet opening 1114 can be on an inner edge 1106 of the pre-formed curvature 1104. While the outer delivery catheter 1100 is positioned in a desired orientation at the target position, the inner edge 1106 can be oriented toward the target tissue site. An outer edge 1108 of the pre-formed curvature 1104 can be oriented away from the target tissue site, such as toward an opposing position relative to the target tissue site. The distal portion 1202 of the medical implant delivery catheter 1200 can comprise a pre-formed curvature 1204. In some embodiments, the pre-formed curvature 1204 can have the same orientation as the pre-formed curvature 1104 when the medical implant delivery catheter 1200 is in the deployed configuration, such as when the distal portion 1202 is extended beyond the side outlet opening 1114. The pre-formed curvature 1204 can be configured to facilitate access to the target tissue site while the outer delivery catheter 1100 is positioned at the target position. In some embodiments, the outer delivery catheter 1100 and/or the medical implant delivery catheter 1200 can be flexible such that the outer delivery catheter 1100 and/or medical implant delivery catheter 1200 can conform to the shape of anatomical pathways as the medical implant delivery system 1000 is advanced through tortuous pathways. In some embodiments, the medical implant delivery catheter 1200 can comprise a reduced curvature configuration while retracted within the outer delivery catheter 1100. In some embodiments, the medical implant delivery catheter 1200 can comprise a linear or substantially linear configuration while retracted within the outer delivery catheter 1100 and assume the curved configuration after release from the outer delivery catheter 1100. In some embodiments, the medical implant delivery catheter 1200 and/or the outer delivery catheter 1100 can comprise shape memory material, such as the distal portions 1202, 1102.

The side outlet opening 1114 can have a shape to facilitate extension of the medical implant delivery catheter 1200 through the side outlet opening 1114 in a desired orientation. For example, a distal portion 1202 of the medical implant delivery catheter 1200 can be configured to interlock with the side outlet opening 1114 as the distal portion 1202 is extended through the side outlet opening 1114. In some embodiments, the side outlet opening 1114 can comprise an asymmetry around a central axis. The asymmetry can reduce or prevent rotation of the distal portion 1202 as the distal portion 1202 is extended through the side outlet opening 1114. The distal portion 1202 can comprise a corresponding shape to interlock with the shape of the side outlet opening 1114. For example, the distal portion 1202 can comprise a configuration configured to interlock with the asymmetry of the side outlet opening 1114 as at least a portion of the distal portion 1202 is advanced through the side outlet opening 1114. In some embodiments, a shape of the distal portion 1202 can match, for example being the same or similar as, a shape of the side outlet opening 1114. Matching between the shapes of the distal portion 1202 and the side outlet opening 1114 can facilitate interlocking between the two.

The side outlet opening 1114 can comprise a proximal portion 1114a and a distal portion 1114b. The proximal portion 1114a and/or the distal portion 1114b can comprise a shape to interlock with the distal portion 1202. In some embodiments, the distal portion 1114b can have a width narrower than that of the proximal portion 1114a. In some embodiments, the distal portion 1114b can comprise an elongated extension. In some embodiments, the distal portion 1114b can have a "v" shape. In some embodiments, the proximal portion 1114a can comprise a segment of a circle. In some embodiments, the proximal portion 1114a can comprise a segment of an oval.

In some embodiments, the distal portion 1202 of the medical implant delivery catheter 1200 can comprise a shape which interlocks with the shape of the side outlet opening 1114. The distal portion 1202 can comprise a lateral cross section which has a shape configured to interlock with a shape of the side outlet opening 1114, where the lateral cross section can extend along a lateral dimension of the distal portion of the outer delivery catheter 1100. In some embodiments, a cross-sectional shape, such as a shape of a lateral cross section, of the distal portion 1202 can have a shape configured to interlock with the shape of the side outlet opening 1114 to orient the medical implant delivery catheter 1200 as the delivery catheter 1200 is extended through the side outlet opening 1114. The distal portion 1202 can be rotated prior to extending the distal portion 1202 through the side outlet opening 1114 to properly orient the distal portion 1202 relative to the side outlet opening 1114, for example matching a shape of the lateral cross section of the distal portion 1202 with a shape of the side outlet opening 1114. In some embodiments, the lateral cross section can be taken along a plane which divides the medical implant delivery catheter 1200 into an upper portion and a lower portion, the upper portion comprising the inner edge 1206 of the pre-formed curvature 1204 and the lower portion comprising the outer edge 1208 of the pre-formed curvature 1204. The lateral cross section can be taken along a lateral cross-sectional plane which extends along a longitudinal axis of the medical implant delivery catheter 1200 and which is parallel or substantially parallel to a plane containing at least a portion of the side outlet opening 1114. For example, the lateral cross section can bisect the medical implant delivery catheter 1200 into the upper portion and the lower portion. For example, the distal portion 1202 can comprise a narrowed distal end portion 1214. The narrowed distal end portion 1214 can be oriented towards and/or align with the distal portion 1114b of the side outlet opening 1114 so as to guide the orientation of the medical implant delivery catheter 1200 as the medical implant delivery catheter 1200 is extended through the side outlet opening 1114. For example, interlocking the distal portion 1202 and the side outlet opening 1114 can enable orienting the inner edge 1206 of the pre-formed curvature 1204 proximally and the outer edge 1208 of the pre-formed curvature 1204 distally as the distal portion 1202 is deployed.

The medical implant delivery system 1000 can comprise other features the same as or similar to those of the medical implant delivery system 100, such as described with reference to FIGS. 3 through 9. For example, a puncture needle (not shown) can be received in a puncture needle lumen of the medical implant delivery catheter 1200. The puncture needle can be extended through the puncture needle outlet opening 1212 associated with the distal end 1210 of the medical implant delivery catheter 1200 for puncturing tissue at the target tissue site. A medical implant device 1250 can be positioned on the distal portion 1202 such that a delivery catheter for delivering the puncture needle does not need to be exchanged for a delivery catheter for delivering the medical implant device 1250. The medical implant device 1250 can be deployed into the tissue opening formed by the puncture needle. The outer delivery catheter 1100 can comprise a guide wire lumen 1120 configured to receive a guide wire. The guide wire can extend through a guide wire outlet opening 1112 associated with a distal end 1110 of the outer delivery catheter such that the outer delivery catheter 1100 can be advanced along the guide wire for positioning into the desired vessel, channel, chamber and/or organ. For example, the medical implant delivery system 1000 can be configured for positioning into the coronary sinus from the right atrium via the coronary sinus ostium such that the puncture needle extending through the medical implant delivery catheter 1200 can be used to form an opening on a portion of the left atrial wall accessible from within the coronary sinus. The medical implant device 1250 can be a shunt device. The shunt device can be deployed into the opening for treating elevated atrial pressure. The medical implant delivery catheter 1200 can be advanced further into the opening formed in the left atrial wall such that the medical implant device 1250 can be positioned into the opening.

Figure 11:
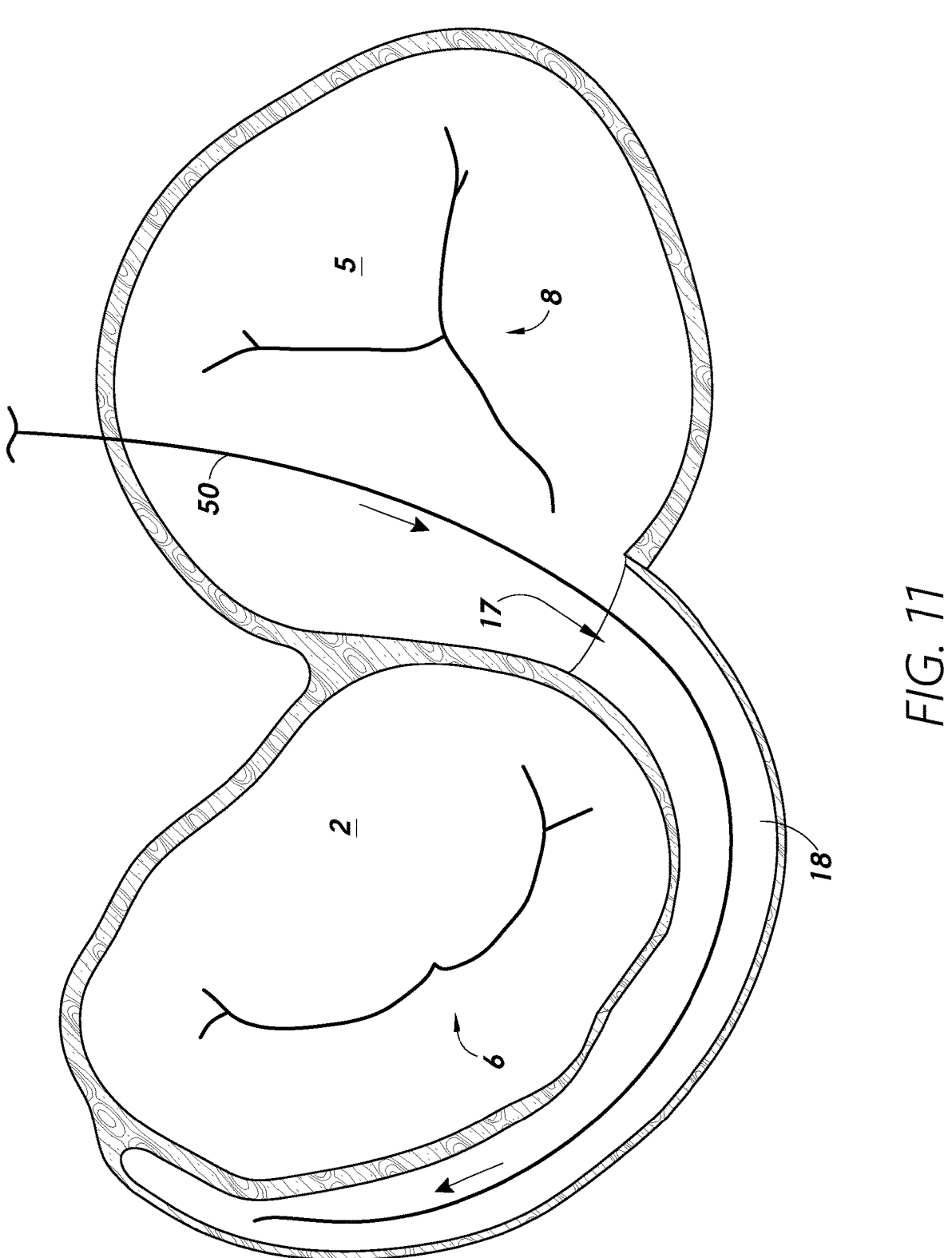
FIG. 11 shows insertion of a guide wire into the coronary sinus, in accordance with one or more embodiments.

FIGS. 11 through 16 show various steps of an example of a process for deploying the medical implant device 350 using the medical implant delivery system 100 as described herein. Referring to FIG. 11, the guide wire 50 can be inserted from the right atrium 5, through the coronary sinus ostium 17 and into the coronary sinus 18. The right atrium 5 can be accessed via the superior vena cava or via the inferior vena cava. For example, a transjugular or transsubclavian approach can be used to access the right atrium 5 via the superior vena cava. The medical implant delivery system 100 can be inserted into the subclavian veins or jugular veins, and advanced into the superior vena cava. Alternatively, a transfemoral approach can be used to position the medical implant delivery system 100 into the inferior vena cava.

Figure 12:
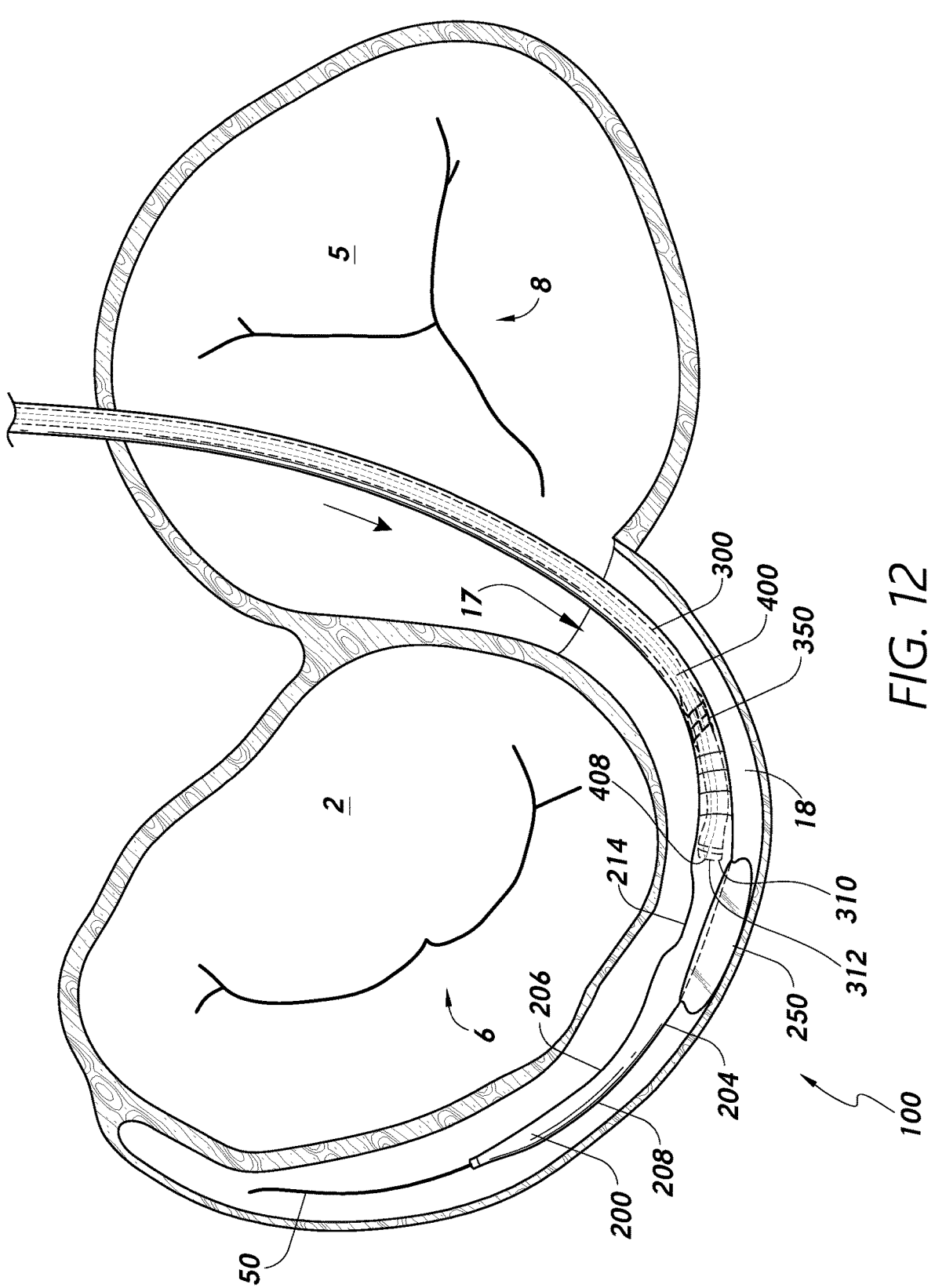
FIG. 12 shows advancement of the medical implant delivery system of FIG. 3 into the coronary sinus, in accordance with one or more embodiments.

As shown in FIG. 12, the medical implant delivery system 100 can be advanced along the guide wire 50 into the coronary sinus 18. The medical implant delivery system 100 can be advanced along the guide wire 50 until the medical implant delivery system 100 is at a desired location relative to the left atrial wall. For example, the outer delivery catheter 200 can be advanced along the guide wire 50 to position the side outlet opening 214 at or proximate to the target tissue site on the left atrial wall. The pre-formed curvature 204 of the outer delivery catheter 200 can be positioned to follow the curvature of the coronary sinus 18. For example, the pre-formed curvature 204 can be positioned such that the inner edge 206 of the pre-formed curvature 204 is oriented towards a portion of the left atrial wall and the outer edge 208 of the curvature is oriented towards an opposing portion of a wall of the coronary sinus 18.

As described herein, in some embodiments, the medical implant delivery system 100 can have the expandable anchor 250 on the outer edge 208 of the curvature 204. After the outer delivery catheter 200 is positioned at the desired location, the expandable anchor 250 can be triggered and/or actuated to assume an expanded configuration. In the expanded configuration, the expandable anchor 250 can contact a wall of the coronary sinus 18 to push the outer delivery catheter 200 toward the left atrial wall. For example, the expandable anchor 250 can contact the wall of the coronary sinus 18 such that the outer delivery catheter 200 can be positioned against the wall of the left atrium 2, thereby facilitating stably positioning the medical implant delivery system 100 at the desired location. In some embodiments, the inner edge 206 of the pre-formed curvature 204 can contact the left atrial wall such that the side outlet opening 214 is positioned at and/or surrounding the target tissue site. In some embodiments, the inner edge 206 may not contact the left atrial wall while the expandable anchor 250 is in the expanded state.

As shown in FIG. 12, the medical implant delivery catheter 300 can be pre-loaded within the medical implant delivery catheter lumen of the outer delivery catheter 200, and the puncture needle 400 can be pre-loaded within the puncture needle lumen of the medical implant delivery catheter 300. While advancing the outer delivery catheter

200 to the desired location, the medical implant delivery catheter 300 can be received within the medical implant delivery catheter lumen of the outer delivery catheter 200. For example, the distal end 310 of the medical implant delivery catheter 300 can be received within the medical implant delivery catheter lumen while the outer delivery catheter 200 is being advanced to the desired location. The puncture needle 400 can be pre-loaded within the puncture needle lumen of the medical implant delivery catheter 300 such that the puncture component 408 is positioned within the puncture needle lumen, or alternatively, such that the puncture component 408 extends through the puncture needle outlet opening 312 associated with the distal end 310 of the medical implant delivery catheter 300. While being advanced to the target tissue site, the puncture component 408 can extend through the puncture needle outlet opening 312 and remain within the medical implant delivery catheter lumen of the outer delivery catheter 200.

Figure 13:
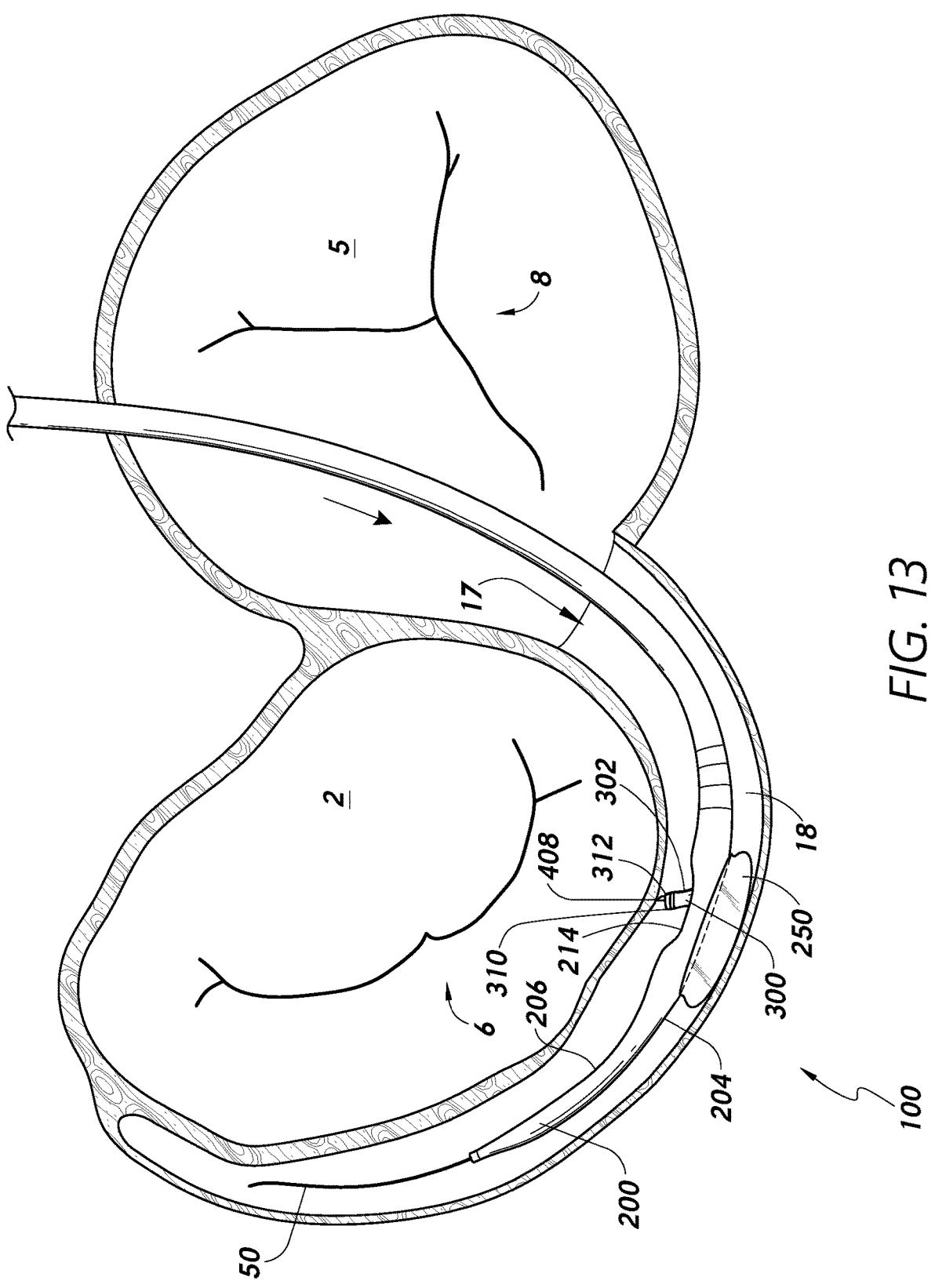
FIG. 13 shows use of the puncture needle of the medical implant delivery system of FIG. 3 to puncture tissue at the target tissue site on the left atrial wall, in accordance with one or more embodiments.

Referring to FIG. 13, after the outer delivery catheter 200 is positioned at the desired location, the medical implant delivery catheter 300 can be extended through the side outlet opening 214. After the outer delivery catheter 200 is positioned at the desired location, the distal portion 302 of the medical implant delivery catheter 300, including the distal end 310, can be extended through the side outlet opening 214. In some embodiments, the distal portion 302 can be rotated to properly orient the distal portion 302 relative to the side outlet opening 214 prior to extending the distal portion 302 through the side outlet opening.

As described herein, the puncture needle 400 can be pre-loaded within the puncture needle lumen of the medical implant delivery catheter 300. The puncture needle can be pre-loaded such that the puncture component 408 extends through the puncture needle outlet opening 312 associated with the distal end 310. The implant delivery catheter 300 can be extended through the side outlet opening 214 such that the puncture component 408 can be used to contact the wall of the left atrium 2 to puncture the tissue. In some embodiments, the puncture needle 400 can be extended further to complete formation of the opening. In some embodiments, the puncture component 408 can be received within the puncture needle lumen of the implant delivery catheter 300 while the outer delivery catheter 200 is inserted to the desired location. The puncture component 408 can be subsequently extended through the puncture needle outlet opening 312 such that the puncture component 408 can be used to contact the target tissue site.

The pre-formed curvature 304 (not shown) of the medical implant delivery catheter 300 can provide a desired trajectory for the distal portion 302 (not shown) of the medical implant delivery catheter 300 as it is advanced through the side outlet opening 214. For example, the pre-formed curvature 304 can facilitate contact between the puncture needle 400 and the target tissue site on the left atrial wall at a lateral position relative to the medical implant delivery system 100. The pre-formed curvature 304 can facilitate subsequent insertion of the distal portion 302 into the opening formed at the target tissue site. The pre-formed curvature 410 (not shown) of the puncture needle 400 can facilitate insertion of the distal portion 404 (not shown) of the puncture needle 400 into the tissue at the target tissue site, thereby providing effective puncture of tissue at the target site at a lateral position relative to the medical implant delivery system 100.

As described herein, the expandable anchor 250 can assume the expanded configuration after the outer delivery catheter 200 is positioned at a desired location within the coronary sinus 18. In some embodiments, expansion of the expandable anchor 250 can facilitate reliable positioning of the outer delivery catheter 200 against a wall of the coronary sinus. In some embodiments, the outer delivery catheter 200 can be pushed toward the left atrial wall, for example such that the inner edge 206 of the pre-formed curvature 204 can contact the left atrial wall. In some embodiments, positioning of the outer delivery catheter 200 against the left atrial wall can facilitate puncturing of the tissue using the puncture component 408 when the puncture needle 400 is extended through the side outlet opening 214. In some embodiments, the medical implant delivery system 100 may not include the expandable anchor 250 and/or the inner edge 206 is not positioned in contact with the left atrial wall. For example, the puncture needle 400 can be advanced further through the side outlet opening 214, such as compared to the extent to which the puncture needle 400 is advanced if the expandable anchor 250 is used, such that the puncture component 408 can contact the left atrial wall and push against the left atrial wall so to pierce the tissue at the target tissue site.

In some embodiments, the medical implant delivery system 100 can comprise a puncture needle sheath. The puncture needle 400 can extend along a puncture needle lumen of the puncture needle sheath. The puncture needle sheath can be received within the medical implant delivery catheter 300. For example, at least a portion of the puncture needle sheath can be configured to be passed through at least a portion of the puncture needle lumen of the medical implant delivery catheter 300 and at least a portion of the puncture needle 400 can be passed through at least a portion of a lumen of the puncture needle sheath. In some embodiments, the medical implant delivery system 100 can comprise a radially expandable member associated with a distal portion of the puncture needle sheath, the radially expandable member being configured to enlarge the opening formed in the tissue. The distal portion of the puncture needle sheath can be advanced through the opening such that at least a portion of the radially expandable member is positioned within the opening. The radially expandable member can subsequently be triggered and/or actuated to assume an expanded configuration so as to provide desired enlargement of the opening. The radially expandable member can be deflated and retracted from the opening after desired enlargement is accomplished. In some embodiments, the distal portion 302 of the medical implant delivery catheter 300 can be inserted into the opening to enlarge the opening, for example without using a radially expandable member associated with a puncture needle sheath. In some embodiments, both the radially expandable member and the distal portion 302 of the medical implant delivery catheter 300 can be used to enlarge the opening.

Figure 14:
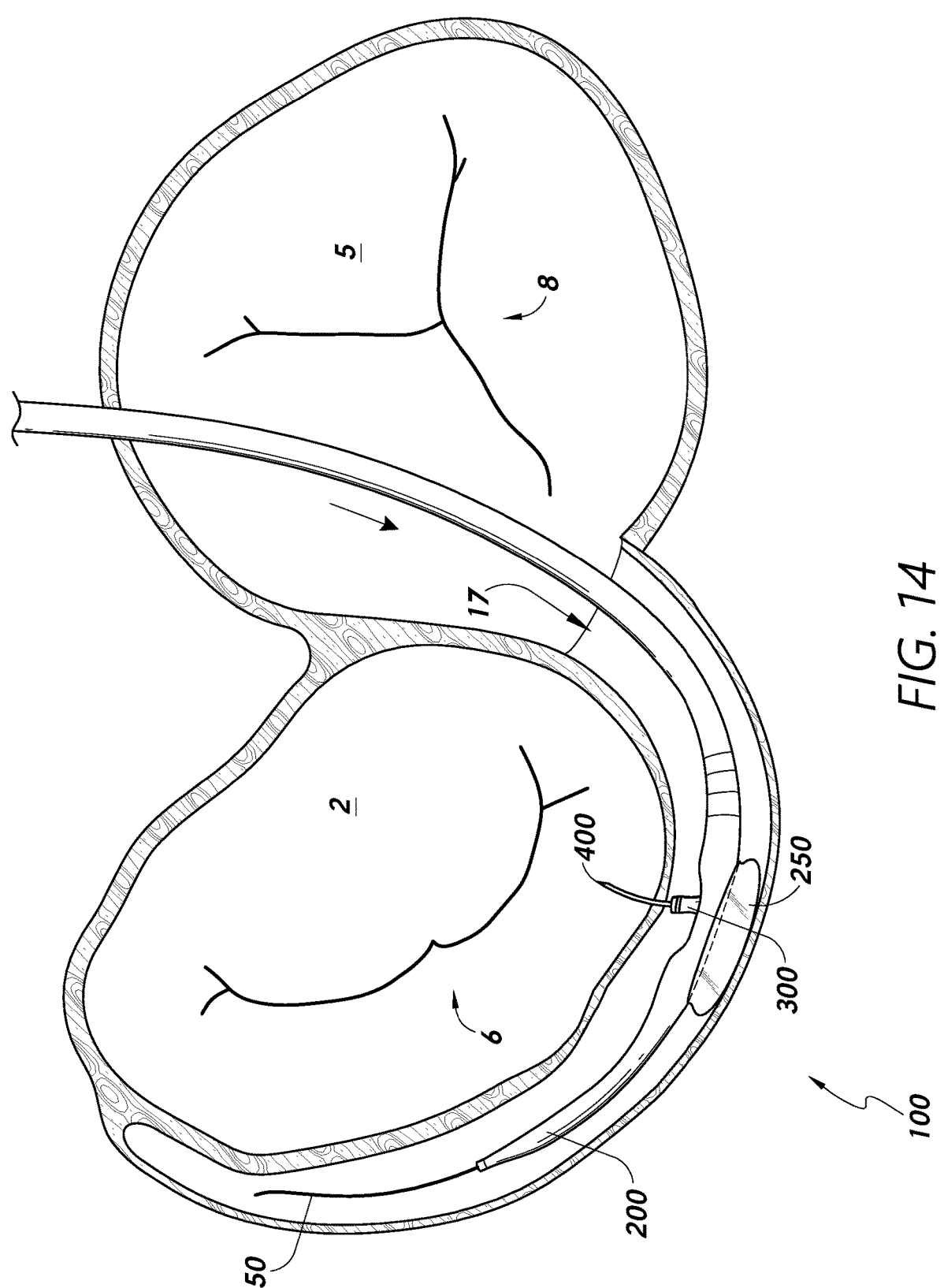
FIG. 14 shows the puncture needle of the medical implant delivery system of FIG. 3 inserted into the left atrium, in accordance with one or more embodiments.

Referring to FIG. 14, as described herein, in some embodiments, the puncture needle 400 can be extended into the left atrium 2 to serve as a guide wire along which the medical implant delivery catheter 300 can be advanced so as to deploy the medical implant device 350. Alternatively, the puncture needle 400 can be retracted after the opening in the left atrial wall is formed. The puncture needle 400 can be exchanged for a medical implant guide wire. The medical implant guide wire can be advanced through the puncture needle lumen of the medical implant delivery catheter 300 into the left atrium 2. In some embodiments, the medical implant guide wire can be advanced through a puncture needle sheath extending through the puncture needle lumen. In some embodiments, the puncture needle 400 can be exchanged for the medical implant guide wire before or after desired enlargement of the opening on the left atrial wall is achieved. For example, the puncture needle 400 can be retracted and the medical implant guide wire can be inserted in its place prior to activating and/or triggering the radially expandable anchor.

Figure 15:
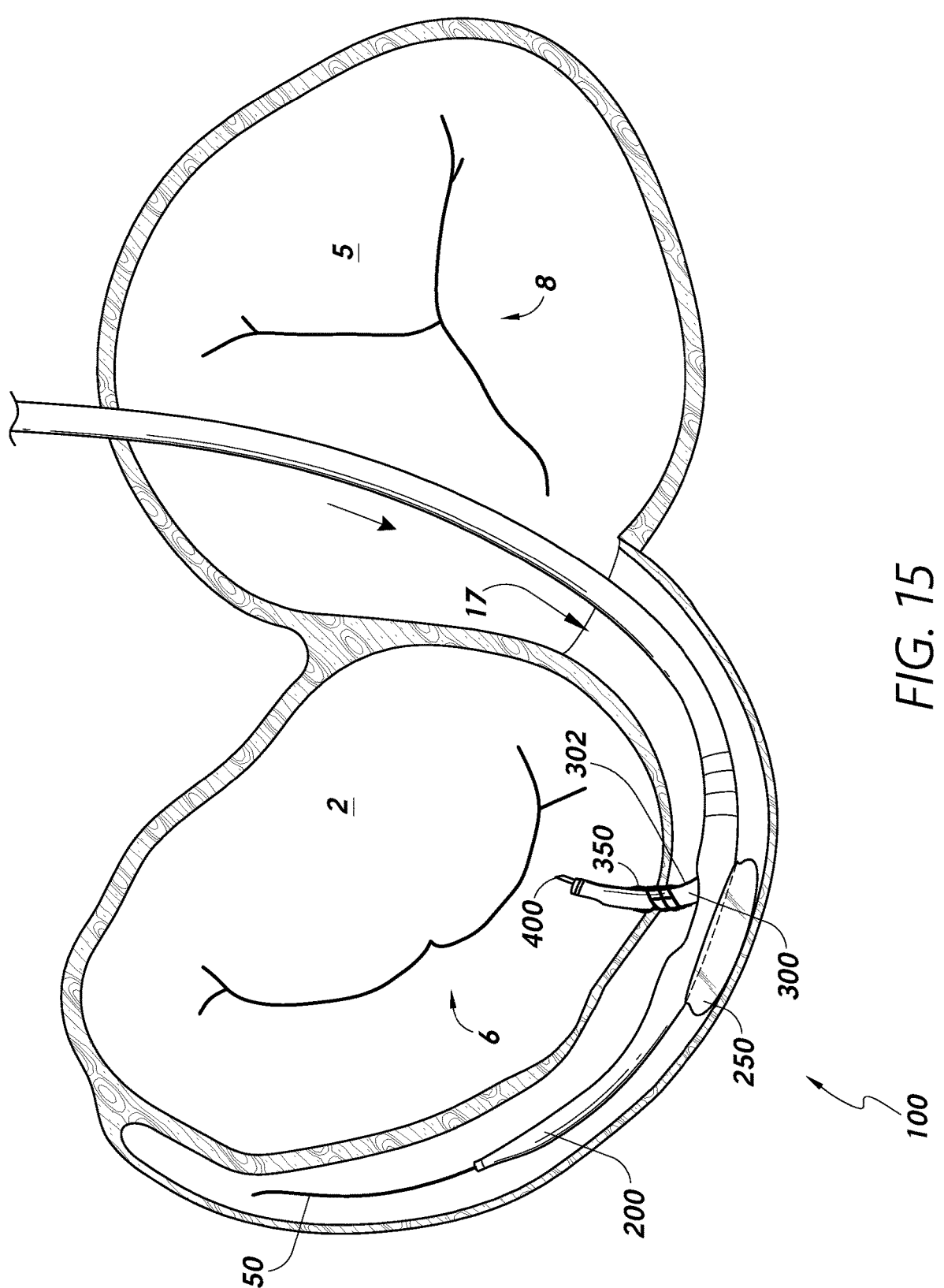
FIG. 15 shows deployment of a shunt device onto the left atrial wall using the medical implant delivery system of FIG. 3, in accordance with one or more embodiments.

FIG. 15 shows deployment of the medical implant device 350. The medical implant delivery catheter 300, such as the distal portion 302 of the medical implant delivery catheter 300, can be advanced through the opening in the left atrial wall such that the medical implant device 350 can be positioned into the opening. The medical implant delivery catheter 300 is shown as being advanced along the puncture needle 400 extended into the left atrium 2. As described herein, the medical implant device 350 can comprise an expandable shunt device. The expandable shunt device can be positioned into the opening for shunting blood flow from the left atrium 2 into the coronary sinus 18 so as to alleviate elevated left atrial pressure. Examples of processes for deploying an expandable shunt devices into the left atrial wall are provided in U.S. patent application Ser. No. 15/335,891, entitled "Systems for Deploying an Expandable Cardiac Shunt," which is incorporated herein in its entirety.

Figure 16:
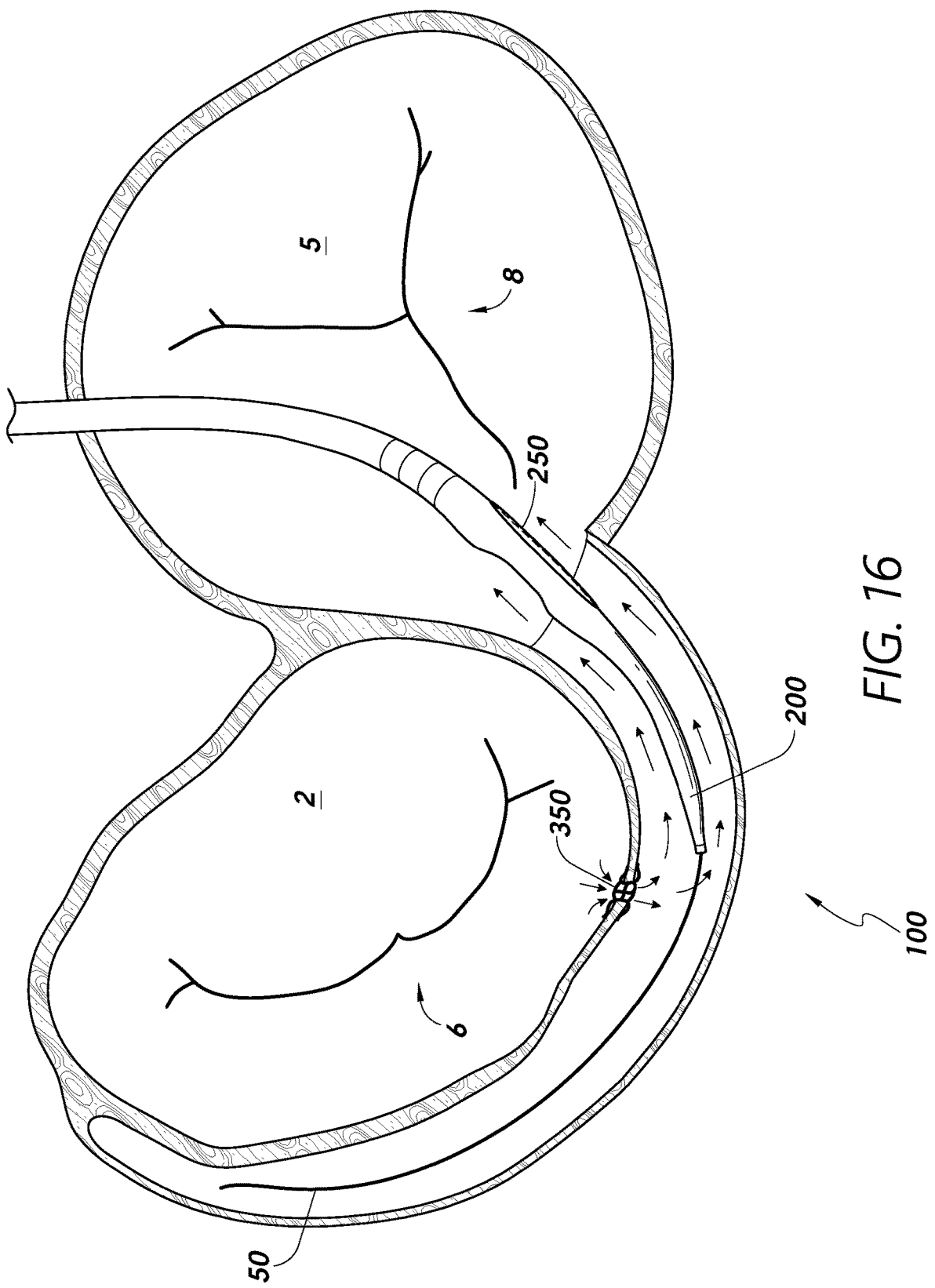
FIG. 16 shows withdrawal of the medical implant delivery system of FIG. 3 from the coronary sinus after deployment of the medical implant device onto the left atrial wall, in accordance with one or more embodiments.

FIG. 16 shows withdrawal of the medical implant delivery system 100 from the coronary sinus 18 along the guide wire 50, after the medical implant device 350 is positioned into the opening in the left atrial wall. As described herein, the medical implant device 350 can comprise an expandable shunt device. Referring to FIG. 16, the expandable shunt device deployed into the opening formed in the left atrial wall can allow flow of blood from the left atrium 2 into the coronary sinus 18. The blood flow can then drain into the right atrium 5. Creating a blood flow pathway from the left atrium 2 into the coronary sinus 18 can thereby alleviate elevated left atrial pressure. After the expandable shunt device is deployed into the left atrial wall, the puncture needle 400 (not shown) and the medical implant delivery catheter 300 (not shown) can be retracted back into the outer delivery catheter 200. For example, the puncture needle 400 can be retracted back into the puncture needle lumen of the medical implant delivery catheter 300 and the medical implant delivery catheter 300 can be retracted back into the outer delivery catheter 200. The expandable anchor 250 can assume a collapsed and/or deflated state prior to being withdrawn from the coronary sinus 8. Alternatively, in the case that a medical implant guide wire is used, the medical implant guide wire can be retracted. Subsequently, the outer delivery catheter 200 can be retracted along the guide wire 50 out of the coronary sinus.

FIG. 17 is a flow diagram of an example of a process 1600 to deploy a medical implant delivery system for delivering a medical implant device. The medical implant delivery system can comprise one or more features as described herein. The medical implant delivery system can comprise an outer delivery catheter, and a medical implant delivery catheter configured to extend through a lumen of the outer delivery catheter. The medical implant delivery system can comprise a puncture needle extending through a lumen of the medical implant delivery catheter. In block 1602, the process 1600 can involve advancing the medical implant delivery system along a guide wire into a vessel, channel, chamber and/or organ. For example, the medical implant delivery system can be positioned into the coronary sinus. The guide wire can be advanced into the coronary sinus and the medical implant delivery system can be advanced into the coronary sinus along the already positioned guide wire. The outer delivery catheter can comprise a guide wire lumen and the guide wire can slidably extend through the guide wire lumen.

In block 1604, the process 1600 can involve advancing the medical implant delivery catheter through a side outlet opening of outer delivery catheter. After the medical implant delivery system is positioned at a desired location within the coronary sinus, the medical implant delivery catheter can be deployed. For example, the medical implant delivery catheter can be extended through a side outlet opening of the outer delivery catheter such that the puncture needle can be used to pierce the tissue at the target tissue site. In block 1606, the process 1600 can involve extending the puncture component through a distal outlet opening of the medical implant delivery catheter to pierce tissue at the target tissue site to form an opening in the tissue. The target tissue site can be on a portion of the left atrial wall accessible from within the coronary sinus.

In block 1608, the process 1600 can involve extending a distal portion of medical implant delivery catheter through the opening formed in the tissue. The distal portion can be advanced through the opening to place the medical implant device into the opening. In some embodiments, the distal portion can be configured to enlarge the opening in the tissue. The distal portion can have a predetermined diameter to provide desired enlargement of the opening. In some embodiments, the medical implant delivery system can comprise a puncture needle sheath configured to be slidably passed through the puncture needle lumen of the medical implant delivery catheter, and the puncture needle is configured to be slidably passed through a lumen of the puncture needle sheath. A radially expandable member can be associated with a distal portion of the puncture needle sheath. The radially expandable member can be positioned within the opening formed at in the target tissue site wall to enlarge the opening when the radially expandable member is in an expanded configuration.

In block 1610, the process 1600 can involve deploying the medical implant device positioned on the medical implant delivery catheter into opening formed in tissue. For example, an expandable shunt device can be deployed into the opening formed on the left atrial wall.

FIGS. 18 through 20 show side views of another example of a medical implant delivery system 1700. Referring to FIG. 18, the medical implant delivery system 1700 can comprise an elongate housing 1800, a medical implant delivery catheter 1900 extending alongside the elongate housing 1800, and an outer sheath 2200 around the elongate housing 1800 and the medical implant delivery catheter 1900. A puncture needle sheath 2100 can slidably extend through a puncture needle lumen of the medical implant delivery catheter 1900. A puncture needle 2000 can slidably extend through the puncture needle sheath 2100. In some embodiments, the puncture needle 2000 can extend through the puncture needle lumen of the medical implant delivery catheter 1900 without the puncture needle sheath 2100.

A medical implant device 1950 can be positioned on the medical implant delivery catheter 1900. The medical implant device 1950 can be positioned on the medical implant delivery catheter 1900 such that a delivery catheter for delivering the puncture needle does not need to be exchanged for a delivery catheter for delivering the medical implant device 1950. In some embodiments, positioning the medical implant delivery catheter 1900 alongside the elongate housing 1800, for example rather than extending the medical implant delivery catheter 1900 through an outer delivery catheter, can provide improved maneuverability in deploying the medical implant delivery catheter 1900. The medical implant delivery catheter 1900 can be navigated along a tighter curve when deployed, such as to facilitate improved access to a target tissue site. The ability to advance the medical implant delivery catheter 1900 toward and/or into an opening formed in the target tissue without having to extend the medical implant delivery catheter 1900 through a side outlet opening of an outer delivery catheter can facilitate navigation through a tighter curve. Navigation through a tighter curve can thereby improve access to target tissue sites. For example, the ability to navigate through a narrower curvature can enable controlled puncture of target tissue and/or delivery of the medical implant device 1950 for patients with smaller and/or narrower anatomical features at and/or proximate to the target tissue site.

The elongate housing 1800 and the medical implant delivery catheter 1900 can be slidably positioned alongside one another. For example, the medical implant delivery catheter 1900 can be translated proximally and/or distally relative to the elongate housing 1800. In some embodiments, the elongate housing 1800 and the medical implant delivery catheter 1900 can be adjacent to and in contact with one another. The outer sheath 2200 can be around the elongate housing 1800 and the medical implant delivery catheter 1900 to maintain the position of the elongate housing 1800 and the medical implant delivery catheter 1900 alongside one another.

The medical implant delivery system 1700 can be advanced and/or retracted along the guide wire 50 to and/or from the target location. For example, the elongate housing 1800 can comprise a guide wire lumen extending therethrough configured to receive the guide wire 50. In some embodiments, the guide wire lumen can extend along an entire length of the elongate housing 1800 and extend through a guide wire outlet opening 1812 associated with a distal end 1810 of the elongate housing 1800.

The outer sheath 2200 is shown in FIG. 18 as being positioned proximal of the medical implant device 1950. For example, a distal end 2202 of the outer sheath 2200 is shown as being proximal of the medical implant device 1950. As described herein, the distal end 2202 can be positioned distal of the medical implant device 1950, such as while the medical implant delivery system 1700 is advanced to the target location. In some embodiments, the outer sheath 2200 can be maintained over the medical implant device 1950 prior to deployment of the medical implant delivery catheter 1900 and/or medical implant device 1950. The outer sheath 2200 can be slidable relative to the elongate housing 1800 and the medical implant delivery catheter 1900. The outer sheath 2200 can be translated proximally and/or distally relative to the medical implant delivery catheter 1900 and the elongate housing 1800. For example, the outer sheath 2200 can be translated proximally relative to the medical implant delivery catheter 1900 and the elongate housing 1800 to facilitate release a corresponding portion of the medical implant delivery catheter 1900 from being positioned adjacent to the elongate housing 1800. In some embodiments, after delivery of the medical implant device 1950, the outer sheath 2200 can be translated distally relative to the medical implant delivery catheter 1900 and the elongate housing 1800 to position the medical implant delivery catheter 1900 adjacent to and alongside the elongate housing 1800 prior to withdrawal of the medical implant delivery system 1700.

In some embodiments, a distal portion 1802 of the elongate housing 1800 can comprise a taper. A size of the distal portion 1802 can taper toward the distal end 1810. For example, a diameter of the elongate housing 1800 can narrow toward the distal end 1810. In some embodiments, the distal portion 1802 of the elongate housing 1800 can comprise a pre-formed curvature 1804. The pre-formed curvature 1804 and/or the taper in the distal portion 1802 can be configured to facilitate positioning of the elongate housing 1800 into a vessel, channel, chamber and/or organ so as to deliver a medical implant device and/or therapy to a target site accessible from within the vessel, channel, chamber and/or organ. A radius of curvature and/or a length of the pre-formed curvature 1804 can be selected based at least in part on a shape and/or dimension of the vessel, channel, chamber and/or organ, such as the coronary sinus. In some embodiments, the length of the pre-formed curvature 1804 can be predetermined based at least in part on a distance of the target tissue site from the coronary sinus ostium. In some embodiments, the radius of curvature of the pre-formed curvature 1804 can be predetermined based at least in part on a shape of the coronary sinus, including a degree of curvature of a portion of the coronary sinus in which the elongate housing 1800 is positioned. The radius of curvature of the pre-formed curvature 1804 can be selected such that the pre-formed curvature 1804 can conform or substantially conform to a curvature of the coronary sinus. For example, when positioned in the coronary sinus, the pre-formed curvature 1804 can be positioned such that the inner edge 1806 of the pre-formed curvature 1804 is oriented towards a portion of the left atrial wall and the outer edge 1808 of the pre-formed curvature 1804 is oriented towards an opposing portion of a wall of the coronary sinus. In some embodiments, the elongate housing 1800, including the distal portion 1802 can comprise a shape memory material. The distal portion 1802 can assume a reduced curvature configuration while being advanced to the target tissue site. The pre-formed curvature 1804 can assume the curved configuration after positioning in the target position. The tapering in the distal portion 1802 can facilitate insertion into narrower portions of the coronary sinus. In some embodiments, the distal portion 1802 can comprise one or more radiopaque markers thereon to facilitate visualization of positioning the elongate housing 1800 at the desired location within the vessel, channel, chamber and/or organ, such as the coronary sinus.

The elongate housing 1800 can comprise a recess 1814 configured to receive at least a portion of the medical implant delivery catheter 1900. The recess 1814 can extend along at least a portion of a length of the elongate housing 1800. For example, the recess 1814 can extend from a proximal portion, including a proximal end, to the distal portion 1802 of the elongate housing 1800. In some embodiments, a distal end 1816 of the recess 1814 can be proximal of the pre-formed curvature 1804. In some embodiments, the distal end 1816 of the recess 1814 can be on the pre-formed curvature 1804. The recess 1814 can open along the same side as the inner edge 1806 of the pre-formed curvature 1804.

In some embodiments, the elongate housing 1800 can comprise an expandable anchor 1850 on the distal portion 1802. The expandable anchor 1850 is shown in a deflated state in FIG. 18. In some embodiments, the expandable anchor 1850 can be on the same side as an outer edge 1808 of the pre-formed curvature 1804. In some embodiments, the expandable anchor 1850 can be on the pre-formed curvature 1804. For example, the expandable anchor 1850 can be on the outer edge 1808 of the pre-formed curvature 1804. In some embodiments, the expandable anchor 1850 can be on a portion of the elongate housing 1800 opposite the distal end 1816 of the recess 1814. In some embodiments, the expandable anchor 1850 can be on a portion of the elongate housing 1800 opposite and proximal of the pre-formed curvature 1804.

The expandable anchor 1850 can be inserted to or proximate to the target tissue site in a collapsed configuration. The expandable anchor 1850 can be subsequently triggered and/or actuated to assume an expanded configuration so as to contact tissue near the target tissue site to facilitate stable positioning of the elongate housing 1800 relative to the target tissue site. In some embodiments, expansion of the expandable anchor 1850 can facilitate reliable positioning of the elongate housing 1800 against tissue portion at a location opposite that of the target tissue site. In some embodiments, expansion of the expandable anchor 1850 can push the elongate housing 1800 and/or the medical implant delivery catheter 1900 against tissue adjacent to the target tissue site. Reliable positioning of the elongate housing 1800 at the target tissue site can facilitate desired deployment of the puncture needle 2000 to form the opening. In some embodiments, the elongate housing 1800 may not have an expandable anchor 1850. The puncture needle 2000 can be extended further, such as compared to the extent to which the puncture needle 2000 would be advanced if the expandable anchor 1850 is used, such that the puncture component 2008 can contact and push against the target tissue site to facilitate effective puncture of the tissue. For example, the puncture needle 2000 can be further extended to contact and push against the left atrial wall so as to pierce the tissue on the left atrial wall.

Referring again to FIG. 18, the distal portion 1902 of the medical implant delivery catheter 1900 can comprise a taper. A size of the distal portion 1902 can taper toward the distal end 1910, a diameter of the medical implant delivery catheter 1900 narrowing toward the distal end 1910. In some embodiments, the medical implant delivery catheter 1900 can have a pre-formed curvature 1904 on a distal portion 1902. The pre-formed curvature 1904 can have a same or similar orientation as the pre-formed curvature 1804 of the elongate housing 1800. For example, when the medical implant delivery catheter 1900 is positioned in the coronary sinus, an inner edge 1906 of the pre-formed curvature 1904 can be oriented towards the left atrial wall and an outer edge 1908 of the pre-formed curvature 1904 can be oriented towards a wall of the coronary sinus. In some embodiments, the pre-formed curvature 1904 can have a smaller radius of curvature than the pre-formed curvature 1804.

In some embodiments, the taper of the distal portion 1902 and/or the pre-formed curvature 1904 can facilitate accessing the target tissue site while the medical implant delivery system 1700 is positioned in the vessel, channel, chamber and/or organ. The taper can facilitate effective puncture of the target tissue site and/or deployment of the medical implant device 1950 positioned on the medical implant delivery catheter 1900. The distal portion 1902 can be further extended through the opening formed at the target tissue site, such that the medical implant device 1950 can be positioned within the opening and deployed. The taper in the distal portion 1902 can ease insertion of the distal portion 1902 through the opening formed in the tissue. The pre-formed curvature 1904 can enable the distal portion 1902 to follow a pre-determined trajectory to facilitate extending the distal portion 1902 through the opening.

The medical implant delivery catheter 1900 can comprise a puncture needle lumen configured to slidably receive the puncture needle 2000. The puncture needle 2000 can be extended through a puncture needle outlet opening 1912 associated with, the distal portion 1902, including a distal end 1910, of the medical implant delivery catheter 1900. In some embodiments, the pre-formed curvature 1904 can facilitate proper positioning of the puncture needle 2000 at the target tissue site as the medical implant delivery catheter 1900 is advanced relative to the elongate housing 1800. Proper positioning of the puncture needle 2000 can enable effective puncturing of the target tissue site.

In some embodiments, the medical implant delivery system 1700 can include a puncture needle sheath 2100 configured to allow the puncture needle 2000 to extend therethrough. The puncture needle 2000 can extend through a puncture needle outlet opening 2104 associated with a distal end 2106 of the puncture needle sheath 2100. The puncture needle sheath 2100 can slidably extend through the puncture needle lumen of the medical implant delivery catheter 1900. In some embodiments, at least a portion of the puncture needle sheath 2100 can be passed through at least a portion of the puncture needle lumen of the medical implant delivery catheter 1900. In some embodiments, at least a portion of the puncture needle 2000 can be passed through at least a portion of the lumen of the puncture needle sheath 2100. In some embodiments, a distal portion 2102 of the puncture needle sheath 2100 can have associated therewith a radially expandable member 2150 configured to enlarge the opening formed at the target tissue site. The radially expandable member 2150 can be triggered and/or actuated after it has been positioned into the opening to assume an expanded configuration so as to enlarge the opening. In some embodiments, the radially expandable member 2150 can comprise an inflatable balloon circumferentially positioned around the distal portion 2102 of the puncture needle sheath 2100.

In some embodiments, the distal portion 1902 of the medical implant delivery catheter 1900 can be configured to provide desired dilation of the opening. For example, the distal portion 1902 can be inserted into the opening to enlarge the opening. The distal portion 1902 can comprise a size and/or shape to facilitate dilation of the opening, for example, having a predetermined diameter configured to provide the desired enlargement. In some embodiments, the distal portion 1902 can be used to dilate the opening instead of the radially expandable member 2150. For example, the puncture needle sheath 2100 and/or the radially expandable member 2150 may not be included. In some embodiments, the puncture needle 2000 can be positioned within the puncture needle lumen of the medical implant delivery catheter 1900 without the puncture needle sheath 2100. In some embodiments, the distal portion of the puncture needle 2000 can be configured to enlarge the opening. The distal portion can be inserted into the opening to enlarge the opening. For example, the distal portion can have a predetermined diameter to provide desired enlargement of the opening. In some embodiments, one or more of the puncture needle 2000, the distal portion 1902 and the radially expandable member 2150 can be used to dilate the opening formed in the target tissue.

In some embodiments, the puncture needle 2000 can be exchanged for a medical implant guide wire. For example, the puncture needle 2000 can be retracted after the puncture needle 2000 has been used to pierce the tissue and the opening is formed. The medical implant guide wire can be advanced through the puncture needle lumen in place of the puncture needle 2000. The medical implant device 1950 can be advanced along the medical implant guide wire to the target tissue site. For example, an expandable shunt device can be advanced along the medical implant guide wire to an opening formed on the left atrial wall. In some embodiments, the medical implant guide wire can be advanced through the puncture needle sheath 2100. In some embodiments, the medical implant delivery system 1700 may not include the puncture needle sheath 2100. For example, the puncture needle 2000 and/or the medical implant guide wire can extend through the puncture needle lumen of the medical implant delivery catheter 1900 without the puncture needle sheath 2100.

The medical implant device 1950 can be positioned on the distal portion 1902 of the medical implant delivery catheter 1900. In some embodiments, the medical implant device 1950 can comprise a shunt device, including an expandable shunt device. As described in further detail herein, the distal portion 1902 can be further extended through the opening formed at the target tissue site, such that the medical implant device 1950 can be positioned within the opening and deployed. In some embodiments, the medical implant device 1950 can be positioned on the pre-formed curvature 1904. The medical implant device 1950 can be circumferentially positioned around the distal portion 1902, including on the pre-formed curvature 1904.

The expandable shunt device can have a number of configurations. In some embodiments, the expandable shunt device can comprise an expandable tubular shunt device. Examples of suitable expandable shunt devices for the medical implant delivery system 1700 are provided in U.S. patent application Ser. No. 15/335,891, entitled "Systems for Deploying an Expandable Cardiac Shunt," which is incorporated herein in its entirety.

FIG. 19 is a side view of the medical implant delivery system 1700 where the puncture needle 2000 is further extended through the puncture needle outlet opening 1912. A portion of the puncture needle 2000 is shown as being extended through puncture needle outlet opening 2104 associated with the distal end 2106 of the puncture needle sheath 2100. The puncture needle sheath 2100 is shown as being extended through the puncture needle outlet opening 1912 associated with the distal end 1910 of the medical implant delivery catheter 1900. The expandable anchor 1850 of the elongate housing 1800 is shown in an expanded state.

The puncture needle 2000 can comprise an elongate portion 2002. A distal portion 2004 of the elongate portion 2002 is shown extending through the puncture needle outlet opening 1912 of the medical implant delivery catheter 1900. The puncture needle 2000 can have a puncture component 2008 associated with a distal end 2006 of the elongate portion 2002, the puncture component 2008 being configured for tissue piercing. The puncture needle 2000 can comprise a pre-formed curvature 2010 on the distal portion 2004. The pre-formed curvature 2010 can have a same or similar orientation as the pre-formed curvature 1904 of the medical implant delivery catheter 1900. In some embodiments, the pre-formed curvature 2010 can have a smaller radius of curvature than the pre-formed curvature 1904. In some embodiments, the pre-formed curvature 2010 can have a same or similar orientation as the pre-formed curvature 1804 of elongate housing 1800. In some embodiments, the pre-formed curvature 2010 can facilitate effective tissue puncture at the target tissue site while the medical implant delivery system 1700 is positioned in the vessel, channel, chamber and/or organ.

In some embodiments, the distal portion 2004 of the puncture needle 2000 can comprise a shape memory material. The distal portion 2004 can remain within the medical implant delivery catheter 1900 prior to the medical implant delivery system 1700 being positioned at or proximate to the target tissue site and/or after the distal portion 2004 is retracted back into the medical implant delivery catheter 1900. In some embodiments, the pre-formed curvature 2010 can assume a less curved configuration while retracted within the medical implant delivery catheter 1900 and/or the puncture needle sheath 2100. In some embodiments, the distal portion 2004 can assume a linear or substantially linear configuration while received within the medical implant delivery catheter 1900 and/or the puncture needle sheath 2100. The pre-formed curvature 2010 on the distal portion 2004 can assume the curved configuration after extension of the distal portion 2004 through the puncture needle outlet opening 1912 and/or the puncture needle outlet opening 2104 associated with the distal end 2106 of the puncture needle sheath 2100.

FIG. 20 is another side view of the medical implant delivery system 1700. The outer sheath 2200 is positioned over the medical implant device 1950. For example, the medical implant device 1950 is not shown in FIG. 20 as the distal end 2202 of the outer sheath 2200 is distal of the medical implant device 1950, thereby extending over the medical implant device 1950. The distal end 1910 of the medical implant delivery catheter 1900 is shown as extending distally of the outer sheath 2200. The puncture needle 2000 and the puncture needle sheath 2100, including the radially expandable member 2150, are shown as extending from puncture needle outlet 1912 associated with the distal end 1910 of the medical implant delivery catheter 1900. The puncture needle 2000 is shown as extending from the puncture needle outlet opening 2104 associated with the distal end 2106 of the puncture needle sheath 2100.

In some embodiments, while the medical implant delivery catheter 1900 is in a retracted configuration, the outer sheath 2200 can be positioned over the distal end 1910 of the medical implant delivery catheter 1900. The distal end 2202 of the outer sheath 2200 can be at or distal of the distal end 1910 of the medical implant delivery catheter 1900. In some embodiments, the distal portion 1902 can comprise a shape memory material. For example, the pre-formed curvature 1904 can assume a less curved configuration, including a linear or substantially linear configuration, while the outer sheath 2200 is positioned around the pre-formed curvature 1904. The outer sheath 2200 positioned around the pre-formed curvature 1904 can maintain the pre-formed curvature 1904 in the linear or substantially linear configuration. In some embodiments, the outer sheath 2200, elongate housing 1800, and/or the medical implant delivery catheter 1900 can be flexible such that the outer sheath 2200, elongate housing 1800 and/or medical implant delivery catheter 1900 can conform to the shape of anatomical pathways as the medical implant delivery system 1700 is advanced through tortuous pathways. The outer sheath 2200 can maintain the medical implant delivery catheter 1900 in the recess 1814 of the elongate housing 1800. The outer sheath 2200 can be configured to be translated proximally relative to the implant delivery catheter 1900 to release the medical implant delivery catheter 1900. For example, the distal portion 1902 can be displaced from the recess 1814. The pre-formed curvature 1904 can be allowed to assume the curved configuration, such as after being released from the recess 1814. The medical implant delivery catheter 1900 can be distally translatable relative to the outer sheath 2200 and/or elongate housing 1800 to position the medical implant device into the opening formed in the tissue.

The expandable anchor 1850 is shown in FIG. 20 an expanded state. The expandable anchor 1850 can remain in a collapsed state until the medical implant delivery system 1700 is positioned at or proximate to the target tissue site. The expandable anchor 1850 can be in the collapsed state while the medical implant delivery catheter 1900 is in a retracted configuration. In some embodiments, while the medical implant delivery catheter 1900 is in the retracted configuration, the outer sheath 2200 can be positioned over the expandable anchor 1850. The distal end 2202 of the outer sheath 2200 can be distal of the expandable anchor 1850. In some embodiments, the outer sheath 2200 can remain proximal of the expandable anchor 1850 while the medical implant delivery catheter 1900 is in the retracted configuration.

In some embodiments, the puncture needle 2000 and/or the puncture needle sheath 2100 can be pre-loaded into the puncture needle lumen of the medical implant delivery catheter 1900. In some embodiments, a pre-loaded puncture needle 2000 and pre-loaded puncture needle sheath 2100 can remain within the medical implant delivery catheter 1900 until the medical implant delivery system 1700 is positioned at or proximate to the target tissue site. For example, the puncture component 2008 may not extend beyond the puncture needle outlet opening 1912 until the medical implant delivery system 1700 is positioned within the vessel, channel, chamber and/or organ. The puncture component 2008 can remain within the medical implant delivery catheter 1900 while the puncture needle 2000 is in a retracted configuration. In some embodiments, a portion of the puncture needle 2000 can extend through the puncture needle outlet opening 1912 while the puncture needle 2000 is in the retracted configuration. In some embodiments, the puncture component 2008 extending beyond the puncture needle outlet opening 1912 can be proximal of the distal end 2202 of the outer sheath 2200 when in the puncture needle 2000 is in the retracted configuration. For example, the puncture component 2008 can be received within the recess 1814 of the elongate housing 1800 until the medical implant delivery system 1700 is positioned into the desired vessel, channel, chamber and/or organ. In some embodiments, the puncture needle 2000 and/or the puncture needle sheath 2100 can be advanced from a proximal portion of the medical implant delivery catheter 1900 to the puncture needle outlet opening 1912 after the medical implant delivery system 1700 has been positioned in the desired vessel, channel, chamber and/or organ.

FIGS. 21 through 24 show various steps of an example of a process for delivering a medical implant device, such as an expandable shunt device, to a left atrial wall from within the coronary sinus using the medical implant delivery system 1700 as described herein. Referring to FIG. 21, the medical implant delivery system 1700 can be advanced along the guide wire 50 into the coronary sinus 18. As described herein, the guide wire 50 can be inserted from the right atrium 5, through the coronary sinus ostium 17 and into the coronary sinus 18. In some embodiments, a transjugular or trans-subclavian approach can be used to access the right atrium 5 via the superior vena cava. Alternatively, a trans-femoral approach can be used to position the medical implant delivery system 1700 through the inferior vena cava and into the right atrium 5. The medical implant delivery system 1700 can be positioned at a desired location within the coronary sinus 18. While the medical implant delivery system 1700 is advanced along the guide wire 50 to the desired location within the coronary sinus 18, the outer sheath 2200 can be positioned over the distal end 1910 (not shown) of the medical implant delivery catheter 1900 (not shown). The medical implant delivery catheter 1900 can be maintained within the recess 1814 of the elongate housing 1800. The outer sheath 2200 can be proximal of the expandable anchor 1850. In some embodiments, the outer sheath 2200 can be positioned over the expandable anchor 1850 while the medical implant delivery system 1700 is positioned to the desired location. In some embodiments, the distal end 2202 of the outer sheath 2200 can be at or distal of the distal end 1816 of the recess 1814 while the medical implant delivery system 1700 is advanced along the guide wire 50.

In FIG. 22, after the medical implant delivery system 1700 has been advanced to the desired location, the outer sheath 2200 can be translated proximally relative to the medical implant delivery catheter 1900 and the elongate housing 1800. The outer sheath 2200 can be slid proximally to release the distal portion 1902 of the medical implant delivery catheter 1900. The distal end 2202 of the outer sheath 2200 can be translated proximally such that at least a portion of the distal portion 1902 can be released from the recess 1814 of the elongate housing 1800. For example, the pre-formed curvature 1904 can assume its curved configuration after the distal portion 1902 is released. The inner edge 1906 of the pre-formed curvature 1904 can be oriented towards the wall of the left atrium 2 and the outer edge 1908 of the pre-formed curvature 1904 can be oriented towards a wall of the coronary sinus 18. As described herein, in some embodiments, the puncture needle 2000 can be pre-loaded such that the puncture component 2008 extends through the puncture needle outlet opening 1912 of the medical implant delivery catheter 1900. In some embodiments, the puncture component 2008 can extend beyond the puncture needle outlet opening 2104 of the puncture needle sheath 2100. For example, the puncture component 2008 can be extended beyond the puncture needle outlet opening 2104 and the puncture needle outlet opening 1912 while remaining proximal of the distal end 2202 of the outer sheath 2200 while the within the medical implant delivery system 1700 is advanced to its target location. Alternatively, the puncture component 2008 can be extended through the puncture needle outlet opening 1912 and/or the puncture needle outlet opening 2104 after the medical implant delivery system 1700 has been positioned at or proximate to the desired location. After the distal portion 1902 is released, the medical implant delivery catheter 1900 can be advanced distally such that the puncture component 2008 can contact the left atrial wall and can be used to pierce the tissue at the target tissue site on the left atrial wall. In some embodiments, the puncture needle sheath 2100 can be advanced, such as relative to the medical implant delivery catheter 1900, to facilitate contact between the puncture component 2008 and the left atrial wall. The puncture needle 2000 can be further advanced, such as relative to the medical implant delivery catheter 1900 and/or the puncture needle sheath 2100, to form the opening on the left atrial wall.

In some embodiments, the pre-formed curvature 1904 of the medical implant delivery catheter 1900 can facilitate positioning the puncture needle 2000 at a target tissue site on the left atrial wall and/or subsequent insertion of the distal portion 1902 of the medical implant delivery catheter 1900 into the opening formed at the target tissue site. The pre-formed curvature 1904 can provide a desired trajectory for the medical implant delivery catheter 1900 as it is advanced distally such that the puncture needle 2000 can contact a target tissue site on the left atrial wall at a lateral position relative to the medical implant delivery system 1700 and the distal portion 1902 of the implant delivery catheter 1900 can be inserted into the opening formed at the target tissue site.

In some embodiments, the expandable anchor 1850 can be triggered and/or actuated to assume an expanded state after the medical implant delivery system 1700 is positioned at or proximate to the desired location within the coronary sinus. In the expanded configuration, the expandable anchor 1850 can contact a wall of the coronary sinus 18 to facilitate stably positioning the medical implant delivery system 1700 at the desired location. Stable positioning of the medical implant delivery system 1700 can facilitate tissue puncture at the target tissue site and/or reliable deployment of the medical implant device 1950 into the opening. In some embodiments, expansion of the expandable anchor 1850 can provide stable positioning of the elongate housing 1800 against the coronary sinus 18 so as to facilitate reliable puncture of the target tissue site on the left atrial wall.

Referring to FIG. 23, the puncture needle sheath 2100 can be extended into the opening formed in the left atrial wall such that the radially expandable member 2150 associated with the distal portion 2102 of the puncture needle sheath 2100 can be positioned into the opening to enlarge the opening. Enlargement of the opening can facilitate subsequent positioning of the medical implant device 1950 into the opening. The radially expandable member 2150 can be triggered and/or actuated after it has been positioned into the opening to assume an expanded configuration so as to enlarge the opening. As described herein, in some embodiments, the distal portion 1902 of the medical implant delivery catheter 1900 can be inserted into the opening to provide desired dilation of the opening.

The puncture needle 2000 can be further advanced through the puncture needle outlet opening 2104 associated with the distal end 2106 of the puncture needle sheath 2100. The puncture needle 2000 can serve as a guide wire along which the medical implant delivery catheter 1900 can be advanced such that the medical implant device 1950 (not shown) can be positioned into the opening in the tissue. Alternatively, the puncture needle 2000 can be exchanged for a medical implant guide wire. For example, the puncture needle 2000 can be retracted after the opening in the left atrial wall is formed. The medical implant guide wire can be advanced through the puncture needle lumen of the medical implant delivery catheter 1900 into the left atrium 2 and the implant delivery catheter 1900 can be advanced along the medical implant guide wire into the left atrium 2 to deploy the medical implant device 1950. FIG. 23 shows that the outer sheath 2200 remains over the medical implant device 1950 while the opening is formed in the left atrial wall. In some embodiments, the medical implant device 1950 can be distal of the outer sheath 2200 while the opening is formed in the left atrial wall.

Referring to FIG. 24, the distal portion 1902 of the medical implant delivery catheter 1900 can be advanced through the opening formed in the left atrial wall such that the medical implant device 1950 can be positioned into the opening. The medical implant delivery catheter 1900 can be advanced along the puncture needle 2000 positioned into the left atrium 2 to position the medical implant device 1950 into the opening. Examples of processes for deploying an expandable shunt devices into the left atrial wall are provided in U.S. patent application Ser. No. 15/335,891, entitled "Systems for Deploying an Expandable Cardiac Shunt," which is incorporated herein in its entirety.

The expandable shunt device deployed into the opening formed in the left atrial wall can allow flow of blood from the left atrium 2 into the coronary sinus 18, and then into the right atrium 5, thereby alleviating elevated left atrial pressure. After the expandable shunt device is deployed into the left atrial wall, the puncture needle 2000 and the medical implant delivery catheter 1900 can be retracted. Subsequently, the medical implant delivery system 1700 can be retracted along the guide wire 50 out of the coronary sinus.

FIG. 25 is a flow diagram of an example of a process 2400 to deploy a medical implant delivery system for delivering a medical implant device. The medical implant delivery system can comprise one or more features as described herein, such as that of the medical implant delivery system 1700 described with reference to FIGS. 18 through 24.

In block 2402, the process 2400 can involve advancing the medical implant delivery system along a guide wire into a vessel, channel, chamber and/or organ. For example, the medical implant delivery system can be advanced into the coronary sinus along the guide wire. The medical implant delivery system can be used to access the target tissue site on a target vessel, channel, chamber and/or organ. For example, the medical implant delivery system can be used to access a target tissue site on a portion of the left atrial wall from within the coronary sinus. The medical implant delivery system can comprise an elongate housing, a medical implant delivery catheter extending alongside the elongate housing, and an outer sheath around the elongate housing and the medical implant delivery catheter. A medical implant device can be positioned on the medical implant delivery catheter for deployment onto the target vessel, channel, chamber and/or organ. For example, a shunt device, including an expandable shunt device, can be carried on the medical implant delivery catheter for deployment onto the left atrial wall.

After the medical implant delivery system is positioned at a desired location within the coronary sinus, the puncture needle can be deployed to pierce the tissue at the target tissue site. A puncture needle can slidably extend through a puncture needle lumen of the medical implant delivery catheter. In block 2404, the process 2400 can involve translating the outer sheath proximally to release a distal portion of medical implant delivery catheter. As described herein, the distal portion of the medical implant delivery catheter can comprise a pre-formed curvature. The distal portion can comprise a shape memory material such that the distal portion can assume the curved configuration after the outer sheath is slid proximally such that the outer sheath is no longer around the distal portion to position the distal portion alongside the elongate housing.

In block 2406, the process 2400 can involve translating the medical implant delivery catheter distally relative to the elongate housing. The medical implant delivery catheter can be advanced distally such that the puncture needle can contact the target tissue. In some embodiments, the puncture component of the puncture needle can be extended through a puncture needle outlet opening associated with a distal end of the medical implant delivery catheter to facilitate contact between the puncture component and the target tissue. In block 2408, the process 2400 can involve piercing tissue at the target tissue site to form an opening in the tissue using the puncture component extending through the distal outlet opening of the medical implant delivery catheter.

In block 2410, the process 2400 can involve extending a distal portion of the medical implant delivery catheter through the opening formed in the tissue. The distal portion of the medical implant delivery catheter can be advanced through the opening such that the medical implant device carried on the medical implant delivery can be positioned in the opening. In some embodiments, the distal portion can be configured to enlarge the opening in the tissue. For example, the distal portion can have a predetermined diameter to provide desired enlargement of the opening. In some embodiments, the medical implant delivery system can comprise a puncture needle sheath configured to slidably extend through the puncture needle lumen of the medical implant delivery catheter, and the puncture needle is configured to be slidably passed through a lumen of the puncture needle sheath. A radially expandable member can be associated with a distal portion of the puncture needle sheath. At least a portion of the radially expandable member can be positioned within the opening formed in the tissue and expanded to enlarge the opening.

In block 2412, the process 2400 can involve deploying the medical implant device positioned on the medical implant delivery catheter can into the opening formed in the tissue. For example, the shunt device can be deployed onto the left atrial wall.

Additional Embodiments

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain embodiments require at least one of X, at least one of Y and at least one of Z to each be present.

It should be appreciated that in the above description of embodiments, various features are sometimes grouped together in a single embodiment, Figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above, but should be determined only by a fair reading of the claims that follow.

It should be understood that certain ordinal terms (e.g., "first" or "second") may be provided for ease of reference and do not necessarily imply physical characteristics or ordering. Therefore, as used herein, an ordinal term (e.g., "first," "second," "third," etc.) used to modify an element, such as a structure, a component, an operation, etc., does not necessarily indicate priority or order of the element with respect to any other element, but rather may generally distinguish the element from another element having a similar or identical name (but for use of the ordinal term). In addition, as used herein, indefinite articles ("a" and "an") may indicate "one or more" rather than "one." Further, an operation performed "based on" a condition or event may also be performed based on one or more other conditions or events not explicitly recited.

Unless otherwise defined, all terms (including technical and scientific terms) used herein have the same meaning as commonly understood by one of ordinary skill in the art to which example embodiments belong. It be further understood that terms, such as those defined in commonly used dictionaries, should be interpreted as having a meaning that is consistent with their meaning in the context of the relevant art and not be interpreted in an idealized or overly formal sense unless expressly so defined herein.

The spatially relative terms "outer," "inner," "upper," "lower," "below," "above," "vertical," "horizontal," and similar terms, may be used herein for ease of description to describe the relations between one element or component and another element or component as illustrated in the drawings. It be understood that the spatially relative terms are intended to encompass different orientations of the device in use or operation, in addition to the orientation depicted in the drawings. For example, in the case where a device shown in the drawing is turned over, the device positioned "below" or "beneath" another device may be placed "above" another device. Accordingly, the illustrative term "below" may include both the lower and upper positions. The device may also be oriented in the other direction, and thus the spatially relative terms may be interpreted differently depending on the orientations.

Unless otherwise expressly stated, comparative and/or quantitative terms, such as "less," "more," "greater," and the like, are intended to encompass the concepts of equality. For example, "less" can mean not only "less" in the strictest mathematical sense, but also, "less than or equal to."

What is claimed is:

1. A medical implant delivery system comprising:
a puncture needle comprising an elongate portion and a puncture component associated with a distal end of the elongate portion, the puncture component being configured to pierce and form an opening in a target tissue wall;
a medical implant delivery catheter comprising a puncture needle lumen, the puncture needle being configured to be advanced through the puncture needle lumen, the puncture component being configured to be extended through a puncture needle outlet opening associated with a distal portion of the medical implant delivery catheter;
a deployable medical implant device separably positioned on the medical implant delivery catheter, the deployable medical implant device being adapted to remain implanted after withdrawal of the medical implant delivery catheter;

an outer delivery catheter comprising a medical implant delivery lumen, the medical implant delivery catheter being configured to be advanced through the medical implant delivery lumen, the distal portion of the medical implant delivery catheter being configured to be received within the medical implant delivery lumen and extended through a side outlet opening associated with a distal portion of the outer delivery catheter,
wherein a distal portion of the medical implant delivery catheter comprises a first pre-formed curvature, a distal portion of the outer delivery catheter comprises a second pre-formed curvature, and a distal portion of the puncture needle comprises a third pre-formed curvature, and the third pre-formed curvature having a radius of curvature smaller than that of the first pre-formed curvature,
wherein the distal portion of the medical implant delivery catheter comprises a lateral cross section having a shape that matches a shape of the side outlet opening on the distal portion of the outer delivery catheter to orient the medical implant delivery catheter as the medical implant delivery catheter extends through the side opening, and were in a lateral cross section of a proximal portion of the medical implant delivery catheter is without the shape; and
a proximal handle engaged with the medical implant delivery catheter and the outer delivery catheter, and comprising an advancer translatable distally to advance the medical implant delivery catheter and the outer delivery catheter.

2. The system of claim 1, further comprising:
a puncture needle sheath configured to be passed through the puncture needle lumen, wherein the puncture needle is configured to be passed through a lumen of the puncture needle sheath; and
an inflatable balloon circumferentially positioned around a distal portion of the puncture needle sheath, wherein the inflatable balloon is configured to be positioned within the opening formed in the target tissue wall and to enlarge the opening when the inflatable balloon is in an expanded configuration.

3. The system of claim 2, further comprising a medical implant delivery guide wire, wherein the medical implant delivery guide wire is configured to be slidably advanced through the lumen of the puncture needle sheath and to be exchangeable with the puncture needle.

4. The system of claim 1, wherein a distal portion of the medical implant delivery catheter is configured to be inserted into the opening formed in the target tissue wall, the distal portion comprising a predetermined diameter configured to enlarge the opening.

5. The system of claim 1, further comprising an outer delivery catheter guide wire, and wherein the outer delivery catheter comprises a guide wire lumen configured to receive the outer delivery catheter guide wire.

6. The system of claim 5, wherein the outer delivery catheter guide wire lumen extends along an off-center longitudinal axis of the outer delivery catheter.

7. The system of claim 1, wherein the medical implant delivery catheter comprises a first tapered distal portion comprising the first pre-formed curvature and the outer delivery catheter comprises a second tapered distal portion comprising the second pre-formed curvature, wherein the first pre-formed curvature and the second pre-formed curvature have a common orientation.

8. The system of claim 7, wherein the first pre-formed curvature comprises a radius of curvature smaller than that of the second pre-formed curvature.

9. The system of claim 1, further comprising an expandable anchor, wherein the expandable anchor and the side outlet opening are on opposing portions of the outer delivery catheter, and wherein the expandable anchor is configured to assume an expanded configuration to position the outer delivery catheter against the target tissue wall.

10. The system of claim 9, wherein the expandable anchor is on an outer edge of the second pre-formed curvature.

11. A medical implant delivery system comprising:
a medical implant delivery catheter carrying a deployable medical implant device that is separable from the medical implant delivery catheter and that is adapted to remain implanted after withdrawal of the medical implant delivery catheter, and the medical implant delivery catheter comprising a distal portion having a first pre-formed curvature; and
an outer delivery catheter comprising a medical implant delivery lumen, the distal portion of the medical implant delivery catheter being configured to be received within the medical implant delivery lumen and extended through a side outlet opening on a distal portion of the outer delivery catheter, the distal portion of the outer delivery catheter comprising a second pre-formed curvature and the side outlet opening being on an inner edge of the second pre-formed curvature, wherein a distal portion of the medical implant delivery catheter comprises a lateral cross section having a shape that matches a shape of the side outlet opening on the distal portion of the outer delivery catheter to orient the medical implant delivery catheter as the medical implant delivery catheter extends through the side outlet opening, and wherein a lateral cross section of a proximal portion of the medical implant delivery catheter is without the shape.

12. The system of claim 11, wherein the first pre-formed curvature and the second pre-formed curvature have a common orientation.

13. The system of claim 11, wherein the first pre-formed curvature comprises a radius of curvature smaller than that of the second pre-formed curvature.

14. The system of claim 11, wherein the outer delivery catheter comprises a guide wire lumen extending along an off-center longitudinal axis of the outer delivery catheter and wherein the guide wire lumen is configured to receive an outer delivery catheter guide wire.

15. A medical implant delivery system comprising:
a medical implant delivery catheter comprising a puncture needle lumen extending therethrough and a distal portion having a first pre-formed curvature;
a deployable medical implant device separably and circumferentially positioned around the first pre-formed curvature of the medical implant delivery catheter, the deployable medical implant device being adapted to remain implanted after withdrawal of the medical implant delivery catheter; and
an outer delivery catheter comprising:
a distal portion having a second pre-formed curvature, at least a portion of the medical implant delivery catheter configured to be disposed through a medical implant delivery lumen of the outer delivery catheter and be advanced out of a side outlet opening on the second pre-formed curvature, and
a guide wire lumen extending through the outer delivery catheter off-set from a central longitudinal axis of the outer delivery catheter; and
a proximal handle engaged with the meidcal implant delivery catheter and the outer delivery catheter, and comprising an advancer translatable distally to advance the medical implant delivery catheter and the outer delivery catheter,
wherein the distal portion of the medical implant delivery catheter comprises a lateral cross section having a shape that matches a shape of the side outlet opening on the distal portion of the outer delivery catheter to orient the medical implant delivery catheter as the medical implant delivery catheter extends through the side opening, and were in a lateral cross section of a proximal portion of the medical implant delivery catheter is without the shape.

16. The system of claim 15, wherein the deployable medical implant device comprises an expandable shunt device.

17. The system of claim 15, wherein the proximal handle comprises a pair of flexible arms configured to actuate controlled release of the deployable medical implant device from the medical implant delivery catheter.

18. The system of claim 15, wherein the proximal handle comprises a locking nut and a forward bracket, and the locking nut is fixed relative to the forward bracket to allow fixing a position of the medical implant delivery catheter and outer delivery catheter relative to the proximal handle.

* * * * *